US012624392B2

(12) United States Patent
Patterson et al.

(10) Patent No.: US 12,624,392 B2
(45) Date of Patent: May 12, 2026

(54) MOLECULAR ARRAY GENERATION USING PHOTORESIST

(71) Applicant: 10x Genomics, Inc., Pleasanton, CA (US)

(72) Inventors: David Michael Patterson, Oakland, CA (US); Denis Pristinski, Dublin, CA (US); Preyas Shah, Milpitas, CA (US); Steven William Short, Pleasanton, CA (US); Dieter Wilk, San Jose, CA (US); Siyuan Xing, Newark, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 5 days.

(21) Appl. No.: 17/565,047

(22) Filed: Dec. 29, 2021

(65) Prior Publication Data

US 2022/0228210 A1     Jul. 21, 2022

Related U.S. Application Data

(60) Provisional application No. 63/132,385, filed on Dec. 30, 2020.

(51) Int. Cl.
    *C12Q 1/6874*     (2018.01)
    *C12N 15/10*      (2006.01)

(52) U.S. Cl.
    CPC ....... *C12Q 1/6874* (2013.01); *C12N 15/1065* (2013.01); *C12N 15/1068* (2013.01); *C12Q 2521/101* (2013.01); *C12Q 2521/501* (2013.01)

(58) Field of Classification Search
    CPC ............ C12Q 1/6874; C12Q 2521/101; C12Q 2521/501; C12N 15/1065; C12N 15/1068;
    (Continued)

(56) References Cited

U.S. PATENT DOCUMENTS

| | | | |
|---|---|---|---|
| 5,472,881 A | 12/1995 | Beebe et al. | |
| 5,610,287 A | 3/1997 | Nikiforov et al. | |

(Continued)

FOREIGN PATENT DOCUMENTS

| | | |
|---|---|---|
| DE | 19932488 A1 | 2/2001 |
| EP | 2878671 | 6/2015 |

(Continued)

OTHER PUBLICATIONS

Love (Langmuir 2001, 17, 6005-6012).*

(Continued)

*Primary Examiner* — Robert T. Crow
*Assistant Examiner* — Allison E Schloop
(74) *Attorney, Agent, or Firm* — WILSON SONSINI GOODRICH & ROSATI

(57) ABSTRACT

Provided in some aspects are methods for light-controlled in situ surface patterning of a substrate. Compositions such as nucleic acid arrays produced by the methods are also disclosed. In some embodiments, a method disclosed herein comprises using photoresist for photocontrollable hybridization and/or ligation of nucleic acid molecules, wherein photoresist removal allows hybridization and/or ligation of nucleic acid molecules at the exposed area. A large diversity of barcodes can be created in molecules on the substrate via sequential rounds of light exposure, hybridization, and ligation.

24 Claims, 9 Drawing Sheets
(1 of 9 Drawing Sheet(s) Filed in Color)

$N^M$ = Diversity

(58) Field of Classification Search

CPC .... B01J 2219/00432; B01J 2219/00547; B01J 2219/00608; B01J 2219/00659; B01J 2219/00675; B01J 2219/00722; B01J 19/0046

See application file for complete search history.

(56) References Cited

U.S. PATENT DOCUMENTS

| | | | |
|---|---|---|---|
| 5,807,522 A | 9/1998 | Brown et al. | |
| 5,837,860 A | 11/1998 | Anderson et al. | |
| 6,737,236 B1 | 5/2004 | Pieken et al. | |
| 6,800,439 B1 | 10/2004 | McGall et al. | |
| 6,833,450 B1 | 12/2004 | McGall et al. | |
| 6,887,665 B2 | 5/2005 | Trulson et al. | |
| 6,949,638 B2 | 9/2005 | Mittmann et al. | |
| 6,985,655 B2 | 1/2006 | Yamamoto | |
| 7,005,259 B1 | 2/2006 | McGall et al. | |
| 7,053,198 B2 | 5/2006 | Goldberg et al. | |
| 7,144,700 B1 | 12/2006 | McGall et al. | |
| 7,259,258 B2 | 8/2007 | Kozlov et al. | |
| 7,264,929 B2 | 9/2007 | Rothberg et al. | |
| 7,309,593 B2 | 12/2007 | Ofstead et al. | |
| 7,375,234 B2 | 5/2008 | Sharpless et al. | |
| 7,427,678 B2 | 9/2008 | Peiken et al. | |
| 7,452,673 B2 | 11/2008 | McGall et al. | |
| 7,541,314 B2 | 6/2009 | Suciu et al. | |
| 7,547,775 B2 | 6/2009 | Kuimelis et al. | |
| 7,781,378 B2 | 8/2010 | Orth et al. | |
| 7,862,996 B2 | 1/2011 | Kuimelis et al. | |
| 7,972,792 B2 | 7/2011 | Fujimoto et al. | |
| 8,193,336 B2 | 6/2012 | Foote | |
| 8,227,253 B2 | 7/2012 | Kuimelis et al. | |
| 8,445,734 B2 | 5/2013 | Buehler et al. | |
| 8,481,714 B2 | 7/2013 | Fujimoto et al. | |
| 8,729,251 B2 | 5/2014 | Kuimelis et al. | |
| 8,859,196 B2 | 10/2014 | Trulson et al. | |
| 8,871,423 B2 | 10/2014 | Yun et al. | |
| 9,063,133 B2 | 6/2015 | Huang et al. | |
| 9,346,892 B2 | 5/2016 | Albert et al. | |
| 9,499,578 B2 | 11/2016 | Rajasekaran et al. | |
| 9,556,360 B2 | 1/2017 | McGall et al. | |
| 9,593,365 B2 | 3/2017 | Frisen et al. | |
| 9,983,204 B2 | 5/2018 | Maurer et al. | |
| 10,030,261 B2 | 7/2018 | Frisen et al. | |
| 10,150,791 B2 | 12/2018 | Stengele | |
| 10,174,368 B2 | 1/2019 | Zhou et al. | |
| 10,286,376 B2 | 5/2019 | Rajasekaran et al. | |
| 10,307,724 B2 | 6/2019 | Crnogorac et al. | |
| 10,385,335 B2 | 8/2019 | McGall et al. | |
| 10,391,467 B2 | 8/2019 | Zhou et al. | |
| 10,520,813 B2 | 12/2019 | Lai et al. | |
| 10,533,216 B2 | 1/2020 | McGall et al. | |
| 10,584,378 B2 | 3/2020 | Crnogorac et al. | |
| 10,597,715 B2 | 3/2020 | Zhou et al. | |
| 10,695,735 B2 | 6/2020 | Zhou et al. | |
| 10,732,166 B2 | 8/2020 | Ku et al. | |
| 10,852,237 B2 | 12/2020 | Chung et al. | |
| 10,872,924 B2 | 12/2020 | Ku et al. | |
| 10,913,070 B2 | 2/2021 | Zhou et al. | |
| 11,124,829 B2 | 9/2021 | Fisher et al. | |
| 11,162,132 B2 | 11/2021 | Frisen et al. | |
| 11,332,790 B2 | 5/2022 | Chell et al. | |
| 11,352,659 B2 | 6/2022 | Frisen et al. | |
| 2002/0102564 A1 | 8/2002 | Mittmann et al. | |
| 2002/0155588 A1 | 10/2002 | Fodor et al. | |
| 2005/0079529 A1 | 4/2005 | Fodor et al. | |
| 2005/0164258 A1 | 7/2005 | Goldberg et al. | |
| 2006/0240344 A1 | 10/2006 | Cole et al. | |
| 2008/0280773 A1 | 11/2008 | Fedurco et al. | |
| 2009/0023609 A1 | 1/2009 | Jung et al. | |
| 2010/0062494 A1* | 3/2010 | Church | C12Q 1/6855 435/91.52 |
| 2011/0059865 A1 | 3/2011 | Smith et al. | |
| 2011/0143967 A1 | 6/2011 | McGall et al. | |
| 2011/0223585 A1 | 9/2011 | Gullberg et al. | |
| 2011/0244448 A1 | 10/2011 | Shirai et al. | |
| 2014/0378345 A1 | 12/2014 | Hindson et al. | |
| 2015/0005200 A1 | 1/2015 | Hindson et al. | |
| 2015/0148239 A1* | 5/2015 | Peter | C12Q 1/6841 506/3 |
| 2016/0168629 A1 | 6/2016 | Drmanac et al. | |
| 2017/0016063 A1 | 1/2017 | McGall et al. | |
| 2017/0044524 A1 | 2/2017 | Pollom et al. | |
| 2017/0233722 A1 | 8/2017 | Seelig et al. | |
| 2017/0342406 A1 | 11/2017 | Rigatti et al. | |
| 2018/0057873 A1 | 3/2018 | Zhou et al. | |
| 2018/0112211 A1 | 4/2018 | Smith et al. | |
| 2018/0149611 A1 | 5/2018 | Tiao et al. | |
| 2018/0238855 A1 | 8/2018 | Ku et al. | |
| 2019/0165039 A1 | 5/2019 | Ku et al. | |
| 2019/0203275 A1 | 7/2019 | Frisen et al. | |
| 2019/0262794 A1 | 8/2019 | Rajasekaran | |
| 2019/0284619 A1 | 9/2019 | Zhou et al. | |
| 2019/0323088 A1 | 10/2019 | Boutet et al. | |
| 2019/0360041 A1 | 11/2019 | Wu et al. | |
| 2019/0361010 A1* | 11/2019 | Belhocine | G01N 33/532 |
| 2019/0366292 A1 | 12/2019 | McGall et al. | |
| 2019/0367969 A1 | 12/2019 | Belhocine et al. | |
| 2020/0002763 A1 | 1/2020 | Belgrader et al. | |
| 2020/0047146 A1 | 2/2020 | McGall | |
| 2020/0070119 A1 | 3/2020 | Crnogorac et al. | |
| 2020/0071752 A1 | 3/2020 | McGall | |
| 2020/0216895 A1 | 7/2020 | Khurana et al. | |
| 2020/0256862 A1 | 8/2020 | Shalek et al. | |
| 2020/0370105 A1 | 11/2020 | Zhou et al. | |
| 2020/0384436 A1 | 12/2020 | Crnogorac et al. | |
| 2021/0016241 A1 | 1/2021 | Righini et al. | |
| 2021/0017127 A1 | 1/2021 | Park et al. | |
| 2021/0032776 A1 | 2/2021 | Dentinger et al. | |
| 2021/0123040 A1 | 4/2021 | Macosko et al. | |
| 2021/0292834 A1 | 9/2021 | Daugharthy et al. | |
| 2021/0332351 A1 | 10/2021 | Horgan et al. | |
| 2021/0380629 A1 | 12/2021 | Rajasekaran et al. | |
| 2022/0023820 A1 | 1/2022 | Strauss et al. | |
| 2022/0106632 A1 | 4/2022 | Galonska et al. | |
| 2022/0127672 A1 | 4/2022 | Stoeckius | |
| 2022/0228201 A1 | 7/2022 | McDermott et al. | |
| 2022/0314187 A1 | 10/2022 | Price et al. | |
| 2024/0002932 A1 | 1/2024 | Cheng et al. | |
| 2024/0167077 A1 | 5/2024 | Patterson et al. | |

FOREIGN PATENT DOCUMENTS

| | | |
|---|---|---|
| EP | 3133171 | 2/2017 |
| WO | WO-2000033084 A2 | 6/2000 |
| WO | WO-2006044956 A1 | 4/2006 |
| WO | WO-2012140224 A1 | 10/2012 |
| WO | WO-2016075204 A1 | 5/2016 |
| WO | WO 2019/126040 | 6/2017 |
| WO | WO 2018/091676 | 5/2018 |
| WO | WO 2018/107054 | 6/2018 |
| WO | WO 2018/136856 | 7/2018 |
| WO | WO 2018/175779 | 9/2018 |
| WO | WO 2020/005503 | 1/2020 |
| WO | WO 2020/047007 | 3/2020 |
| WO | WO-2020047004 A2 | 3/2020 |
| WO | WO-2020123309 A1 | 6/2020 |
| WO | WO 2020/159794 | 8/2020 |
| WO | WO 2020/236992 | 11/2020 |
| WO | WO-2020257797 A1 | 12/2020 |
| WO | WO-2021097255 A1 | 5/2021 |
| WO | WO-2021167807 A1 | 8/2021 |
| WO | WO-2021168287 A1 | 8/2021 |
| WO | WO-2022103499 A1 | 5/2022 |
| WO | WO 2022/147134 | 7/2022 |
| WO | WO 2022/147139 | 7/2022 |
| WO | WO-2022147140 A1 | 7/2022 |
| WO | WO-2024006814 A1 | 1/2024 |

OTHER PUBLICATIONS

Klan (Chem. Rev. 2013, 113, 119-191).*

Kawano ( Nucleic Acids Symposium Series No. 53, pp. 173-174).*

(56)             References Cited

OTHER PUBLICATIONS

Smith (Genome Research (2017) 27:491-499).*
Pirrung ( Dynamic Studies in Biology (2005) pp. 341-368).*
Pirrung (Angew. Chem. Int. Ed.2002,41, 1276 ± 12890).*
Case-Green (Current Opinion in Chemical Biology 1998, 2:404-410).*
Cui (Macromol. Rapid Commun. 2013, 34, 310-329).*
Dean (Langmuir. Sep. 10, 2013; 29(36): . doi:10.1021/la402362u.).*
Bibikova (Clinical Chemistry 50, No. 12, 2004, 2384-2385).*
McGall (Proc. Natl. Acad. Sci. USAvol. 93, pp. 13555-13560, Nov. 1996).*
Dean (Langmuir2013, 29, 11535-11545).*
Dean, Biorecognition by DNA oligonucleotides after Exposure to Photoresists and Resist Removers, Langmuir, Aug. 2013, 29, 11535-11545 (Year: 2013).*
Beattie et al., "Advances in genosensor research," Clin Chem. (1995) 41(5): 700-6.
Beier et al., "Versatile derivatisation of solid support media for covalent bonding on DNA-microchips," Nucleic Acids Res. (1999) 27(9): 1970-1977.
Chrisey et al., "Covalent attachment of synthetic DNA to self-assembled monolayer films," Nucleic Acids Res. (1996) 24(15): 3031-3039.
Fahy et al., "Design and synthesis of polyacrylamide-based oligonucleotide supports for use in nucleic acid diagnostics," Nucleic Acids Res. (1993) 21(8): 1819-26.
Guo et al., "Direct fluorescence analysis of genetic polymorphisms by hybridization with oligonucleotide arrays on glass supports," Nucleic Acids Res. (1994) 22(24): 5456-5465.
Ikeda et al., "Chemically Caged Nucleic Acids," Chem. Letters. (2017), 46(5), 634-640.
Joos et al., "Covalent attachment of hybridizable oligonucleotides to glass supports," Anal Biochem. (1997) 247(1): 96-101.
Klan et al., "Photoremovable Protecting Groups in Chemistry and Biology: Reaction Mechanisms and Efficacy," Chem Rev. (2013) 113(1): 119-191.
Lamture et al., "Direct detection of nucleic acid hybridization on the surface of a charge coupled device," Nucleic Acids Res. (1994) 22(11): 2121-5.
Liu et al., "Optochemical control of deoxyoligonucleotide function via a nucleobase-caging approach," Acc Chem Res. (2014) 47(1): 45-55.
Miller et al., "Basic concepts of microarrays and potential applications in clinical microbiology," Clin Microbiol Rev. (2009) 22(4): 611-33.
Nikiforov et al., "The use of 96-well polystyrene plates for DNA hybridization-based assays: an evaluation of different approaches to oligonucleotide immobilization," Anal Biochem. (1995) 227(1): 201-9.
Rogers et al., "Use of a novel cross-linking method to modify adenovirus tropism," Gene Ther. (1997) 4(12): 1387-92.
Rogers et al., "Immobilization of oligonucleotides onto a glass support via disulfide bonds: A method for preparation of DNA microarrays," Anal Biochem. (1999) 266(1):23-30.

Running et al., "A procedure for productive coupling of synthetic oligonucleotides to polystyrene microtiter wells for hybridization capture," Biotechniques. (1990) 8(3): 276, 279.
Scheideler et al., "Recapitulating complex biological signaling environments using a multiplexed, DNA-patterning approach," Sci Adv.(2020) 6(12): eaay5696.
Shalon et al., "A DNA microarray system for analyzing complex DNA samples using two-color fluorescent probe hybridization," Genome Res. (1996) 6(7): 639-45.
Stimpson et al., "Real-time detection of DNA hybridization and melting on oligonucleotide arrays by using optical wave guides," PNAS. (1995) 92(14); 6379-6383.
Timofeev et al., "Regioselective immobilization of short oligonucleotides to acrylic copolymer gels," Nucleic Acids Res. (1996) 24(16): 3142-3148.
Zhang et al., "Single-base mutational analysis of cancer and genetic diseases using membrane bound modified oligonucleotides," Nucleic Acids Res. (1991) 19(14): 3929-33.
Handwerger et al., "Biotinylated photocleavable polyethylenimine: capture and triggered release of nucleic acids from solid supports," Bioconjug Chem. (2007) 18(3):717-23.
Allawi, Hatim T. and John SantaLucia. Thermodynamics and NMR of internal G T mismatches in DNA. Biochemistry 36(34):10581-10594 (1997).
Kanehisa, Minoru. Use of statistical criteria for screening potential homologies in nucleic acid sequences. Nucleic Acids Res 12(1 Pt 1):203-213 (1984).
Liu, Yang, et al. High-spatial-resolution multi-omics sequencing via deterministic barcoding in tissue. Cell 183(6):1665-1681 (2020).
PCT/US2021/065525 International Search Report and Written Opinion dated Apr. 21, 2022.
PCT/US2021/065530 International Search Report and Written Opinion dated Apr. 21, 2022.
PCT/US2021/065531 International Search Report and Written Opinion dated Apr. 25, 2022.
PCT/US2023/069221 International Search Report and Written Opinion dated Sep. 29, 2023.
PCT/US2023/069222 International Search Report and Written Opinion dated Oct. 2, 2023.
PCT/US2023/069223 International Search Report and Written Opinion dated Oct. 2, 2023.
PCT/US2023/069241 International Search Report and Written Opinion dated Oct. 16, 2023.
PCT/US2023/069244 International Search Report and Written Opinion dated Oct. 23, 2023.
PCT/US2023/069255 International Search Report and Written Opinion dated Oct. 2, 2023.
PCT/US2023/069258 International Search Report and Written Opinion dated Oct. 19, 2023.
PCT/US2023/069261 International Search Report and Written Opinion dated Oct. 11, 2023.
PCT/US2023/069263 International Search Report and Written Opinion dated Oct. 2, 2023.

* cited by examiner

MOLECULAR ARRAY GENERATION USING PHOTORESIST

CROSS-REFERENCE TO RELATED APPLICATION

This application claims priority to U.S. Provisional Patent Application No. 63/132,385, filed Dec. 30, 2020, entitled "MOLECULAR ARRAY GENERATION USING PHOTO-RESIST," which is herein incorporated by reference in its entirety for all purposes.

FIELD

The present disclosure relates in some aspects to methods for manufacturing a molecular array using photoresist and the molecular array generated in situ on a substrate.

BACKGROUND

Arrays of nucleic acids are an important tool in the biotechnology industry and related fields. These nucleic acid arrays, in which a plurality of distinct or different nucleic acids are positioned on a solid support surface in the form of an array or pattern, find use in a variety of applications, including gene expression analysis, drug screening, nucleic acid sequencing, mutation analysis, and the like.

A feature of many arrays that have been developed is that each of the distinct nucleic acids of the array is stably attached to a discrete location on the array surface, such that its position remains constant and known throughout the use of the array. Stable attachment is achieved in a number of different ways, including covalent bonding of a nucleic acid polymer to the support surface and non-covalent interaction of the nucleic acid polymer with the support surface.

There are two main ways of producing nucleic acid arrays in which the immobilized nucleic acids are covalently attached to the substrate surface, i.e., via in situ synthesis in which the nucleic acid polymer is grown on the surface of the substrate in a step-wise, nucleotide-by-nucleotide fashion, or via deposition of a full, presynthesized nucleic acid/polypeptide, cDNA fragment, etc., onto the surface of the array.

While nucleic acid arrays have been manufactured using in situ synthesis techniques, applications in the field of genomics and high throughput screening have fueled the demand for precise chemistry and high fidelity of the synthesized oligonucleotides. Accordingly, there is continued interest in the development of new methods for producing nucleic acid arrays in situ. Provided herein are methods, uses and articles of manufacture that meet such needs.

SUMMARY

In some aspects, disclosed herein is a method for providing an array, comprising: (a) irradiating a substrate comprising an unmasked first region and a masked second region, whereby a photoresist in the first region is degraded to render oligonucleotide molecules in the first region available for hybridization and/or ligation, whereas oligonucleotide molecules in the second region are protected by a photoresist in the second region from hybridization and/or ligation; and (b) attaching an oligonucleotide of at least four nucleotide residues in length to oligonucleotide molecules in the first region via hybridization and/or ligation, wherein oligonucleotide molecules in the second region do not receive a sequence of the oligonucleotide, thereby providing on the substrate an array comprising different oligonucleotide molecules in the first and second regions. In some embodiments, the oligonucleotide comprises a barcode sequence, and all or a portion of the barcode sequence is attached to oligonucleotide molecules in the first region, wherein oligonucleotide molecules in the second region do not receive the barcode sequence or portion thereof.

In any of the embodiments herein, the oligonucleotide molecules on the substrate can comprise one or more common sequences. In any of the embodiments herein, the one or more common sequences can comprise a homopolymeric sequence, such as a poly(dT) sequence, of three, four, five, six, seven, eight, nine, ten or more nucleotide residues in length. In any of the embodiments herein, the one or more common sequences can comprise a common primer sequence. In some embodiments, the common primer sequence is between about 10 and about 35 nucleotides in length. In any of the embodiments herein, the one or more common sequences can comprise a partial primer sequence. For example, a terminal sequence of an oligonucleotide molecule on the substrate together with a sequence of an oligonucleotide attached to the oligonucleotide molecule on the substrate can form the hybridization sequence for a primer. In this example, the terminal sequence of the oligonucleotide molecule on the substrate can be viewed as a partial primer sequence. In any of the embodiments herein, oligonucleotide molecules in the first region and oligonucleotide molecules in the second region can be identical in sequence. In any of the embodiments herein, oligonucleotide molecules on the substrate prior to the irradiating step can be identical in sequence. In any of the embodiments herein, oligonucleotide molecules in the first region and oligonucleotide molecules in the second region can be different in sequences, optionally wherein oligonucleotide molecules in the first region and oligonucleotide molecules in the second region comprise different barcode sequences. In any of the embodiments herein, oligonucleotide molecules on the substrate can comprise two or more different sequences, optionally wherein oligonucleotide molecules on the substrate can comprise two, three, four, five, six, seven, eight, nine, ten or more different barcode sequences.

In any of the embodiments herein, oligonucleotide molecules on the substrate can be immobilized in a plurality of features. In any of the embodiments herein, the 3' terminal nucleotides of the immobilized oligonucleotide molecules can be distal to the substrate or array surface. In any of the embodiments herein, the 5' terminal nucleotides of the immobilized oligonucleotide molecules can be more proximal to the substrate or array surface than the 3' terminal nucleotides. In any of the embodiments herein, one or more nucleotides at or near the 5' terminus of each immobilized oligonucleotide can be directly or indirectly attached to the substrate or array surface, thereby immobilizing the oligonucleotides. In any of the embodiments herein, the 3' terminus of each immobilized oligonucleotide can project away from the substrate or array surface. In any of the embodiments herein, the 5' terminal nucleotides of the immobilized oligonucleotide molecules can be distal to the substrate or array surface. In any of the embodiments herein, the 3' terminal nucleotides of the immobilized oligonucleotide molecules can be more proximal to the substrate or array surface than the 5' terminal nucleotides. In any of the embodiments herein, one or more nucleotides at or near the 3' terminus of each immobilized oligonucleotide can be directly or indirectly attached to the substrate or array surface, thereby immobilizing the oligonucleotides. In any of the embodiments herein, the 5' terminus of each immobilized oligonucleotide can project away from the substrate or array surface.

In any of the embodiments herein, oligonucleotide molecules on the substrate prior to the irradiating step can be between about 4 and about 100 nucleotides in length. In any of the embodiments herein, oligonucleotide molecules on the substrate prior to the irradiating step can be between about 10 and about 50 nucleotides in length.

In any of the embodiments herein, oligonucleotide molecules on the substrate can comprise functional groups, optionally wherein the functional groups are amino or hydroxyl groups. In any of the embodiments herein, prior to the irradiating step, the functional groups do not need to be protected by a protective group that is removed during and/or after the irradiating step. In any of the embodiments herein, prior to the irradiating step, the functional groups can be unprotected functional groups. In any of the embodiments herein, prior to the irradiating step, the functional groups can be amino or hydroxyl groups that are protected by the photoresist but are not reacted with protective groups. In any of the embodiments herein, prior to the irradiating step, the functional groups can be amino or hydroxyl groups that are not reacted with a protective group, moiety, or molecule that is photo-sensitive, photo-labile, photo-degradable, acid-labile or otherwise removable in a photo-activable reaction. In any of the embodiments herein, the functional groups can be 3' hydroxyl groups of nucleotides.

In any of the embodiments herein, the method can further comprise a step of providing the substrate, wherein the first and second regions have the same photoresists. In any of the embodiments herein, the providing step can comprise applying the photoresist to the substrate, thereby forming a photoresist layer on the substrate. In some embodiments, the photoresist can be applied to the substrate via spin coating and/or dipping. In any of the embodiments herein, oligonucleotide molecules on the substrate can be embedded in the photoresist. In any of the embodiments herein, oligonucleotide molecules on the substrate can be embedded in an underlayer, and the photoresist can form a photoresist layer on top of the underlayer. In any of the embodiments herein, the underlayer can be a soluble polymer.

In any of the embodiments herein, the method can further comprise forming a pattern of oligonucleotide molecules on the substrate prior to applying the photoresist to the substrate. In any of the embodiments herein, the forming step can comprise: irradiating a substrate comprising a plurality of functional groups and a photoresist through a patterned mask, whereby the photoresist in a first region of the substrate is degraded, rendering functional groups in the first region available for reacting with functional groups in functionalized oligonucleotide molecules, whereas functional groups in a second region of the substrate are protected by the photoresist from reacting with functional groups in the functionalized oligonucleotide molecules; and contacting the substrate with the functionalized oligonucleotide molecules, wherein the functionalized oligonucleotide molecules are coupled to functional groups in the first region but not to functional groups in the second region, thereby forming a pattern of oligonucleotide molecules on the substrate.

In any of the embodiments herein, the plurality of functional groups of the substrate (e.g., of a lawn of oligonucleotides) can remain unreacted functional groups (e.g., unreacted amino or hydroxyl groups that are protected by a photoresist from nucleic acid hybridization and/or ligation) prior to, during, and/or after the irradiating step, until the attachment of the oligonucleotide of at least four nucleotide residues in length. In any of the embodiments herein, the plurality of functional groups do not need to be deprotected in order to interact and/or react with the oligonucleotide of at least four nucleotide residues in length. In any of the embodiments herein, prior to the irradiating step, the plurality of functional groups of the substrate (e.g., of a lawn of oligonucleotides) do not need to be protected by a protective group, moiety, or molecule that is photo-sensitive, photo-labile, photo-degradable, acid-labile or otherwise removable in a photo-activable reaction.

In any of the embodiments herein, the plurality of functional groups of the substrate (e.g., of a lawn of oligonucleotides) can be protected prior to the irradiating step and deprotected during and/or after the irradiating step. In any of the embodiments herein, prior to the irradiating step, the plurality of functional groups of the substrate (e.g., of a lawn of oligonucleotides) can be protected by a protective group, moiety, or molecule that is photo-sensitive, photo-labile, photo-degradable, acid-labile or otherwise removable in a photo-activable reaction. In any of the embodiments herein, the protective group, moiety, or molecule can be removed, thereby deprotecting the plurality of functional groups and allowing them to interact and/or react with the oligonucleotide of at least four nucleotide residues in length.

In any of the embodiments herein, the plurality of functional groups (e.g., of a lawn of oligonucleotides) can be or comprise amino groups, hydroxyl groups, aldehyde groups, and/or click chemistry groups, optionally wherein the click chemistry groups are capable of a nucleophilic addition reaction, a cyclopropane-tetrazine reaction, a strain-promoted azide-alkyne cycloaddition (SPAAC) reaction, an alkyne hydrothiolation reaction, an alkene hydrothiolation reaction, a strain-promoted alkyne-nitrone cycloaddition (SPANC) reaction, an inverse electron-demand Diels-Alder (IED-DA) reaction, a cyanobenzothiazole condensation reaction, an aldehyde/ketone condensation reaction, or a Cu(I)-catalyzed azide-alkyne cycloaddition (CuAAC) reaction.

In any of the embodiments herein, the functional groups in the functionalized oligonucleotide molecules can be or comprise amino groups. In any of the embodiments herein, the functionalized oligonucleotide molecules can be 5' amine-terminated.

In any of the embodiments herein, the method can further comprise heating the substrate to dryness during or after the contacting step. In any of the embodiments herein, the method can further comprise blocking unreacted functional groups of the substrate.

In any of the embodiments herein, the method can further comprise rendering the reaction between functional groups of the substrate and the functionalized oligonucleotide molecules irreversible.

In any of the embodiments herein, aldehyde groups of the substrate can be reacted with 5' amino groups of the functionalized oligonucleotide molecules, and the substrate can be contacted with a reagent to block unreacted aldehyde groups and render the reaction irreversible. In any of the embodiments herein, the reagent can be or comprise sodium borohydride. In any of the embodiments herein, the reagent (e.g., sodium borohydride) can block unreacted aldehyde groups via reductive amination of an aldehyde-amine condensation reaction product.

In any of the embodiments herein, the irradiating and contacting steps can be repeated in one or more cycles, e.g., each cycle for coupling functionalized oligonucleotide molecules to functional groups in one or more regions of the substrate. In some embodiments, each cycle is for coupling functionalized oligonucleotide molecules to functional groups in a different region of the substrate. In some embodiments, the different regions of the substrate do not overlap. In any of the embodiments herein, the photoresist does not need to be removed prior to, during, or between the one or more cycles, optionally wherein the method does not comprise re-applying a photoresist to the substrate prior to, during, or between the one or more cycles. In any of the embodiments herein, the photoresist can be removed in a cycle and re-applied in the next cycle, and the removed photoresist and the re-applied photoresist can be the same or different. In any of the embodiments herein, the photoresist does not need to be removed prior to, during, or after each cycle or between cycles. In some embodiments, the photoresist remains on the substrate for a plurality of cycles and is removed after the plurality of cycles and re-applied prior to the next cycle. In some embodiments, the photoresist re-applied to the substrate is the same photoresist. In another embodiment, the photoresist re-applied to the substrate is a different photoresist.

In any of the embodiments herein, the photoresist in the first and/or second regions can comprise a photoacid generator. In any of the embodiments herein, the photoresist can comprise an acid scavenger. In any of the embodiments herein, the photoresist can comprise a base quencher. In any of the embodiments herein, the photoresist can comprise a photosensitizer. In any of the embodiments herein, the photoresist can comprise a surfactant and/or a casting solvent.

In any of the embodiments herein, the substrate can be irradiated with a UV light. In any of the embodiments herein, the substrate can be irradiated through a patterned mask. In any of the embodiments herein, the method can further comprise removing the patterned mask after the irradiating step, optionally wherein the same patterned mask can be re-used in a subsequent cycle of the irradiating and contacting steps, wherein the patterned mask is moved (e.g., rotated, for example, by 90 degrees) relative to the substrate; or optionally wherein a different patterned mask is used in a subsequent cycle of the irradiating and contacting steps. In any of the embodiments herein, the photoresist of the substrate can be dissolved by a developer and removed. In any of the embodiments herein, the photoresist in the first region of the substrate can be dissolved by a first developer and removed. In any of the embodiments herein, the photoresist in the second region of the substrate can be dissolved by a second developer and removed.

In any of the embodiments herein, the barcode sequence or any part thereof can be between about 4 and about 50 nucleotides in length. In any of the embodiments herein, the barcode sequence or any part thereof can be between about 5 and about 25 nucleotides in length.

In any of the embodiments herein, the oligonucleotide comprising the barcode sequence can be between about 10 and about 50 nucleotides in length. In any of the embodiments herein, the oligonucleotide comprising the barcode sequence can be hybridized to an oligonucleotide molecule in the first region. In any of the embodiments herein, the oligonucleotide comprising the barcode sequence can be ligated to an oligonucleotide molecule in the first region.

In any of the embodiments herein, the oligonucleotide comprising the barcode sequence can be hybridized to a splint which is in turn hybridized to an oligonucleotide molecule in the first region. In any of the embodiments herein, the method can further comprise ligating the oligonucleotide comprising the barcode sequence to the oligonucleotide molecule to generate a barcoded oligonucleotide molecule in the first region. In any of the embodiments herein, the oligonucleotide and the oligonucleotide molecule can be ligated using the splint as template, without or without gap filling prior to the ligation.

In any of the embodiments herein, the method can further comprise removing the splint after the ligation. In any of the embodiments herein, the splint can be removed by heat and/or treatment with a denaturing agent, such as KOH or NaOH. In any of the embodiments herein, the method can further comprise blocking the 3' or 5' termini of barcoded oligonucleotide molecules and/or unligated oligonucleotide molecules in the first region from ligation. In any of the embodiments herein, the blocking can comprise adding a 3' dideoxy, a non-ligating 3' phosphoramidate, or a triphenyl-methyl (trityl) group to the barcoded oligonucleotide molecules and/or unligated oligonucleotide molecules, optionally wherein the blocking by the trityl group is removed with a mild acid after ligation is completed. In any of the embodiments herein, the addition can be catalyzed by a terminal transferase, e.g., TdT. In any of the embodiments herein, the blocking can be removed using an internal digestion of the barcoded oligonucleotide molecules after ligation is completed.

In any of the embodiments herein, the method can comprise N cycles, wherein N is an integer of 2 or greater, and one or more or all of the N cycles comprises the irradiating and the attaching steps. In any of the embodiments herein, the irradiating and the attaching steps can be repeated N cycles, each cycle for one or more regions of the substrate (e.g., for one or more features on an array), for a round until all desired regions have been exposed to light, deprotected from the photoresist once, and oligonucleotide molecules in the exposed regions have received a barcode sequence for that round, which barcode sequence may be the same or different for molecules for any two given regions (e.g., features on an array). The barcode sequences for different cycles (e.g., each cycle for a different region of the substrate) in the same round can comprise the same or different sequences, and preferably the barcode sequences for different cycles are different. In any of the embodiments herein, the barcode sequences received by oligonucleotide molecules in feature(s) on the substrate in cycle I and in feature(s) in cycle J can be different, wherein I and J are integers and $1 \leq I < J \leq N$. In any of the embodiments herein, the photoresist may not need to be removed prior to, during, or between one or more of the N cycles. In any of the embodiments herein, a photoresist may not need to be re-applied to the substrate prior to, during, or between one or more of the N cycles of a given round. In any of the embodiments herein, the method can further comprise removing photoresist from the substrate after each cycle and re-applying photoresist to the substrate prior to the subsequent cycle of the same round or the first cycle of a subsequent round.

In any of the embodiments herein, the method can comprise M rounds, wherein M is an integer of 2 or greater, and each of the M rounds comprises one or more cycles. In any of the embodiments herein, each of the M rounds may comprise N cycles, optionally wherein each cycle is for attaching oligonucleotides to oligonucleotide molecules in one or more regions of the substrate (e.g., for one or more features on the array). In any of the embodiments herein, the method can further comprise removing photoresist from the substrate after each round or after one or more or all of a plurality of rounds (e.g., after two, three, or more sequential rounds) and re-applying photoresist to the substrate prior to a new round. In any of the embodiments herein, each of the M rounds can comprise N cycles, wherein N is 3 or greater. In any of the embodiments herein, each of the M rounds can comprise the same number of cycles, or two or more of the M rounds can comprise different numbers of cycles. With reference to FIG. 2, although the figure shows Cycle 1, Cycle 2, . . . , Cycle N for each of Round 1 and Round M, it should be appreciated that any two rounds of Round 1 to Round M may comprise the same number or different numbers of sequential cycles. For instance, Round 2 may comprise fewer than N cycles, whereas Round 3 may comprise more than N cycles. For instance, Cycle 1 and Cycle 2 of Round 2 may be combined into one cycle and the regions in these cycles receive the same oligonucleotide, and in Round 3 the regions after Cycle (N–1) may be grouped into two sets, one set for Cycle N and the other set for Cycle (N+1), and each set may receive a different oligonucleotide. One or more rounds comprising the attachment of a common nucleic acid sequence may be performed before or after any of Round 1 to Round M, and the nucleic acid sequence can be common to two or more regions on the substrate. In some cases, the nucleic acid sequence can be universal and can be shared by all of the regions on the substrate.

In any of the embodiments herein, oligonucleotide molecules in a feature of the substrate can receive a first barcode sequence in one of the cycles in round K, wherein K is an integer and $1 \leq K < M$, and oligonucleotide molecules in the feature comprising the first barcode sequence receive a second barcode sequence in one of the cycles in round (K+1), thereby forming oligonucleotide molecules comprising the first and second barcode sequences. In any of the embodiments herein, the diversity of barcode sequences in the oligonucleotides in a plurality of features on the substrate can be $N^M$. In any of the embodiments herein, the feature(s) can be no more than 0.5 micron, no more than 1 micron, no more than 5 microns, no more than 7 microns, no more than 10 microns, or no more than 15 microns, no more than 20 microns, no more than 25 microns, no more than 30 microns, or no more than 35 microns, no more than 40 microns, no more than 45 microns, or no more than 50 microns in diameter. In any of the embodiments herein, the feature(s) can be no more than 500 nm, no more than 600 nm, no more than 700 nm, no more than 800 nm, no more than 900 nm, no more than 1 micron, no more than 1.5 microns, no more than 2 microns, no more than 2.5 microns, no more than 3 microns, no more than 3.5 microns, no more than 4 microns, no more than 4.5 microns, or no more than 5 microns in one dimension. In any of the embodiments herein, the feature(s) can be no more than 500 nm, no more than 600 nm, no more than 700 nm, no more than 800 nm, no more than 900 nm, no more than 1 micron, no more than 1.5 microns, no more than 2 microns, no more than 2.5 microns, no more than 3 microns, no more than 3.5 microns, no more than 4 microns, no more than 4.5 microns, or no more than 5 microns in two dimensions.

In some aspects, provided herein is a method for providing an array, comprising: (a) irradiating a substrate comprising an unmasked first region and a masked second region, whereby a photoresist in the first region is degraded to render oligonucleotide molecules in the first region available for hybridization and/or ligation, whereas oligonucleotide molecules in the second region are protected by the photoresist in the second region from hybridization and/or ligation; and (b) contacting oligonucleotide molecules in the first region with a first splint and a first oligonucleotide comprising a first barcode sequence, wherein the first splint hybridizes to the first oligonucleotide and one of the oligonucleotide molecules in the first region, wherein the first oligonucleotide is ligated to the oligonucleotide molecules in the first region, and the first oligonucleotide is not ligated to oligonucleotide molecules in the second region, thereby providing on the substrate an array comprising different oligonucleotide molecules in the first and second regions.

In any of the embodiments herein, the hybridization region between the first splint and one of the oligonucleotide molecules can be at least 3, 4, 5, 6, 7, 8, 9, 10 bp or more than 10 bp. In any of the embodiments herein, the hybridization region between the first splint and the first oligonucleotide can be at least 3, 4, 5, 6, 7, 8, 9, 10 bp or more than 10 bp.

In any of the embodiments herein, hybridization to the first splint can bring the terminal nucleotides of the first oligonucleotide and one of the oligonucleotide molecules immediately next to each other, and the ligation of the juxtaposed first oligonucleotide and oligonucleotide molecules on the substrate does not require gap-filling. In any of the embodiments herein, hybridization to the first splint can bring the terminal nucleotides of the first oligonucleotide and one of the oligonucleotide molecules in proximity to each other and separated by one or more nucleotides, and the ligation of the juxtaposed first oligonucleotide and oligonucleotide molecules on the substrate is preceded by gap-filling.

In any of the embodiments herein, the photoresist can be a first photoresist, and the first oligonucleotide is ligated to the oligonucleotide molecules in the first region to generate first extended oligonucleotide molecules, and the method can further comprise: (c) applying a second photoresist to the substrate, optionally wherein the second photoresist is applied after the first photoresist is removed from the substrate; (d) irradiating the substrate while the first region is masked and the second region is unmasked, whereby the first and/or second photoresist in the second region is degraded to render oligonucleotide molecules in the second region available for hybridization and/or ligation, whereas the first extended oligonucleotide molecules in the first region are protected by the second photoresist in the first region from hybridization and/or ligation; and (e) contacting oligonucleotide molecules in the second region with a second splint and a second oligonucleotide comprising a second barcode sequence, wherein the second splint hybridizes to the second oligonucleotide and one of the oligonucleotide molecules in the second region, wherein the second oligonucleotide is ligated to the oligonucleotide molecules in the second region to generate second extended oligonucleotide molecules, and the second oligonucleotide is not ligated to the first extended oligonucleotide molecules in the first region.

In any of the embodiments herein, steps (a)-(b) can be part of a first cycle, steps (d)-(e) can be part of a second cycle, and steps (a)-(e) can be part of a first round (comprising the first and second cycles), and wherein the method can comprise one or more additional rounds, each with one or more cycles of the irradiating and the contacting steps. In any of the embodiments herein, steps (a)-(e) can be part of a first round, the first and second oligonucleotides can be Round 1 oligonucleotides, the first and second barcode sequences can be Round 1 barcode sequences, and the method can further comprise: (a') irradiating the substrate while the first region is unmasked and the second region is masked, whereby a photoresist in the first region is degraded to render the first extended oligonucleotide molecules in the first region available for hybridization and/or ligation, whereas the second extended oligonucleotide molecules in the second region are protected by the photoresist in the second region from hybridization and/or ligation; and (b') attaching a first Round 2 oligonucleotide comprising a first Round 2 barcode sequence to the first extended oligonucleotide molecules in the first region via hybridization and/or ligation, wherein the second extended oligonucleotide molecules in the second region do not receive the first Round 2 barcode sequence.

In any of the embodiments herein, the photoresist can be a first photoresist, and the first Round 2 oligonucleotide can be ligated to the first extended oligonucleotide molecules in the first region to generate first further extended oligonucleotide molecules, and the method can further comprise: (c') applying a second photoresist to the substrate, optionally wherein the second photoresist is applied after the first photoresist is removed from the substrate; (d') irradiating the substrate while the first region is masked and the second region is unmasked, whereby the first or second photoresist in the second region is degraded to render the second extended oligonucleotide molecules in the second region available for hybridization and/or ligation, whereas the first further extended oligonucleotide molecules in the first region are protected by the second photoresist in the first region from hybridization and/or ligation; and (e') attaching a second Round 2 oligonucleotide comprising a second Round 2 barcode sequence to the second extended oligonucleotide molecules in the second region via hybridization and/or ligation, wherein the first further extended oligonucleotide molecules in the first region do not receive the second Round 2 barcode sequence.

In other embodiments, the method can further comprise: (a') irradiating the substrate while the second region is unmasked and the first region is masked, whereby a photoresist in the second region is degraded to render the second extended oligonucleotide molecules in the second region available for hybridization and/or ligation, whereas the first extended oligonucleotide molecules in the first region are protected by the photoresist in the first region from hybridization and/or ligation; and (b') attaching a first Round 2 oligonucleotide comprising a first Round 2 barcode sequence to the second extended oligonucleotide molecules in the second region via hybridization and/or ligation, wherein the first extended oligonucleotide molecules in the first region do not receive the first Round 2 barcode sequence.

In some aspects, provided herein is a method for providing an array, comprising: (a) irradiating a substrate comprising an unmasked first region and a masked second region, whereby photoresist in the first region is degraded to render oligonucleotide molecules in the first region available for hybridization and/or ligation, whereas oligonucleotide molecules in the second region are protected by photoresist in the second region from hybridization and/or ligation; and (b) attaching a first oligonucleotide of at least four residues in length (e.g., comprising a first barcode sequence) to oligonucleotide molecules in the first region via hybridization and/or ligation, wherein oligonucleotide molecules in the second region are not ligated to the first oligonucleotide or a portion thereof, thereby providing on the substrate an array comprising different oligonucleotide molecules in the first and second regions. In some aspects, the method further comprises (a') irradiating the unmasked second region, whereby photoresist in the second region is degraded to render oligonucleotide molecules in the second region available for hybridization and/or ligation; (b') attaching a second oligonucleotide of at least four residues in length (e.g., comprising a second barcode sequence) to oligonucleotide molecules in the second region via hybridization and/or ligation, whereas oligonucleotide molecules in the first region are not hybridized and/or ligated to the second oligonucleotide. For instance, oligonucleotide molecules in the first region may be protected by (i) photo-cleavable polymers bound to oligonucleotide molecules in the first region and/or (ii) photo-cleavable moieties of oligonucleotide molecules in the first region from hybridization and/or ligation, and/or splints can be used to hybridize to the second oligonucleotide and template ligation of the second oligonucleotide specifically to oligonucleotide molecules in the second region but not to oligonucleotide molecules in the first region based on sequence complementarity.

In some embodiments, the photoresist can be a first photoresist, and the first Round 2 oligonucleotide can be ligated to the second extended oligonucleotide molecules in the second region to generate second further extended oligonucleotide molecules, and the method can further comprise: (c') applying a second photoresist to the substrate, optionally wherein the second photoresist is applied after the first photoresist is removed from the substrate; (d') irradiating the substrate while the second region is masked and the first region is unmasked, whereby the first or second photoresist in the first region is degraded to render the first extended oligonucleotide molecules in the first region available for hybridization and/or ligation, whereas the second further extended oligonucleotide molecules in the second region are protected by the second photoresist in the second region from hybridization and/or ligation; and (e') attaching a second Round 2 oligonucleotide comprising a second Round 2 barcode sequence to the first extended oligonucleotide molecules in the first region via hybridization and/or ligation, wherein the second further extended oligonucleotide molecules in the second region do not receive the second Round 2 barcode sequence.

In any of the embodiments herein, the Round 1 barcode sequences can be different from each other. In any of the embodiments herein, the Round 2 barcode sequences can be different from each other. In any of the embodiments herein, the Round 1 barcode sequences can be different from the Round 2 barcode sequences.

In any of the embodiments herein, the oligonucleotide molecules on the substrate can comprise functional groups, optionally wherein the functional groups can be or comprise amino groups, hydroxyl groups, aldehyde groups, and/or click functional groups. In any of the embodiments herein, the functional groups do not need to be reacted with and/or protected by a chemical group, e.g., by a photo-sensitive protective group, moiety, or molecule. In any of the embodiments herein, the functional groups can be 3' hydroxyl groups of nucleotides.

In some aspects, provided herein is a composition comprising: (i) a substrate comprising a first region and a second region, (ii) hybridization complexes in the first region, wherein at least one of the hybridization complexes comprise an oligonucleotide molecule immobilized in the first region hybridized to a first splint, which is in turn hybridized to a first oligonucleotide comprising a first barcode sequence, and (iii) oligonucleotide molecules immobilized in the second region and protected by a photoresist from hybridization and/or ligation.

In some embodiments, provided herein is a composition, comprising: (i) a substrate comprising a first region and a second region, (ii) hybridization complexes in the first region, wherein at least one of the hybridization complexes comprise an oligonucleotide molecule immobilized in the first region hybridized to a first splint, which is in turn hybridized to a first oligonucleotide comprising a first barcode sequence, wherein the hybridization complexes are protected by a first photoresist from hybridization and/or ligation, and (iii) oligonucleotide molecules immobilized in the second region and protected by a second photoresist from hybridization and/or ligation. In some embodiments, the first photoresist and the second photoresist are the same. In some embodiments, the first photoresist and the second photoresist are different. In any of the embodiments herein, the oligonucleotide molecules on the substrate can comprise functional groups, optionally wherein the functional groups can be amino or hydroxyl groups. In any of the embodiments herein, the functional groups may be unreacted or unprotected functional groups. For example, in some embodiments, the functional groups have not been reacted with and/or protected by a photo-sensitive group, moiety, or molecule. In some embodiments, the functional groups can be 3' hydroxy groups of nucleotides.

In some embodiments, provided herein is a composition, comprising a substrate comprising a plurality of universal oligonucleotide molecules immobilized thereon, wherein the universal oligonucleotide molecules in a first region of the substrate are available for hybridization and/or ligation, and the universal oligonucleotide molecules in a second region of the substrate are embedded in a photoresist and protected from hybridization and/or ligation. In some embodiments, the composition further comprises a photomask masking the second region while exposing the first region to light. In some embodiments, the composition further comprises hybridization complexes in the first region, wherein at least one of the hybridization complexes comprise a universal oligonucleotide molecule immobilized in the first region hybridized to a first splint, which is in turn hybridized to a first oligonucleotide comprising a first barcode sequence. In some embodiments, the universal oligonucleotide molecules on the substrate can comprise functional groups. In some embodiments, the functional groups may be amino or hydroxyl groups. In some embodiments, the functional groups may not be protected. For example, in some embodiments, the functional groups may not be protected by a photo-sensitive group, moiety, or molecule. In some embodiments, the functional groups can be 3' hydroxyl group of nucleotides.

In any of the embodiments herein, the composition can further comprise the photoresist. In the composition of any of the preceding embodiments, the photoresist can form a photoresist layer and oligonucleotide molecules immobilized in the second region can be embedded in the photoresist layer.

In any of the embodiments herein, the composition can further comprise a ligase capable of ligating the first oligonucleotide and the oligonucleotide molecule immobilized in the first region using the first splint as template, and optionally a polymerase capable of gap filling using the first splint as template prior to the ligation. In any of the embodiments herein, the composition may not comprise any dNTP or a polymerase capable of incorporating a dNTP into an oligonucleotide molecule. In any of the embodiments herein, the composition may not comprise any reagent for base-by-base oligonucleotide synthesis.

In any of the embodiments herein, a method disclosed herein may not comprises a step of contacting the substrate or oligonucleotide molecules immobilized thereon with any reagent for base-by-base oligonucleotide synthesis.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
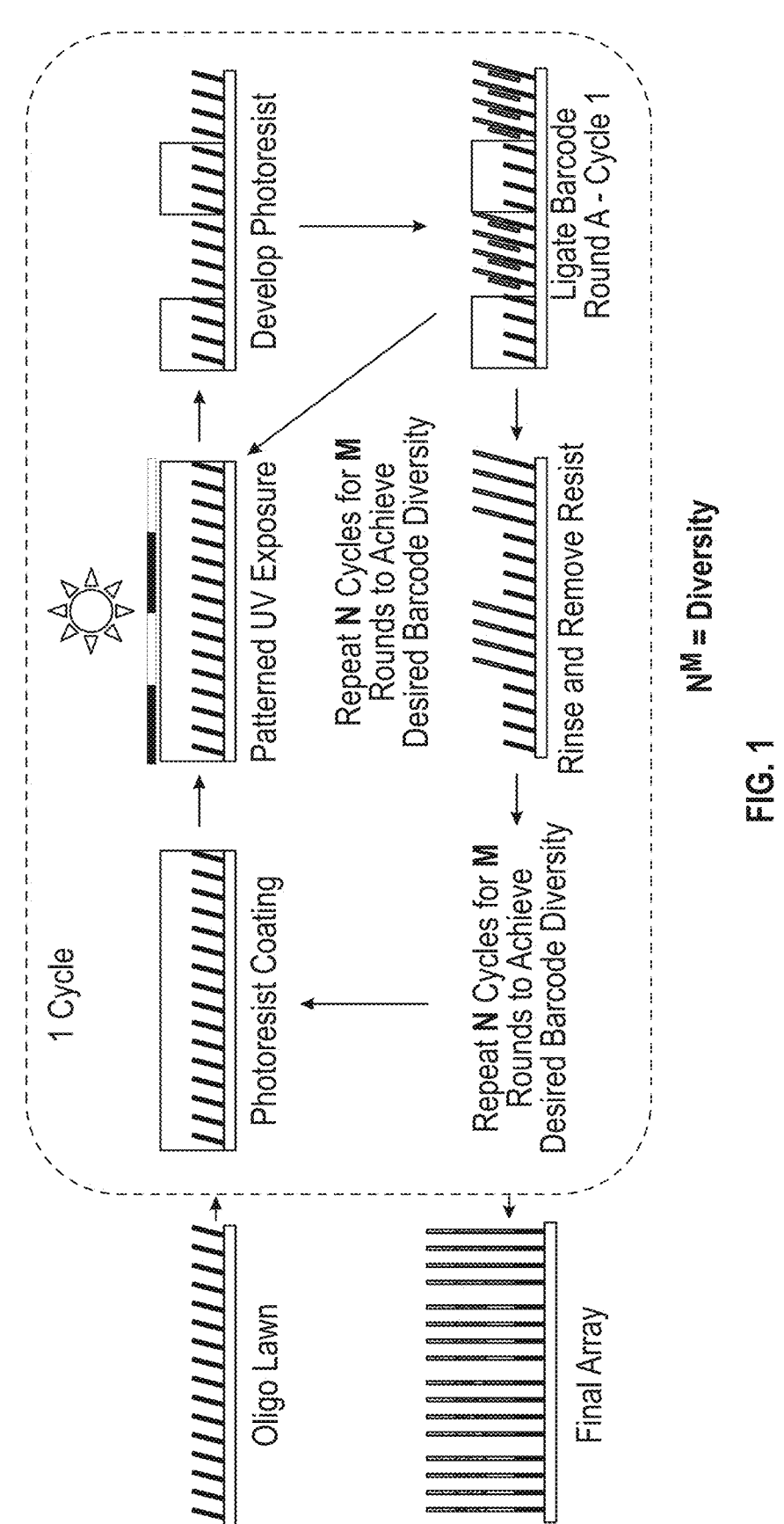
FIG. 1 shows an exemplary method for in situ array generation using photoresist.

The practice of the techniques described herein may employ, unless otherwise indicated, conventional techniques and descriptions of organic chemistry, polymer technology, molecular biology (comprising recombinant techniques), cell biology, biochemistry, and sequencing technology, which are within the skill of those who practice in the art. Such conventional techniques comprise polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), *Genetic Variation: A Laboratory Manual*; Dieffenbach, Dveksler, Eds. (2003), *PCR Primer: A Laboratory Manual*; Bowtell and Sambrook (2003), DNA *Microarrays: A Molecular Cloning Manual*; Mount (2004), *Bioinformatics: Sequence and Genome Analysis*; Sambrook and Russell (2006), *Condensed Protocols from Molecular Cloning: A Laboratory Manual*; and Sambrook and Russell (2002), Molecular Cloning: A Laboratory Manual (all from Cold Spring Harbor Laboratory Press); Stryer, L. (1995) *Biochemistry* (4th Ed.) W. H. Freeman, New York N.Y.; Gait, "*Oligonucleotide Synthesis: A Practical Approach*" 1984, IRL Press, London; Nelson and Cox (2000), Lehninger, *Principles of Biochemistry* 3rd Ed., W. H. Freeman Pub., New York, N.Y.; and Berg et al. (2002) *Biochemistry*, 5th Ed., W. H. Freeman Pub., New York, N.Y., all of which are herein incorporated in their entirety by reference for all purposes.

All publications, comprising patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Overview

Oligonucleotide arrays for spatial transcriptomics may be made by mechanical spotting, bead arrays, and/or in situ base-by-base synthesis of the oligonucleotides. In some cases, mechanical spotting is ideal for larger spot sizes (e.g., 30 microns in diameter or greater), since fully elaborated oligos (e.g., with a desired combination and diversity of barcodes) can be spotted in a known position with high purity and fidelity. However, methods to decrease spot sizes or features at or below 10 microns (e.g., single cell scale resolution) in diameter with sufficient throughput are lacking. In some aspects, bead arrays offer a way to increase feature density. For example, barcodes are generated by first attaching an oligonucleotide to all beads and then performing multiple rounds of split-pool ligations to generate barcodes combinatorially. However, in some aspects, bead arrays result in random barcoded bead arrays that must be decoded prior to use and each array ultimately has a unique pattern (see, U.S. Pat. No. 11,162,132). Additionally, even monodisperse beads at the 1-10 micron scale may have some variability that results in a range of feature sizes with the potential for variable oligo density.

Methods for in situ generated arrays have utilized photocleavable protecting groups to synthesize barcode oligonucleotides one nucleotide at a time. The feature size can be highly controlled using photomasks and the generated array is known and uniform across all arrays with no decoding needed. However, the oligonucleotide fidelity for in situ arrays decreases with increasing oligonucleotide length with a ~99% per step efficiency. Accordingly, as the oligonucleotide length increases (e.g., via incorporation of each nucleotide), the nucleotide incorporation error rate also increases.

In some embodiments, provided herein are methods for the fabrication of patterned arrays (e.g., a substrate having coupled to it a plurality of polymer molecules, such as oligonucleotides) with high spatial resolution using a photoresist. Provided herein in some embodiments are methods and uses of light-controlled combinatorial barcode generation for in situ arrays. In some embodiments, light-controlled ligation for in situ combinatorial barcode generation is utilized.

Provided herein in some embodiments are methods and uses of photohybridization-ligation combinatorial barcode generation using a photoresist and photolithography for in situ arrays. For example, a method disclosed herein may comprise photocontrollable ligation, wherein localized irradiation causes degradation of photoresist and oligonucleotides to be exposed for ligation. In some aspects, a method disclosed herein provides one or more advantages as compared to available arraying methods. For example, a large diversity of barcodes can be created via sequential rounds of UV exposure, hybridization, ligation, removal and reapplication of photoresist; no protection/deprotection step is required for ligating oligonucleotides to the substrate; the feature size can be highly controlled (e.g., submicron scale) using photomasks and the generated array at any discrete location is known and consistent (e.g., no incorporation errors) across all arrays with no decoding needed.

In some embodiments, the method described herein comprises a plurality of rounds, wherein each round comprises one or more cycles. In some embodiments, each cycle within the same round comprises the following general steps: (1) selective removal of photoresist by irradiation/UV exposure; (2) ligation of oligonucleotide; (3) blocking or capping, wherein the steps are reiterated for different features. In some embodiments, each feature receives at most one oligonucleotide in a round, wherein all features are ligated to at most one part of one or more barcodes.

FIG. 1 provides a non-limiting example of a method for generating an in situ oligonucleotide array using hybridization/ligation and a photoresist. A photoresist coating can be applied to a substrate comprising nucleic acid molecules, such as an oligonucleotide lawn. The oligonucleotide lawn can comprise a universal primer sequence. The photoresist coating is subjected to patterned UV exposure to selectively remove photoresist at pre-determined positions (e.g., features) on the substrate. The patterned UV exposure may be achieved by irradiating the photoresist-covered substrate with UV light through a photomask. After developing the photoresist, oligonucleotides comprising a first part of a barcode are applied to the substrate and hybridize to splints that hybridize to the oligonucleotide lawn. The oligonucleotides comprising the first part of a barcode may be ligated to molecules of the oligonucleotide lawn at the pre-determined positions. After ligation, the photoresist coating can be optionally removed, and the irradiation-development-ligation steps are repeated for N cycles, each cycle for one or more different pre-determined positions on the substrate. After all features are ligated to the first barcode, the round may be optionally repeated. In some cases, the round is repeated M times to ligate M parts of the barcode onto the substrate, generating a nucleotide array with $N^M$ sequence diversity.

Figure 2:
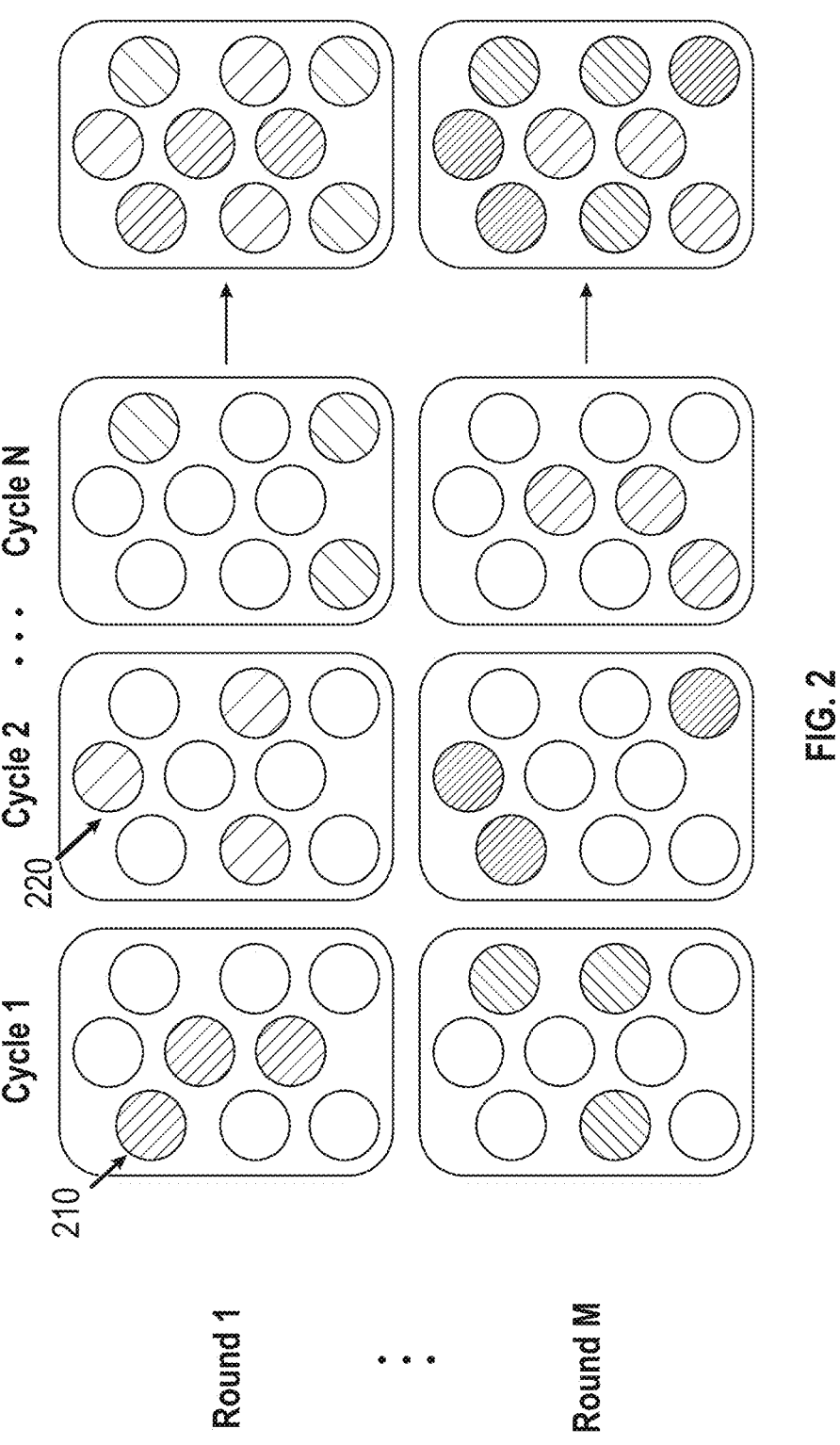
FIG. 2 is a schematic illustration of an exemplary method comprising M rounds, each of which comprise N cycles.

FIG. 2 further provides a schematic demonstration of an exemplary method for synthesis of barcoded oligonucleotides. In FIG. 2, substrate regions (e.g., features) are shown in circles. During cycle 1 of round 1, a first barcode sequence or a first part of a barcode sequence is attached to oligonucleotide molecules in the circles marked with diagonal lines in cycle 1 (210). Cycle 2 of round 1 attaches another first barcode sequence or a first part of another barcode sequence to oligonucleotide molecules in a different set of substrate regions marked with diagonal lines in cycle 2 (220), wherein the sequence of the oligonucleotide attached to the set of features marked in cycle 2 (220) may be different from those attached to the set of features marked in cycle 1 (210). Upon completion of N cycles in round 1, all substrate regions are ligated with the first barcode sequences or the first part sequences. Similarly, upon completion of N cycles in round M, all features are ligated with the $M^{th}$ barcode sequences or the $M^{th}$ part sequences, and an array with $N^M$ barcode diversity is generated.

II. Photolithography and Molecular Arrays

A. Photoresist

A photoresist is a light-sensitive material used in processes (such as photolithography and photoengraving) to form a pattern on a surface. A photoresist may comprise a polymer, a sensitizer, and/or a solvent. The photoresist composition used herein is not limited to any specific proportions of the various components.

Photoresists can be classified as positive or negative. In positive photoresists, the photochemical reaction that occurs during light exposure weakens the polymer, making it more soluble to developer, so a positive pattern is achieved. In the case of negative photoresists, exposure to light causes polymerization of the photoresist, and therefore the negative photoresist remains on the surface of the substrate where it is exposed, and the developer solution removes only the unexposed areas. In some embodiments, the photoresist used herein is a positive photoresist. In some embodiments, the photoresist is degraded or removable with UV light.

In some aspects, disclosed herein is a method for providing an array, comprising: (a) irradiating a substrate comprising an unmasked first region and a masked second region, whereby a photoresist in the first region is degraded to render oligonucleotide molecules in the first region available for hybridization and/or ligation, whereas oligonucleotide molecules in the second region are protected by a photoresist in the second region from hybridization and/or ligation; and (b) attaching an oligonucleotide comprising a sequence of at least 4 nucleotides in length to oligonucleotide molecules in the first region via hybridization and/or ligation, wherein oligonucleotide molecules in the second region do not receive the sequence of at least 4 nucleotides in length, thereby providing on the substrate an array comprising different oligonucleotide molecules in the first and second regions. The photoresist may experience changes in pH upon irradiation. In some embodiments, the photoresist in the first region comprises a photoacid generator (PAG). In some embodiments, the photoresist in the second region comprises a photoacid generator. In some embodiments, the photoresist in the first and the second region comprises a photoacid generator. In some embodiments, the photoresist in the first and the second region comprises the same photoacid generator. In some embodiments, the photoresist in the first and the second region comprises different photoacid generators. In some embodiments, the photoacid generator or photoacid generators irreversibly release protons upon absorption of light. Photoacid generators may be used as components of photocurable polymer formulations and chemically amplified photoresists. Examples of photoacid generators include triphenylsulfonium triflate, diphenylsulfonium triflate, diphenyliodonium nitrate, N-Hydroxynaphthalimide triflate, triarylsulfonium hexafluorophosphate salts, N-hydroxy-5-norbornene-2,3-dicarboximide perfluoro-1-butanesulfonate, bis(4-tert-butylphenyl)iodonium perfluoro-1-butanesulfonate, triphenylsulfonium trifluoromethanesulfonate, triphenylsulfonium nonafluoro-n-butanesulfonate, triphenylsulfonium perfluoro-n-octanesulfonate, and triphenylsulfonium 2-(bicyclo[2.2.1]heptan-2-yl)-1,1,2,2-tetrafluoroethanesulfonate, 4-cyclohexylphenyldiphenylsulfonium trifluoromethanesulfonate, 4-cyclohexylphenyldiphenylsulfonium nonafluoro-n-butanesulfonate, 4-cyclohexylphenyldiphenylsulfonium perfluoro-n-octanesulfonate, 4-cyclohexylphenyldiphenylsulfonium 2-(bicyclo[2.2.1] heptan-2-yl)-1,1,2,2-tetrafluoroethanesulfonate, 4-methanesulfonylphenyldiphenylsulfonium trifluoromethanesulfonate, 4-methanesulfonylphenyldiphenylsulfonium nonafluoro-n-butanesulfonate, 4-methanesulfonylphenyldiphenylsulfonium perfluoro-n-octanesulfonate, and 4-methanesulfonylphenyldiphenylsulfonium 2-(bicyclo[2.2.1]heptan-2-yl)-1,1,2,2-tetrafluoroethanesulfonate, diphenyliodonium trifluoromethanesulfonate, diphenyliodonium nonafluoro-n-butanesulfonate, diphenyliodonium perfluoro-n-octanesulfonate, diphenyliodonium 2-(bicyclo[2.2.1]heptan-2-yl)-1,1,2,2-tetrafluoroethanesulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium 2-(bicyclo[2.2.1]heptan-2-yl)-1,1,2,2-tetrafluoroethanesulfonate, 1-(4-n-butoxynaphthalen-1-yl)tetrahydrothiophenium trifluoromethanesulfonate, 1-(4-n-butoxynaphthalen-1-yl) tetrahydrothiophenium nonafluoro-n-butanesulfonate, 1-(4-n-butoxynaphthalen-1-yl)tetrahydrothiophenium perfluoro-n-octanesulfonate, 1-(4-n-butoxynaphthalen-1-yl) tetrahydrothiophenium 2-(bicyclo[2.2.1]heptan-2-yl)-1,1,2,2-tetrafluoroethanesulfonate, 1-(6-n-butoxynaphthalen-2-yl) tetrahydrothiophenium trifluoromethanesulfonate, 1-(6-n-butoxynaphthalen-2-yl)tetrahydrothiophenium nonafluoro-n-butanesulfonate, 1-(6-n-butoxynaphthalen-2-yl) tetrahydrothiophenium perfluoro-n-octanesulfonate, 1-(6-n-butoxynaphthalen-2-yl)tetrahydrothiophenium 2-(bicyclo [2.2.1]heptan-2-yl)-1,1,2,2-tetrafluoroethanesulfonate, 1-(3, 5-dimethyl-4-hydroxyphenyl)tetrahydrothiophenium trifluoromethanesulfonate, 1-(3,5-dimethyl-4-hydroxyphenyl)tetrahydrothiophenium nonafluoro-n-butanesulfonate, 1-(3,5-dimethyl-4-hydroxyphenyl)tetrahydrothiophenium perfluoro-n-octanesulfonate, 1-(3,5-dimethyl-4-hydroxyphenyl)tetrahydrothiophenium 2-(bicyclo[2.2.1]heptan-2-yl)-1,1,2,2-tetrafluoroethanesulfonate N-(trifluoromethanesulfonyloxy)bicyclo[2.2.1]hept-5-ene-2,3-dicarboximide, N-(nonafluoro-n-butanesulfonyloxy)bicyclo[2.2.1]hept-5-ene-2,3-dicarboxylmide, N-(perfluoro-n-octanesulfonyloxy)bicyclo[2.2.1]hept-5-ene-2,3-dicarboxylmide, N-[2-(bicyclo[2.2.1]heptan-2-yl)-1,1,2,2-tetrafluoroethanesulfonyloxy]bicyclo[2.2.1]hept-5-ene-2,3-dicarboxylmide, N-[2-(tetracyclo[4.4.0.12,5.17,10]dodecan-3-yl)-1,1-difluoroethanesulfonyloxy]bicyclo[2.2.1]hept-5-ene-2,3-dicarboxylmide, 1,3-dioxoisoindolin-2-yl trifluoromethanesulfonate, 1,3-dioxoisoindolin-2-yl nonafluoro-n-butane sulfonate, 1,3-dioxoisoindolin-2-yl perfluoro-n-octane sulfonate, 3-dioxoisoindolin-2-yl 2-(bicyclo[2.2.1]heptan-2-yl)-1,1,2,2-tetrafluoroethanesulfonate, 3-dioxoisoindolin-2-yl N-[2-(tetracyclo[4.4.0.12,5.17,10]dodecan-3-yl)-1,1-difluoroethanesulfonate, 1,3-dioxo-1H-benzo[de]isoquinolin-2(3H)-yl trifluoromethanesulfonate, 1,3-dioxo-1H-benzo[de]isoquinolin-2(3H)-yl nonafluoro-n-butane sulfonate, 1,3-dioxo-1H-benzo[de]isoquinolin-2(3H)-yl perfluoro-n-octanesulfonate, 1,3-dioxo-1H-benzo[de]isoquinolin-2(3H)-yl 2-(bicyclo[2.2.1]heptan-2-yl)-1,1,2,2-tetrafluoroethanesulfonate, or 1,3-dioxo-1H-benzo[de]isoquinolin-2(3H)-yl N-[2-(tetracyclo[4.4.0.12,5.17,10]dodecan-3-yl)-1,1-difluoroethanesulfonate, (E)-2-(4-methoxystyryl)-4,6-bis(trichloromethyl)-1,3,5-triazine, 2-(Methoxyphenyl)-4,6-bis-(trichloromethyl)-s-triazine, 2-[2-(Furan-2-yl)ethenyl]-4,6-bis(trichloromethyl)-s-triazine, 2-[2-(5-methylfuran-2-yl]ethenyl)-4,6-bis(trichloromethyl)-s-triazine, 2-[2-(3,4-Dimethoxyphenyl)ethenyl]-4,6-bis(trichloromethyl)-s-triazine, equivalents thereof or combinations thereof. In some cases, photoacid generators capable of generating perfluoroalkanesulfonic acid having a high acid strength are used as the PAG in the formulations of the present disclosure. Such photoacid generators include, but are not limited to, photoacid generators capable of generating partially fluorinated alkane sulfonic acids, fully fluorinated alkane sulfonic acids, perfluorohexanesulfonic acid, perfluorooctanesulfonic acid, perfluoro-4-ethylcyclohexanesulfonic acid, perfluoroalkyl ether sulfonic acids, and perfluorobutanesulfonic acid. Additional examples of photoacid generators are described in U.S. Patent Pub. No. 20200384436 and U.S. Patent Pub. No. 20210017127, the contents of which are herein incorporated by reference in their entireties.

In some embodiments, a photoresist composition can form a micro or nanopattern used in lithography process for manufacturing a biomelcular array. In some embodiments, the lithography process uses a substrate material such as a wafer, e.g., a silicon-based wafer. In some embodiments, a thin photoresist layer is formed on a substrate, and then the substrate is optionally baked to fix the photoresist layer on the substrate. In some embodiments, the photoresist layer on the substrate is exposed to radiation. The exposed photoresist layer can be treated with a developing solution, and by dissolving and removing the exposed area of the photoresist layer, a micro or nanopattern is formed. In some embodiments, a photolithography process disclosed herein may comprise forming a photoresist layer on a substrate using a photoresist composition; selectively exposing the photoresist layer; and developing the exposed photoresist layer. In some embodiments, a photolithography process disclosed herein comprises coating a photoresist composition on a substrate and drying (soft baking) the coated substrate. In some embodiments, a photolithography process disclosed herein comprises coating with a spin coater, a bar coater, a blade coater, a curtain coater, a screen printer or the like, and/or a spray coater or the like, and any method capable of coating a photoresist composition may be used. Drying (soft baking) of the substrate may be preformed under a suitable condition and may comprise, for example, an oven, a hot plate, vacuum drying and the like, but is not limited thereto. When going through the drying, a solvent is removed from the photoresist composition, increasing adhesive strength between the wafer and the photosensitive resin layer, and the photoresist layer may be secured on the substrate. In some embodiments, the selectively exposing of the photoresist layer is performed by aligning a mask on the photoresist, and exposing an area of the photoresist layer not covered by the mask to ultraviolet rays. The mask may be in contact with the photoresist layer, or may also be aligned at a certain distance from the photoresist layer. In some embodiments, a light source irradiated as a light irradiation means may comprise electromagnetic waves, extreme ultraviolet rays (EUV), from ultraviolet rays to visible rays, an electron beam, X-rays, laser rays and the like. Known means such as a high pressure mercury lamp, a xenon lamp, a carbon arc lamp, a halogen lamp, a cold cathode tube for a copier, an LED and a semiconductor laser may be used. In some embodiments, the selectively exposing of the photoresist layer may further comprise heating (post-exposure baking) the exposed photoresist layer after the exposure. In some embodiments, developing of the exposed photoresist layer comprises removing the exposed portion in the photoresist layer by immersing in a developing solution. Any photoresist developing methods known in the art may be used and are not limited to a rotary spray method, a paddle method, or an immersion method accompanying ultrasonic treatment. Examples of the developing solution may comprise alkali metal or alkaline earth metal hydroxides, carbonates, hydrogen carbonates, an aqueous basic solution such as an ammonia water quaternary ammonium salt may be used. For instance, an aqueous ammonia quaternary ammonium solution such as an aqueous tetramethyl ammonium solution may be used.

In some embodiments, the photoresist further comprises an acid scavenger. In some embodiments, the photoresist in the first and the second region comprises the same acid scavenger. In some embodiments, the photoresist in the first and the second region comprises different acid scavengers. In some embodiments, an acid scavenger acts to neutralize, adsorb and/or buffer acids, and may comprise a base or alkaline compound. In some embodiments, acid scavengers act to reduce the amount or concentration of protons or protonated water. In some embodiments, an acid scavenger acts to neutralize, diminish, or buffer acid produced by a photoacid generator. In some embodiments, an acid scavenger exhibits little or no stratification over time or following exposure to heat. In some embodiments, acid scavengers may be further subdivided into "organic bases" and "polymeric bases." A polymeric base is an acid scavenger (e.g., basic unit) attached to a longer polymeric unit. A polymer is typically composed of a number of coupled or linked monomers. The monomers can be the same (to form a homopolymer) or different (to form a copolymer). In a polymeric base, at least some of the monomers act as acid scavengers. An organic base is a base which is joined to or part of a non-polymeric unit. Non-limiting examples of organic bases include, without limitation, amine compounds (e.g., primary, secondary and tertiary amines). Generally any type of acid scavenger, defined here as a traditional Lewis Base, an electron pair donor, can be used in accordance with the present disclosure. The acid scavenger may be a tertiary aliphatic amine or a hindered amine. Examples of the acid scavenger include, but are not limited to 2,2,6,6-tetramethyl-4-piperidyl stearate, 1,2,2,6,6-pentamethyl-4-piperidyl stearate, 2,2,6,6-tetramethyl-4-piperidyl benzoate, bis(2,2,6,6-tetramethyl-4-piperidyl) sebacate, bis(1,2,2,6,6-tetramethyl-4-piperidyl) sebacate, bis(1-octoxy-2,2,6,6-tetramethyl-4-piperidyl)sebacate, tetrakis(2,2,6,6-tetramethyl-4-piperidyl)-1,2,3,4-butanetetracarboxylate, tetrakis(1,2,2,6,6-pentamethyl-4-piperidyl)-1,2,3,4-butanetetracarboxylate, bis(2,2,6,6-tetramethyl-4-piperidyl) di(tridecyl)-1,2,3,4-butanetetracarboxylate, bis(1,2,2,6,6-pentamethyl-4-piperidyl) di(tridecyl)-1,2,3,4-butanetetracarboxylate, bis(1,2,2,4,4-pentamethyl-4-piperidyl)-2-butyl-2-(3,5-di-t-4-hydroxy-benzyl)malonate, a polycondensate of 1-(2-hydroxyethyl)-2,2,6,6-tetramethyl-4-piperidinol and diethyl succinate, a polycondensate of 1,6-bis(2,2,6,6-tetramethyl-4-piperidylamino)hexane and 2,4-dichloro-6-morpholino-s-triazine, a polycondensate of 1,6-bis(2,2,6,6-tetramethyl-4-piperidylamino)hexane and 2,4-dichloro-6-t-octylamino-s-triazine, 1,5,8,12-tetrakis[2,4-bis(N-butyl-N-(2,2,6,6-tetramethyl-4-piperidyl)amino)-s-triazin-6-yl]-1,5,8,12-tetraazadodecane, 1,5,8,12-tetrakis[2,4-bis(N-butyl-N-(1,2,2,6,6-pentamethyl-4-piperidyl)amino)-s-triazin-6-yl]-1,5,8-12-tetraazadodecane, 1,6,11-tris[2,4-bis(N-butyl-N-(2,2,6,6-tetramethyl-4-piperidyl)amino)-s-triazin-6-yl]aminoundecane, and 1,6,11-tris[2,4-bis(N-butyl-N-(1,2,2,6,6-pentamethyl-4-piperidyl)amino)-s-triazin-6-yl]aminoundecane.

In some embodiments, the photoresist comprises a quencher, such as a base quencher. The quencher that may be used in the photoresist composition may comprise a weak base that scavenges trace acids, while not having an excessive impact on the performance of the positive photoresist. Illustrative examples of quenchers that can be employed include, but are not limited to: aliphatic amines, aromatic amines, carboxylates, hydroxides, or combinations thereof and the like. Base quenchers may be used in photoresist formulations to improve performance by quenching reactions of photoacids that diffuse into unexposed regions. Base quenchers may comprise aliphatic amines, aromatic amines, carboxylates, hydroxides, or combinations thereof. Examples of base quenchers include but are not limited to, trioctylamine, 1,8-diazabicyclo[5.4.0]undec-7-ene (DBU), 1-piperidineethanol (1PE), tetrabutylammonium hydroxide (TBAH), dimethylamino pyridine, 7-diethylamino-4-methyl coumarin (Coumarin 1), tertiary amines, sterically hindered diamine and guanidine bases such as 1,8-bis(dimethylamino)naphthalene (PROTON SPONGE), berberine, or polymeric amines such as in the PLURONIC or TETRONIC series commercially available from BASF. In some embodiments, the photoresist in the first and the second region comprises the same base quencher. In some embodiments, the photoresist in the first and the second region comprises different base quenchers.

In some embodiments, the photoresist further comprises a photosensitizer. A photosensitizer is a molecule that produces a chemical change in another molecule in a photochemical process. Photosensitizers are commonly used in polymer chemistry in reactions such as photopolymerization, photocrosslinking, and photodegradation. Photosensitizers generally act by absorbing ultraviolet or visible region of electromagnetic radiation and transferring it to adjacent molecules. In some embodiments, photosensitizer shifts the photo sensitivity to a longer wavelength of electromagnetic radiation. The sensitizer, also called a photosensitizer, is capable of activating the photoacid generator (PAG) at, for example, a longer wavelength of light in accordance with an aspect of the present disclosure. In some embodiments, the concentration of the sensitizer is greater than that of the PAG, such as 1.1 times to 5 times greater, for example, 1.1 times to 3 times greater the concentration of PAG. Examples of photosensitizer may include anthracene, N-alkyl carbazole, benzo[a]phenoxazine, and thioxanthone compounds. Exemplary sensitizers suitable for use in the methods disclosed herein include but are not limited to, isopropylthioxanthone (ITX), and 10H-phenoxazine (PhX). In some embodiments, the photoresist in the first and the second region comprises the same photosensitizer. In some embodiments, the photoresist in the first and the second region comprises different photosensitizers. Additional examples of photosensitizers include anthracenes {anthracene, 9,10-dibutoxyanthracene, 9,10-dimethoxyanthracene, 2-ethyl-9,10-dimethoxyanthracene, 2-tert-butyl-9,10-dimethoxyanthracene, 2,3-dimethyl-9,10-dimethoxyanthracene, 9-methoxy-10-methylanthracene, 9,10-diethoxyanthracene, 2-ethyl-9,10-diethoxyanthracene, 2-tert-butyl-9,10-diethoxyanthracene, 2,3-dimethyl-9,10-diethoxyanthracene, 9-ethoxy-10-methylanthracene, 9,10-dipropoxyanthracene, 2-ethyl-9,10-dipropoxyanthracene, 2-tert-butyl-9,10-dipropoxyanthracene, 2,3-dimethyl-9,10-dipropoxyanthracene, 9-isopropoxy-10-methylanthracene, 9,10-dibenzyloxyanthracene, 2-ethyl-9,10-dibenzyloxyanthracene, 2-tert-9,10-dibenzyloxyanthracene, 2,3-dimethyl-9,10-dibenzyloxyanthracene, 9-benzyloxy-10-methylanthracene, 9,10-di-α-methylbenzyloxyanthracene, 2-ethyl-9,10-di-α-methylbenzyloxyanthracene, 2-tert-9,10-di-α-methylbenzyloxyanthracene, 2,3-dimethyl-9,10-di-α-methylbenzyloxyanthracene, 9-(α-methylbenzyloxy)-10-methylanthracene, 9,10-diphenylanthracene, 9-methoxyanthracene, 9-ethoxyanthracene, 9-methylanthracene, 9-bromoanthracene, 9-methylthioanthracene, 9-ethylthioanthracene, and the like}; pyrene; 1,2-benzanthracene; perylene; tetracene; coronene; thioxanthones {thioxanthone, 2-methylthioxanthone, 2-ethylthioxanthone, 2-chlorothioxanthone, 2-isopropylthioxanthone, 2,4-diethylthioxanthone, and the like}; phenothiazine; xanthone; naphthalenes {1-naphthol, 2-naphthol, 1-methoxynaphthalene, 2-methoxynaphthalene, 1,4-dihydroxynaphthalene, 1,5-dihydroxynaphthalene, 1,6-dihydroxynaphthalene, 2,7-dihydroxynaphthalene, 2,7-dimethoxynaphthalene, 1,1'-thiobis(2-naphthol), 1,1'-bis-(2-naphthol), 4-methoxy-1-naphthol, and the like}; ketones {dimethoxyacetophenone, diethoxyacetophenone, 2-hydroxy-2-methyl-1-phenylpropan-1-one, 4'-isopropyl-2-hydroxy-2-methylpropiophenone, 2-hydroxymethyl-2-methylpropiophenone, 2,2-dimethoxy-1,2-diphenylethan-1-one, p-dimethylaminoacetophenone, p-tert-butyldichloroacetophenone, p-tert-butyltrichloroacetophenone, p-azidobenzalacetophenone, 1-hydroxycyclohexyl phenyl ketone, benzoin, benzoin methyl ether, benzoin ethyl ether, benzoin isopropyl ether, benzoin n-dibutyl ether, benzoin isobutyl ether, 1-[4-(2-hydroxyethoxy)phenyl]-2-hydroxy-2-methyl-1-propan-1-one, benzophenone, methyl o-benzoylbenzoate, Michler's ketone, 4,4'-bisdiethylaminobenzophenone, 4,4'-dichlorobenzophenone, 4-benzoyl-4'-methyldiphenylsulfide, and the like}, carbazoles {N-phenylcarbazole, N-ethylcarbazole, poly-N-vinylcarbazole, N-glycidylcarbazole, and the like}; chrysenes {1,4-dimethoxychrysene, 1,4-diethoxychrysene, 1,4-dipropoxychrysene, 1,4-dibenzyloxychrysene, 1,4-di-α-methylbenzyloxychrysene, and the like}; and phenanthrenes {9-hydroxyphenanthrene, 9-methoxyphenanthrene, 9-ethoxyphenanthrene, 9-benzyloxyphenanthrene, 9,10-dimethoxyphenanthrene, 9,10-diethoxyphenanthrene, 9,10-dipropoxyphenanthrene, 9,10-dibenzyloxyphenanthrene, 9,10-di-α-methylbenzyloxyphenanthrene, 9-hydroxy-10-methoxyphenanthrene, 9-hydroxy-10-ethoxyphenanthrene and are described in U.S. Patent Pub. No. 20200384436, the content of which is herein incorporated by reference in its entirety.

In some embodiments, the photoresist further comprises a matrix. The matrix generally refers to polymeric materials that may provide sufficient adhesion to the substrate when the photoresist formulation is applied to the top surface of the substrate, and may form a substantially uniform film when dissolved in a solvent and deposited on top of a substrate. Examples of a matrix may include, but are not limited to, polyester, polyimide, polyethylene naphthalate (PEN), polyvinyl chloride (PVC), polymethylmethacrylate (PMMA) and polycarbonate, or a combination thereof. The matrix may be chosen based on the wavelength of the radiation used for the generation of acid when using the photoresist formulation, the adhesion properties of the matrix to the top surface of the substrate, the compatibility of the matrix to other components of the formulation, and the ease of removable or degradation (if needed) after use. In some embodiments, the photoresist in the first and the second region comprises the same matrix. In some embodiments, the photoresist in the first and the second region comprises different matrices.

In some embodiments, the photoresist further comprises a surfactant. Surfactants may be used to improve coating uniformity, and may include ionic, non-ionic, monomeric, oligomeric, and polymeric species, or combinations thereof. Examples of possible surfactants include fluorine-containing surfactants such as the FLUORAD series available from 3M Company in St. Paul, Minn., and siloxane-containing surfactants such as the SILWET series available from Union Carbide Corporation in Danbury, Conn. In some embodiments, the photoresist in the first and the second region comprises the same surfactant. In some embodiments, the photoresist in the first and the second region comprises different surfactants.

In some embodiments, the photoresist further comprises a casting solvent. A casting solvent may be used so that the photoresist may be applied evenly on the substrate surface to provide a defect-free coating. Examples of suitable casting solvents may include ethers, glycol ethers, aromatic hydrocarbons, ketones (e.g., methyl ethyl ketone), esters, ethyl lactate, γ-butyrolactone, cyclohexanone, ethoxyethylpropionate (EEP), a combination of EEP and gamma-butyrolactone (GBL), propylene glycol ethyl ether acetate, amyl acetate, propylene glycol methyl ether acetate (PGMEA), and combinations thereof. In some embodiments, the photoresist in the first and the second region comprises the same casting solvent. In some embodiments, the photoresist in the first and the second region comprises different casting solvents. In some embodiments, the solvent may comprise but is not limited to acetone, methyl ethyl ketone, methyl isobutyl ketone, methyl cellosolve, ethyl cellosolve, tetrahydrofuran, 1,4-dioxane, ethylene glycol dimethyl ether, ethylene glycol diethyl ether, propylene glycol dimethyl ether, propylene glycol diethyl ether, diethylene glycol dimethyl ether, diethylene glycol diethyl ether, diethylene glycol methyl ethyl ether, chloroform, methylene chloride, 1,2-dichloroethane, 1,1,1-trichloroethane, 1,1,2-trichloroethane, 1,1,2-trichloroethene, hexane, heptane, octane, cyclohexane, benzene, toluene, xylene, methanol, ethanol, isopropanol, propanol, butanol, t-butanol, 2-ethoxypropanol, 2-methoxy-propanol, 3-methoxybutanol, cyclohexanone, cyclopentanone, propylene glycol methyl ether acetate, propylene glycol ethyl ether acetate, 3-methoxybutyl acetate, ethyl 3-ethoxypropionate, ethyl cellosolve acetate, methyl cellosolve acetate, butyl acetate, propylene glycol monomethyl ether, or dipropylene glycol monomethyl ether, or any combination thereof. In some embodiments, the solvent may comprise any one or more of those selected from the group consisting of ketones such as γ-butyrolactone, 1,3-dimethyl-imidazolidinone, methyl ethyl ketone, cyclohexanone, cyclopentanone and 4-hydroxy-4-methyl-2-pentanone; aromatic hydrocarbons such as toluene, xylene and tetramethylbenzene; glycol ethers (cellosolve) such as ethylene glycol monoethyl ether, ethylene glycol monomethyl ether, ethylene glycol monobutyl ether, diethylene glycol monoethyl ether, diethylene glycol monomethyl ether, diethylene glycol monobutyl ether, propylene glycol monomethyl ether, propylene glycol monoethyl ether, dipropylene glycol diethyl ether and triethylene glycol monoethyl ether; ethyl acetate, butyl acetate, ethylene glycol monoethyl ether acetate, ethylene glycol monobutyl ether acetate, diethylene glycol monoethyl ether acetate, dipropylene glycol monomethyl ether acetate, propylene glycol monomethyl ether acetate (PGMEA), ethanol, propanol, ethylene glycol, propylene glycol, carbitol, dimethylacetamide (DMAc), N,N-diethyl-acetamide, dimethylformamide (DMF), diethylformamide (DEF), N,N-dimethylacetamide (DMAc), N-methylpyrroli-done (NMP), N-ethylpyrrolidone (NEP), 1,3-dimethyl-2-imidazolidinone, N,N-dimethylmethoxyacetamide, dimethyl sulfoxide, pyridine, dimethyl sulfone, hexamethylphosphoramide, tetramethylurea, N-methyl-caprolactam, tetrahydrofuran, m-dioxane, p-dioxane, 1,2-dimethoxyethane, bis(2-methoxyethyl)ether, 1,2-bis(2-methoxyethoxy)ethane, bis[2-(2-methoxyethoxy)]ether, and mixtures thereof. Examples of solvents for use in photoresists are described in U.S. Patent Pub. No. 20200384436 and U.S. Patent Pub. No. 20210017127, the contents of which are herein incorporated by reference in their entireties.

In some embodiments of aspects provided herein, the photoresist composition comprises: the photoacid generator: about 1-10% (e.g., about 2-5%) by weight; the photosensitizer: about 1-10% (e.g., 2-5%) by weight; an acid scavenger: about 0.1-0.5% by weight; a matrix: about 2.5-4.5% by weight; and a solvent. In some embodiments of aspects provided herein, the photoresist composition comprises: the photoacid generator: about 2.5-4.5% by weight; the photo-sensitizer: about 2.5-4.5% by weight; the acid scavenger: about 0.15-0.35% by weight; the matrix: about 3.0-4.0% by weight; and the solvent. In some embodiments of aspects provided herein, weight percentage of the photosensitizer is substantially the same as weight percentage of the photoacid generator. In some embodiments of aspects provided herein, the weight percentage of the photosensitizer is the same as the weight percentage of the photoacid generator. Suitable photoresist compositions are described, for example, in U.S. Patent Pub. No. 20200384436, the content of which is herein incorporated by reference in its entirety.

Methods of applying photoresist to the substrate include, but are not limited to, dipping, spreading, spraying, or any combination thereof. In some embodiments, the photoresist is applied via spin coating, thereby forming a photoresist layer on the substrate.

In some embodiments, the photoresist is in direct contact with the oligonucleotides on the substrate. In some embodiments, the oligonucleotide molecules on the substrate are embedded in the photoresist. In some embodiments, the photoresist is not in direct contact with the oligonucleotides. In some embodiments, oligonucleotide molecules on the substrate are embedded in an underlayer that is underneath the photoresist. For example, oligonucleotide molecules on the substrate may be embedded in a soluble polymer underlayer (e.g., a soluble polyimide underlayer (XU-218)), and the photoresist forms a photoresist layer on top of the underlayer.

In some embodiments, the photoresist may be removed and re-applied. For example, the photoresist may be stripped from the substrate and/or the oligonucleotides ligated to the substrate. Removal of photoresist can be accomplished with various degrees of effectiveness. In some embodiments, the photoresist is completely removed from the substrate and/or the oligonucleotides ligated to the substrate before re-application. Methods of removing photoresist may include, but are not limited to, using organic solvent mixtures, using liquid chemicals, exposure to a plasma environment, or other dry techniques such as UV/03 exposure. In some embodiments, the photoresist is stripped using organic solvent. In some embodiments, the photoresist may be removed after each cycle of in situ array generation and re-applied prior to the next cycle of in situ array generation. In some embodiments, the photoresist removed, and the photoresist re-applied prior to the next cycle is the same photoresist. In some embodiments, the photoresist removed, and the photoresist re-applied prior to the next cycle are different photoresists.

In some embodiments, one or more photomasks also referred to herein as "masks" may be used to selectively remove photoresist on the substrate. The mask is designed in such a way that light exposed sites can be selected, and thus specify the coordinates on the array where each oligonucleotide can be attached. The process can be repeated, a new mask is applied activating different sets of sites and coupling different oligonucleotides, allowing arbitrary oligonucleotides to be constructed at each site. This process can be used to synthesize hundreds of thousands or millions of different oligonucleotides. In some embodiments, the substrate is irradiated through a patterned mask. The mask may be an opaque plate or film with transparent areas that allow light to shine through in a pre-defined pattern. After the irradiation step, the mask may be removed, translated to a different region on the substrate, or rotated. In some embodiments, a different photomasking pattern may be used in each barcoding round (e.g., a course mask having wide or large exposed areas, followed by a fine mask having small or narrow exposed areas). In some embodiments, the same photomasking pattern may be used in each barcoding round.

Using a series of photomasks, photoresist in desired regions of the substrate may be iteratively irradiated and subsequently removed.

The material of the photomask used herein may comprise silica with chrome in the opaque part. For example, the photomask may be transparent fused silica blanks covered with a pattern defined with a chrome metal absorbing film. The photomask may be used at various irradiation wavelengths, which include but are not limited to, 365 nm, 248 nm, and 193 nm. In some embodiments, the irradiation step herein can be performed for a duration of between about 1 minute and about 10 minutes, for example, for about 2 minutes, about 4 minutes, about 6 minutes, or about 8 minutes. In some embodiments, the irradiation can be performed at a total light dose of between about one and about ten $mW/mm^2$, for example, at about 2 $mW/mm^2$, about 4 $mW/mm^2$, about 6 $mW/mm^2$, or about 8 $mW/mm^2$. In some embodiments, the irradiation can be performed at a total light dose of between about one and about ten $mW/mm^2$ and for a duration of between about 1 minute and about 10 minutes.

B. Molecular Arrays

In some aspects, the methods provided herein comprise attaching oligonucleotides (e.g. a barcode) to a substrate. Oligonucleotides may be attached to the substrate according to the methods set forth in U.S. Pat. Nos. 6,737,236, 7,259,258, 7,375,234, 7,309,593, 7,427,678, 5,610,287, 5,807,522, 5,837,860, and 5,472,881; U.S. Patent Application Publication Nos. 2008/0280773, 2011/0143967, and 2011/0059865; Shalon et al. (1996) Genome Research, 639-645; Rogers et al. (1999) Analytical Biochemistry 266, 23-30; Stimpson et al. (1995) Proc. Natl. Acad. Sci. USA 92, 6379-6383; Beattie et al. (1995) Clin. Chem. 45, 700-706; Lamture et al. (1994) Nucleic Acids Research 22, 2121-2125; Beier et al. (1999) Nucleic Acids Research 27, 1970-1977; Joos et al. (1997) Analytical Biochemistry 247, 96-101; Nikiforov et al. (1995) Analytical Biochemistry 227, 201-209; Timofeev et al. (1996) Nucleic Acids Research 24, 3142-3148; Chrisey et al. (1996) Nucleic Acids Research 24, 3031-3039; Guo et al. (1994) Nucleic Acids Research 22, 5456-5465; Running and Urdea (1990) Bio-Techniques 8, 276-279; Fahy et al. (1993) Nucleic Acids Research 21, 1819-1826; Zhang et al. (1991) 19, 3929-3933; and Rogers et al. (1997) Gene Therapy 4, 1387-1392. The entire contents of each of the foregoing documents are incorporated herein by reference.

In some embodiments, oligonucleotides may be immobilized by spotting (e.g., DNA printing) on a substrate with reactive surface chemistry, such as a polymer (e.g., a hydrophilic polymer) containing epoxy reactive groups. In some embodiments, the polymer comprises a passivating polymer. In some embodiments, the polymer comprises a photoreactive group for attachment to the substrate (such as a glass slide). In some embodiments, the oligonucleotides may be immobilized in a DNA printing buffer, optionally wherein the printing buffer comprises a surfactant such as sarcosyl (e.g., a buffer containing sodium phosphate and about 0.06% sarcosyl). In some embodiments, after immobilization of the oligonucleotides, one or more wash and/or blocking steps are performed. Blocking steps can comprise contacting the substrate with a solution that deactivates or blocks unreacted functional groups on the substrate surface. In one example, the blocking buffer can comprise ethanolamine (e.g., to deactivate epoxy silane or other epoxy reactive functional groups).

Arrays can be prepared by a variety of methods. In some embodiments, arrays are prepared through the synthesis (e.g., in situ synthesis) of oligonucleotides on the array, or by jet printing or lithography. For example, light-directed synthesis of high-density DNA oligonucleotides can be achieved by photolithography or solid-phase DNA synthesis. To implement photolithographic synthesis, synthetic linkers modified with photochemical protecting groups can be attached to a substrate and the photochemical protecting groups can be modified using a photolithographic mask (applied to specific areas of the substrate) and light, thereby producing an array having localized photo-deprotection. Many of these methods are known in the art, and are described e.g., in Miller et al., "Basic concepts of microarrays and potential applications in clinical microbiology." Clinical microbiology reviews 22.4 (2009): 611-633; US201314111482A; U.S. Pat. No. 9,593,365B2; US2019203275; and WO2018091676, the contents of each of which are incorporated herein by reference in their entirety.

In some embodiments, a substrate comprising an array of molecules is provided, e.g., in the form of a lawn of polymers (e.g., oligonucleotides), or polymers on the substrate in a pre-determined pattern. Examples of polymers on an array may include, but are not limited to, nucleic acids, peptides, phospholipids, polysaccharides, heteromacromolecules in which a known drug is covalently bound to any of the above, polyurethanes, polyesters, polycarbonates, polyureas, polyamides, polyethyleneimines, polyarylene sulfides, polysiloxanes, polyimides, and polyacetates. The molecules occupying different features of an array typically differ from one another, although some redundancy in which the same polymer occupies multiple features can be useful as a control. For example, in a nucleic acid array, the nucleic acid molecules within the same feature are typically the same, whereas nucleic acid molecules occupying different features are mostly different from one another.

In some examples, the molecules on the array may be nucleic acids. The nucleic acid molecule can be single-stranded or double-stranded. Nucleic acid molecules on an array may be DNA or RNA. The DNA may be single-stranded or double-stranded. The DNA may include, but are not limited to, mitochondrial DNA, cell-free DNA, complementary DNA (cDNA), genomic DNA, plasmid DNA, cosmid DNA, bacterial artificial chromosome (BAC), or yeast artificial chromosome (YAC). The RNA may include, but are not limited to, mRNAs, tRNAs, snRNAs, rRNAs, retroviruses, small non-coding RNAs, microRNAs, polysomal RNAs, pre-mRNAs, intronic RNA, viral RNA, cell free RNA and fragments thereof. The non-coding RNA, or ncRNA can include snoRNAs, microRNAs, siRNAs, piRNAs and long non-coding RNAs (lncRNAs).

In some embodiments, the molecules on an array comprise oligonucleotide barcodes. A barcode sequence can be of varied length. In some embodiments, the barcode sequence is about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 30, about 35, about 40, about 45, about 50, about 55, about 60, about 65, or about 70 nucleotides in length. In some embodiments, the barcode sequence is between about 4 and about 25 nucleotides in length. In some embodiments, the barcode sequences is between about 10 and about 50 nucleotides in length. The nucleotides can be completely contiguous, i.e., in a single stretch of adjacent nucleotides, or they can be separated into two or more separate subsequences that are separated by 1 or more nucleotides. In some embodiments, the barcode sequence can be about 4, about 5, about 6, about 7, about 8, about 9, about 10, about 11, about 12, about 13, about 14, about 15, about 16, about 17, about 18, about 19, about 20, about 21, about 22, about 23, about 24, about 25 nucleotides or longer. In some embodiments, the barcode sequence can be at least about 4, about 5, about 6, about 7, about 8, about 9, about 10, about 11, about 12, about 13, about 14, about 15, about 16, about 17, about 18, about 19, about 20, about 21, about 22, about 23, about 24, about 25 nucleotides or longer. In some embodiments, the barcode sequence can be at most about 4, about 5, about 6, about 7, about 8, about 9, about 10, about 11, about 12, about 13, about 14, about 15, about 16, about 17, about 18, about 19, about 20, about 21, about 22, about 23, about 24, about 25 nucleotides or shorter.

The oligonucleotide can include one or more (e.g., two or more, three or more, four or more, five or more) Unique Molecular Identifiers (UMIs). A unique molecular identifier is a contiguous nucleic acid segment or two or more non-contiguous nucleic acid segments that function as a label or identifier for a particular analyte, or for a capture probe that binds a particular analyte (e.g., via the capture domain).

A UMI can be unique. A UMI can include one or more specific polynucleotides sequences, one or more random nucleic acid and/or amino acid sequences, and/or one or more synthetic nucleic acid and/or amino acid sequences.

In some embodiments, the UMI is a nucleic acid sequence that does not substantially hybridize to analyte nucleic acid molecules in a biological sample. In some embodiments, the UMI has less than 90% sequence identity (e.g., less than 80%, 70%, 60%, 50%, or less than 40% sequence identity) to the nucleic acid sequences across a substantial part (e.g., 80% or more) of the nucleic acid molecules in the biological sample.

The UMI can include from about 6 to about 20 or more nucleotides within the sequence of capture probes, e.g., barcoded oligonucleotides in an array generated using a method disclosed herein. In some embodiments, the length of a UMI sequence can be about 6, 7, 8, 9, 10, 11, 12, 13, 14, 15, 16, 17, 18, 19, 20 nucleotides or longer. In some embodiments, the length of a UMI sequence can be at least about 6, 7, 8, 9, 10, 11, 12, 13, 14, 15, 16, 17, 18, 19, 20 nucleotides or longer. In some embodiments, the length of a UMI sequence is at most about 6, 7, 8, 9, 10, 11, 12, 13, 14, 15, 16, 17, 18, 19, 20 nucleotides or shorter. These nucleotides can be contiguous, i.e., in a single stretch of adjacent nucleotides, or they can be separated into two or more separate subsequences that are separated by 1 or more nucleotides. Separated UMI subsequences can be from about 4 to about 16 nucleotides in length. In some embodiments, the UMI subsequence can be about 4, 5, 6, 7, 8, 9, 10, 11, 12, 13, 14, 15, 16 nucleotides or longer. In some embodiments, the UMI subsequence can be at least about 4, 5, 6, 7, 8, 9, 10, 11, 12, 13, 14, 15, 16 nucleotides or longer. In some embodiments, the UMI subsequence can be at most about 4, 5, 6, 7, 8, 9, 10, 11, 12, 13, 14, 15, 16 nucleotides or shorter.

In some embodiments, a UMI is attached to other parts of the oligonucleotide in a reversible or irreversible manner. In some embodiments, a UMI is added to, for example, a fragment of a DNA or RNA sample before sequencing of the analyte. In some embodiments, a UMI allows for identification and/or quantification of individual sequencing-reads. In some embodiments, a UMI is used as a fluorescent barcode for which fluorescently labeled oligonucleotide probes hybridize to the UMI.

In some embodiments, a method provided herein further comprises a step of providing the substrate. A wide variety of different substrates can be used for the foregoing purposes. In general, a substrate can be any suitable support material. The substrate may comprise materials of one or more of the IUPAC Groups 4, 6, 11, 12, 13, 14, and 15 elements, plastic material, silicon dioxide, glass, fused silica, mica, ceramic, or metals deposited on the aforementioned substrates. Exemplary substrates include, but are not limited to, glass, modified and/or functionalized glass, hydrogels, films, membranes, plastics (including e.g., acrylics, polystyrene, copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, quartz, metals, inorganic glasses, optical fiber bundles, and polymers, such as polystyrene, cyclic olefin copolymers (COCs), cyclic olefin polymers (COPs), polypropylene, polyethylene and polycarbonate. In some embodiments, the substrate is a glass substrate.

A substrate can be of any desired shape. For example, a substrate can be typically a thin (e.g., sub-centimeter), flat shape (e.g., square, rectangle or a circle). In some embodiments, a substrate structure has rounded corners (e.g., for increased safety or robustness). In some embodiments, a substrate structure has one or more cut-off corners (e.g., for use with a slide clamp or cross-table). In some embodiments, where a substrate structure is flat, the substrate structure can be any appropriate type of support having a flat surface (e.g., a chip, wafer, die, or a slide such as a microscope slide).

In some embodiments, the surface of the substrate is coated. In some embodiments, the surface of the substrate is coated with a photoresist. In some embodiments, the method described herein comprises applying the photoresist to the substrate. In some embodiments, the substrate comprises a pattern of oligonucleotide molecules on the substrate prior to photoresist(s) being applied to the substrate. In some embodiments, the substrate does not comprise a pattern of oligonucleotide molecules on the substrate prior to photoresist(s) being applied to the substrate. In some embodiments where the substrate does not comprise oligonucleotide molecules prior to the application of photoresist(s), the substrate comprises a plurality of functional groups. In some embodiments, the plurality of functional groups of the substrate are not protected, for example, by photo-sensitive groups, moieties, or molecules. In some embodiments, the plurality of functional groups are aldehyde groups. In some embodiments, the plurality of functional groups of the substrate are click chemistry groups. The click chemistry group may be capable of various chemical reactions, which include but are not limited to, a nucleophilic addition reaction, a cyclopropane-tetrazine reaction, a strain-promoted azide-alkyne cycloaddition (SPAAC) reaction, an alkyne hydrothiolation reaction, an alkene hydrothiolation reaction, a strain-promoted alkyne-nitrone cycloaddition (SPANC) reaction, an inverse electron-demand Diels-Alder (IED-DA) reaction, a cyanobenzothiazole condensation reaction, an aldehyde/ketone condensation reaction, or a Cu(I)-catalyzed azide-alkyne cycloaddition (CuAAC) reaction. In some embodiments, the plurality of functional groups on the substrate react with functional groups in functionalized oligonucleotide molecules. In some embodiments, the functional groups in the functionalized oligonucleotide molecules are amino groups. In some embodiments, the functionalized oligonucleotide molecules are 5' amine-terminated.

In some embodiments, during the contact between the functionalized oligonucleotide molecules and the functional groups on the substrate, the substrate is heated to dryness. In some embodiments, after the contact between the functionalized oligonucleotide molecules and the functional groups on the substrate, the substrate is heated to dryness. In some embodiments according to any one of the methods described herein, the method further comprises blocking unreacted functional groups of the substrate. In some embodiments, the method comprises rendering the reaction between functional groups of the substrate and the functionalized oligonucleotide molecules irreversible. For example, the aldehyde groups of the substrate are reacted with 5' amino groups of the functionalized oligonucleotide molecules, and the substrate is contacted with a reagent to block unreacted aldehyde groups and render the reaction irreversible. In some embodiment, the reagent is a reductive agent. In some embodiment, the reagent is sodium borohydride.

Figure 7:
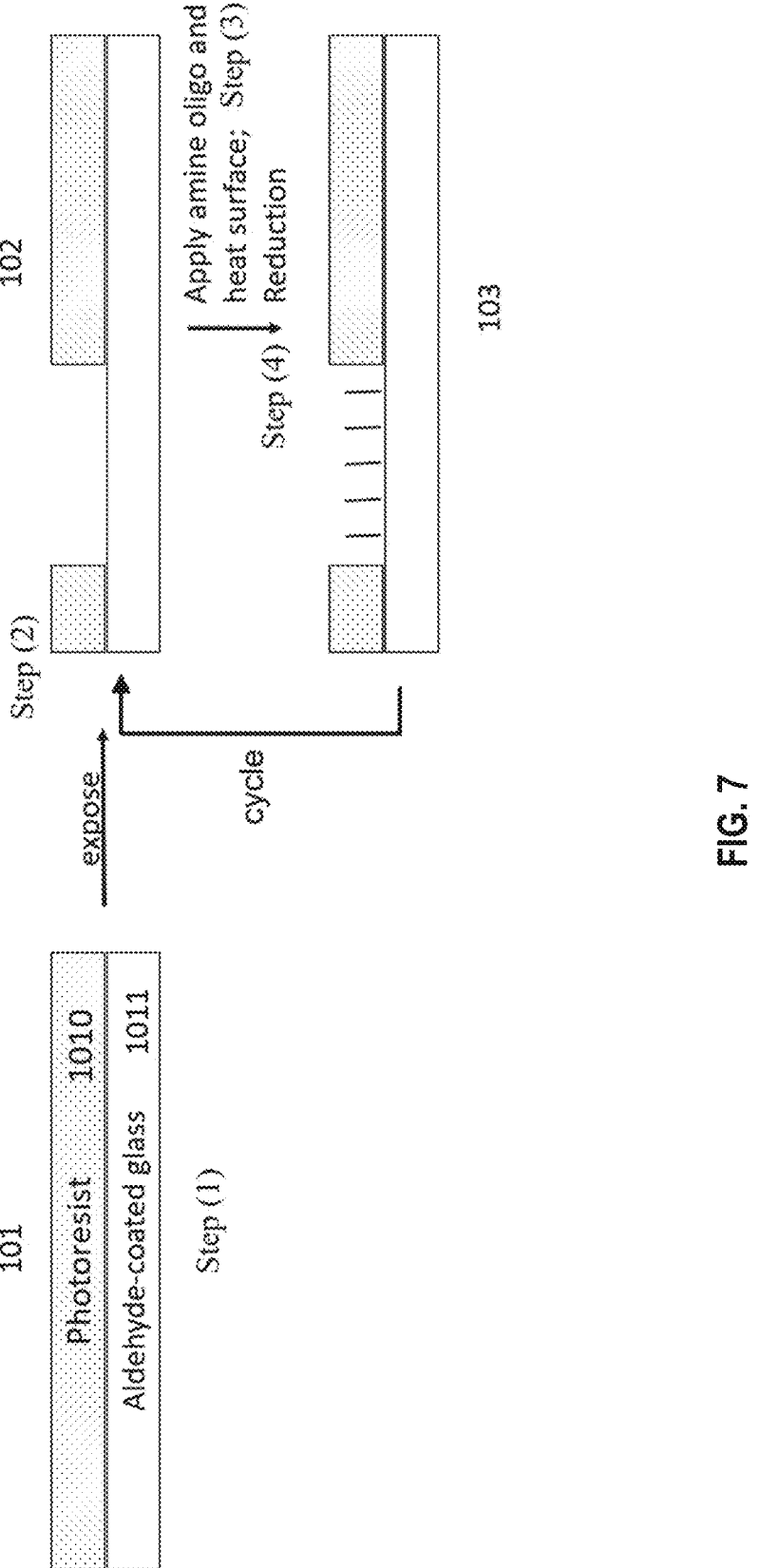
FIG. 7 shows an exemplary method for attaching oligonucleotides to a pre-determined location on an aldehyde-coated glass substrate using a photoresist.

In some examples as illustrated in FIG. 7, round 1 of the methods may comprise the following steps, wherein a cycle in round 1 comprises steps (2)-(4). In round 1, step (1) comprises covering a reactive surface 1011 (e.g., a substrate comprising aldehyde groups) using a photoresist 1010 to generate a coated substrate 101. Step (2) comprises selectively removing photoresist to unveil the reactive groups (e.g., aldehyde groups) on the surface to generate substrate 102. Step (3) comprises applying amine oligonucleotides over the substrate surface and heat up the surface; step (4) comprises irreversibly ligating oligonucleotides on the substrate surface and deactivation of unligated reactive groups (e.g., add sodium borohydride to reduce aldehyde groups to alcohols). In some embodiments, step (5) comprises repeating the cycle (steps (2)-(4)) for each feature without needing to re-apply photoresist.

Figure 8:
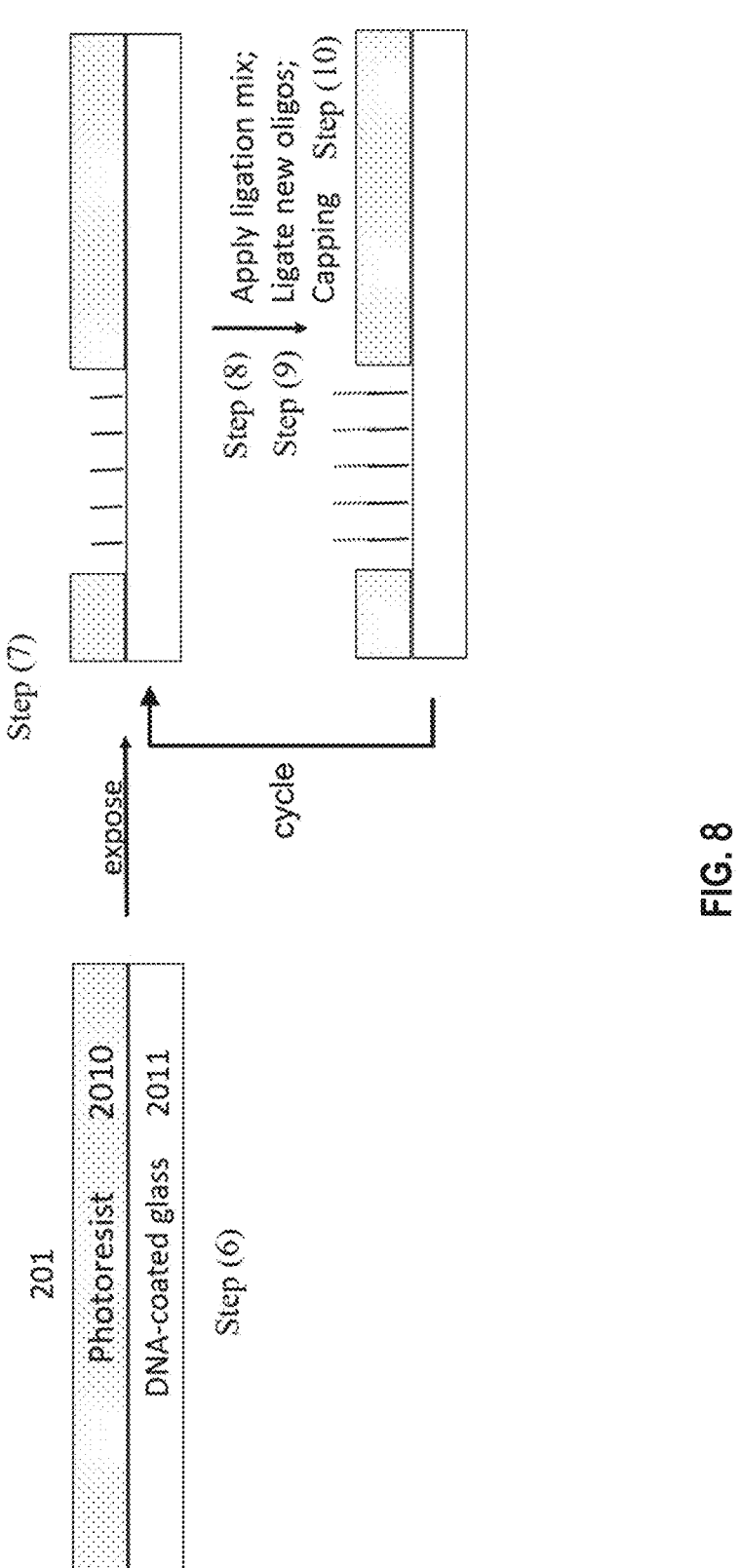
FIG. 8 shows an exemplary method for ligating oligonucleotides to a pre-determined location on a DNA-coated glass substrate using a photoresist.
Figure 9:
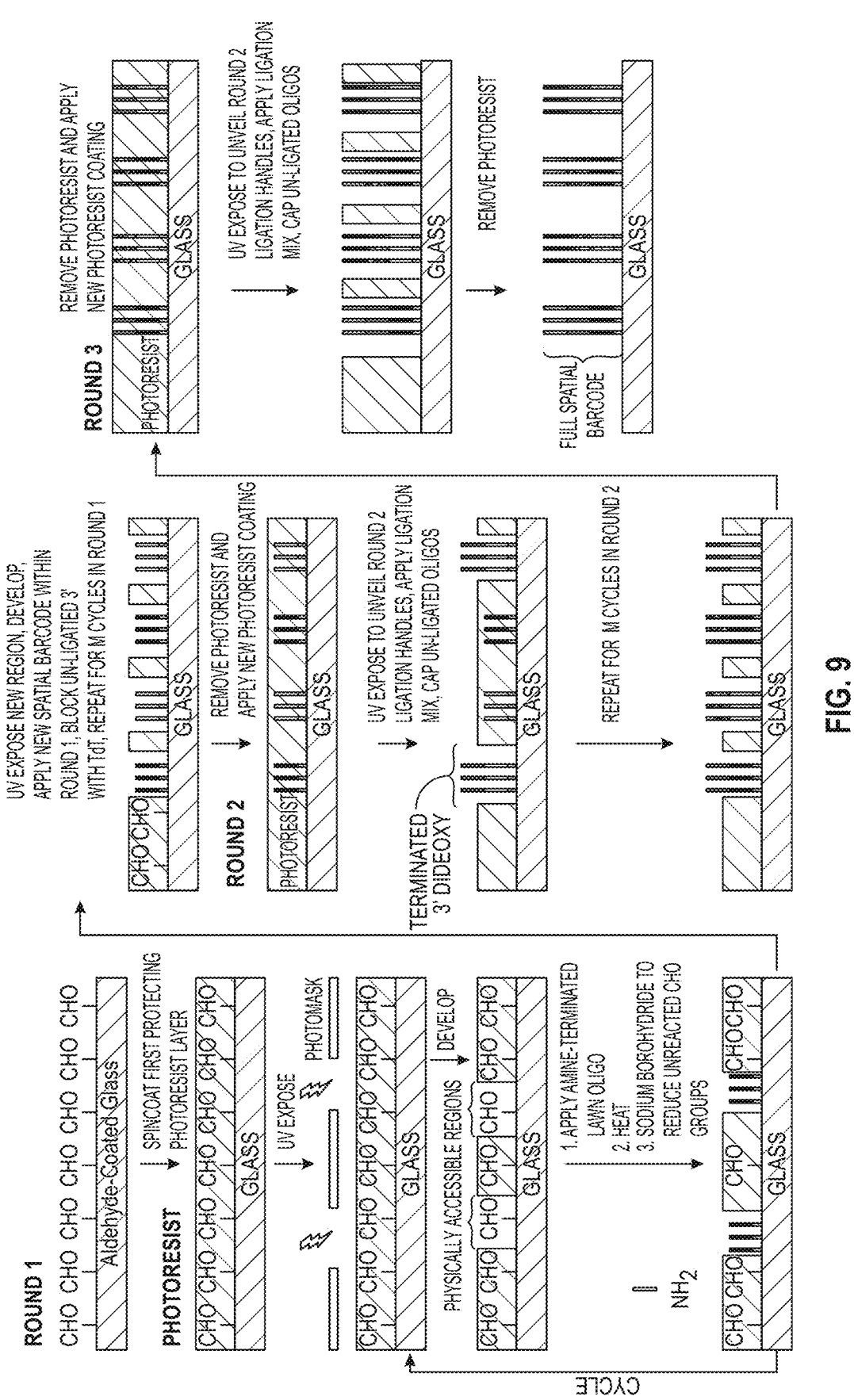
FIG. 9 shows an exemplary method for in situ array generation using photoresist from a functionalized substrate.

In some examples as illustrated in FIG. 8, round 2 of the methods may comprise the following steps, wherein a cycle in round 2 comprises steps (7)-(9) or optionally (7)-(10): step (6) remove remaining photoresist and re-apply photoresist 2010 to cover substrate with oligonucleotides ligated (2011) in round 1 to generate a coated substrate 201; step (7) selectively remove photoresist to unveil oligonucleotides ligated in round 1; step (8) apply ligation mixture comprising new oligonucleotides (e.g., second part of a barcode) to the oligonucleotides exposed in step (7); step (9) irreversibly ligate new oligonucleotides to the oligonucleotides ligated in round 1 (e.g., using splint ligation method); step (10) optionally cap oligonucleotides (e.g., with dideoxy NTP using terminal transferase). In some embodiments, step (11) may comprise repeating cycle (steps (7)-(9), or optionally steps (7)-(10), or a combination thereof) for each feature without needing to re-apply photoresist. In some examples, round 2 may be repeated optionally to create oligonucleotides of three or more barcode parts. Molecular arrays generated using methods shown in FIG. 7 or FIG. 8 may be subjected to further processing using a method disclosed herein, e.g., as shown in FIG. 1 or FIG. 9.

III. Hybridization/Ligation

The nucleotide barcode parts described herein may be linked via phosphodiester bonds. The nucleotide barcode parts may also be linked via non-natural oligonucleotide linkages such as methylphosphonate or phosphorothioate bonds, via non-natural biocompatible linkages such as click-chemistry, via enzymatic biosynthesis of nucleic acid polymers such as by polymerase or transcriptase, or a combination thereof. Ligation may be achieved using methods that include, but are not limited to, primer extension, hybridization ligation, enzymatic ligation, and chemical ligation. In some embodiments, the oligonucleotide comprising the barcode sequence is hybridized to a splint which is in turn hybridized to an oligonucleotide molecule in the unmasked region. The oligonucleotide comprising the barcode sequence may be further ligated to the oligonucleotide in the unmasked region to generate a barcoded oligonucleotide molecule.

In some cases, a primer extension or other amplification reaction may be used to synthesize an oligonucleotide on a substrate via a primer attached to the substrate. In such cases, a primer attached to the substrate may hybridize to a primer binding site of an oligonucleotide that also contains a template nucleotide sequence. The primer can then be extended by a primer extension reaction or other amplification reaction, and an oligonucleotide complementary to the template oligonucleotide can thereby be attached to the substrate.

In some embodiments, chemical ligation can be used to ligate two or more oligonucleotides. In some embodiments, chemical ligation involves the use of condensing reagents. In some embodiments, condensing reagents are utilized to activate a phosphate group. In some embodiments, condensing reagents may be one or more of 1-ethyl-3-(3-dimethyl-aminopropyl) carbodiimide (EDCI), cyanogen bromide, imidazole derivatives, and 1-hydroxybenzotriazole (HOAt). In some embodiments, functional group pairs selected from one or more of a nucleophilic group and an electrophilic group, or an alkyne and an azide group are used for chemical ligation. In some embodiments, chemical ligation of two or more oligonucleotides requires a template strand that is complementary to the oligonucleotides to be ligated (e.g., a splint). In some embodiments, the chemical ligation process is similar to oligonucleotide synthesis.

A splint is an oligonucleotide that, when hybridized to other polynucleotides, acts as a "splint" to position the polynucleotides next to one another so that they can be ligated together. In some embodiments, the splint is DNA or RNA. The splint can include a nucleotide sequence that is partially complimentary to nucleotide sequences from two or more different oligonucleotides. In some embodiments, the splint assists in ligating a "donor" oligonucleotide and an "acceptor" oligonucleotide. In general, an RNA ligase, a DNA ligase, or another other variety of ligase is used to ligate two nucleotide sequences together.

Splints have been described, for example, in US20150005200A1. A splint may be used for ligating two oligonucleotides. The sequence of a splint may be configured to be in part complementary to at least a portion of the first oligonucleotides that are attached to the substrate and in part complementary to at least a portion of the second oligonucleotides. In one case, the splint can hybridize to the second oligonucleotide via its complementary sequence; once hybridized, the second oligonucleotide or oligonucleotide segment of the splint can then be attached to the first oligonucleotide attached to the substrate via any suitable attachment mechanism, such as, for example, a ligation reaction. The splint complementary to both the first and second oligonucleotides can then be then denatured (or removed) with further processing. The method of attaching the second oligonucleotides to the first oligonucleotides can then be optionally repeated to ligate a third, and/or a fourth, and/or more parts of the barcode onto the array with the aid of splint(s). In some embodiments, the splint is between 6 and 50 nucleotides in length, e.g., between 6 and 45, 6 and 40, 6 and 35, 6 and 30, 6 and 25, or 6 and 20 nucleotides in length. In some embodiments, the splint is between 15 and 50, 15 and 45, 15 and 40, 15 and 35, 15 and 30, 15 and 30, or 15 and 25 nucleotides in length.

In some embodiments, the method for providing an array described herein comprises (a) irradiating a substrate comprising an unmasked first region and a masked second region, whereby a photoresist in the first region is degraded to render oligonucleotide molecules in the first region available for hybridization and/or ligation, whereas oligonucleotide molecules in the second region are protected by the photoresist in the second region from hybridization and/or ligation; and (b) contacting oligonucleotide molecules in the first region with a first splint and a first oligonucleotide comprising a first barcode sequence. In some embodiments, the first splint hybridizes to the first oligonucleotide and the oligonucleotide molecules in the first region. In some embodiments, the first oligonucleotide is not ligated to oligonucleotide molecules in the second region. In some embodiments, the hybridization region between the first splint and the oligonucleotide molecules is at least 3, 4, 5, 6, 7, 8, 9, 10 bp or more than 10 bp. In some embodiments, the hybridization region between the first splint and the first oligonucleotide is at least 3, 4, 5, 6, 7, 8, 9, 10 bp or more than 10 bp.

In some embodiments, the oligonucleotide is ligated using the splint as template without gap filling prior to the ligation. In some embodiments, the oligonucleotide is ligated using the splint as template with gap filling prior to the ligation. In some embodiments, hybridization to the first splint brings the terminal nucleotides of the first oligonucleotide and the oligonucleotide molecules immediately next to each other, and the ligation does not require gap-filling. In some embodiments, hybridization to the first splint brings the terminal nucleotides of the first oligonucleotide and the oligonucleotide molecules next to each other and separated by one or more nucleotides, and the ligation is preceded by gap-filling. In some embodiments, the splint is removed after the ligation.

In some embodiments according to the method for providing an array described herein, the photoresist is a first photoresist. In some embodiment, the first oligonucleotide is ligated to the oligonucleotide molecules in the first region to generate first extended oligonucleotide molecules. In some embodiments, the method further comprises the following steps: (c) applying a second photoresist to the substrate, optionally wherein the second photoresist is applied after the first photoresist is removed from the substrate; (d) irradiating the substrate while the first region is masked and the second region is unmasked, whereby the first or second photoresist in the second region is degraded to render oligonucleotide molecules in the second region available for hybridization and/or ligation, whereas the first extended oligonucleotide molecules in the first region are protected by the second photoresist in the first region from hybridization and/or ligation; and (c) contacting oligonucleotide molecules in the second region with a second splint and a second oligonucleotide comprising a second barcode sequence. In some embodiments, the second splint hybridizes to the second oligonucleotide and the oligonucleotide molecules in the second region. In some embodiments, the second oligonucleotide is ligated to the oligonucleotide molecules in the second region to generate second extended oligonucleotide molecules. In some embodiments, the second oligonucleotide is not ligated to the first extended oligonucleotide molecules in the first region. In some embodiments according to the methods described in the section, steps (a)-(b) are part of a first cycle, steps (d)-(e) are part of a second cycle, and steps (a)-(e) are part of a first round, and wherein the method comprises one or more additional rounds. In some embodiments, steps (a)-(e) are part of a first round, the first and second oligonucleotides are Round 1 oligonucleotides, the first and second barcode sequences are Round 1 barcode sequences. In some embodiments, the method further comprises: a') irradiating the substrate while the first region is unmasked and the second region is masked, whereby a photoresist in the first region is degraded to render the first extended oligonucleotide molecules in the first region available for hybridization and/or ligation, whereas the second extended oligonucleotide molecules in the second region are protected by the photoresist in the second region from hybridization and/or ligation; and (b') attaching a first Round 2 oligonucleotide comprising a first Round 2 barcode sequence to the first extended oligonucleotide molecules in the first region via hybridization and/or ligation, wherein the second extended oligonucleotide molecules in the second region do not receive the first Round 2 barcode sequence. In some embodiments wherein the photoresist is a first photoresist, and the first Round 2 oligonucleotide is ligated to the first extended oligonucleotide molecules in the first region to generate first further extended oligonucleotide molecules, the method further comprises: (c') applying a second photoresist to the substrate, optionally wherein the second photoresist is applied after the first photoresist is removed from the substrate; (d') irradiating the substrate while the first region is masked and the second region is unmasked, whereby the first or second photoresist in the second region is degraded to render the second extended oligonucleotide molecules in the second region available for hybridization and/or ligation, whereas the first further extended oligonucleotide molecules in the first region are protected by the second photoresist in the first region from hybridization and/or ligation; and (e') attaching a second Round 2 oligonucleotide comprising a second Round 2 barcode sequence to the second extended oligonucleotide molecules in the second region via hybridization and/or ligation, wherein the first further extended oligonucleotide molecules in the first region do not receive the second Round 2 barcode sequence. In some embodiments, the Round 1 barcode sequences are different from each other. In some embodiments, the Round 1 barcode sequences are different from the Round 2 barcode sequences.

Figure 3:
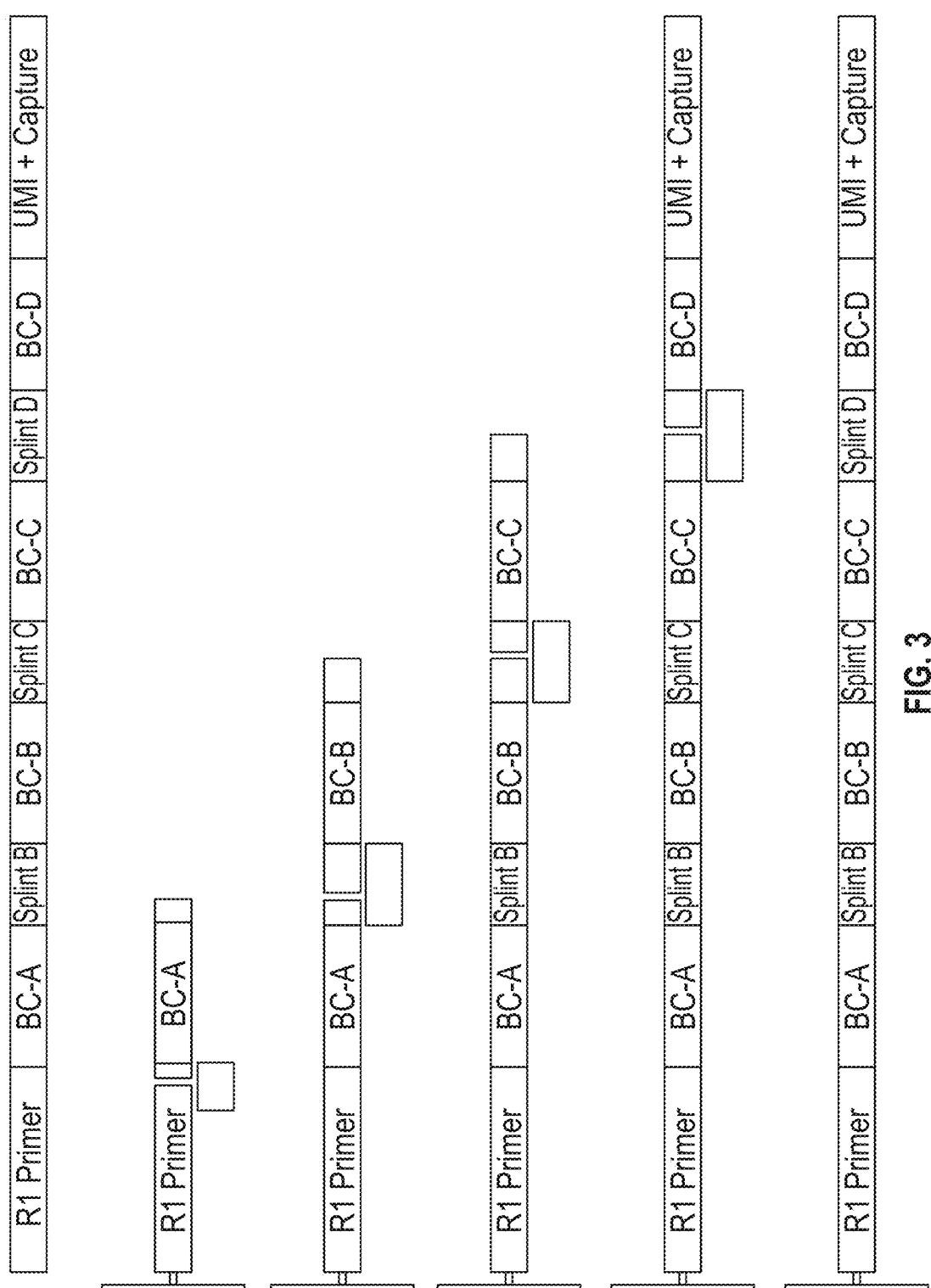
FIG. 3 shows an exemplary barcoded molecule generated using a method described herein.

In some aspects, provided herein is a method for construction of a hybridization complex or an array comprising nucleic acid molecules and complexes. FIG. 3 shows an exemplary oligonucleotide probe for capturing analytes which may be generated using a method disclosed herein comprising four rounds of hybridization and ligation.

In some embodiments, the oligonucleotide probe for capturing analytes may be generated from an existing array with a ligation strategy. In some embodiments, an array containing a plurality of oligonucleotides (e.g., in situ synthesized oligonucleotides) can be modified to generate a variety of oligonucleotide probes. The oligonucleotides can include various domains such as, spatial barcodes, UMIs, functional domains (e.g., sequencing handle), cleavage domains, and/or ligation handles.

A "spatial barcode" may comprise a contiguous nucleic acid segment or two or more non-contiguous nucleic acid segments that function as a label or identifier that conveys or is capable of conveying spatial information. In some embodiments, a capture probe includes a spatial barcode that possesses a spatial aspect, where the barcode is associated with a particular location within an array or a particular location on a substrate. A spatial barcode can be part of a capture probe on an array generated herein. A spatial barcode can also be a tag attached to an analyte (e.g., a nucleic acid molecule) or a combination of a tag in addition to an endogenous characteristic of the analyte (e.g., size of the analyte or end sequence(s)). A spatial barcode can be unique. In some embodiments where the spatial barcode is unique, the spatial barcode functions both as a spatial barcode and as a unique molecular identifier (UMI), associated with one particular capture probe. Spatial barcodes can have a variety of different formats. For example, spatial barcodes can include polynucleotide spatial barcodes; random nucleic acid and/or amino acid sequences; and synthetic nucleic acid and/or amino acid sequences. In some embodiments, a spatial barcode is attached to an analyte in a reversible or irreversible manner. In some embodiments, a spatial barcode is added to, for example, a fragment of a DNA or RNA sample before sequencing of the sample. In some embodiments, a spatial barcode allows for identification and/or quantification of individual sequencing-reads. In some embodiments, a spatial barcode is a used as a fluorescent barcode for which fluorescently labeled oligonucleotide probes hybridize to the spatial barcode.

In some embodiments, a spatial array is generated after ligating capture domains (e.g., poly(T) or gene specific capture domains) to the oligonucleotide molecule (e.g., generating capture oligonucleotides). The spatial array can be used with any of the spatial analysis methods described herein. For example, a biological sample (e.g., a tissue section) can be provided to the generated spatial array. In some embodiments, the biological sample is permeabilized. In some embodiments, the biological sample is permeabilized under conditions sufficient to allow one or more analytes present in the biological sample to interact with the capture probes of the spatial array. After capture of analytes from the biological sample, the analytes can be analyzed (e.g., reverse transcribed, amplified, and/or sequenced) by any of the variety of methods described herein.

For example, FIG. 3 shows the sequential hybridization/ligation of various domains to generate an oligonucleotide probe for capturing analytes, by a photo-hybridization/ligation method described herein.

As illustrated in FIG. 3, an oligonucleotide is immobilized on a substrate (e.g., an array) and may comprise a functional sequence such as a primer sequence. In some embodiments, the primer sequence is a sequencing handle that comprises a primer binding site for subsequent processing. The primer sequence can generally be selected for compatibility with any of a variety of different sequencing systems, e.g., 454 Sequencing, Ion Torrent Proton or PGM, Illumina X10, PacBio, Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Roche 454 sequencing, Ion Torrent Proton or PGM sequencing, Illumina X10 sequencing, PacBio SMRT sequencing, and Oxford Nanopore sequencing. Further, in some embodiments, functional sequences can be selected for compatibility with other sequencing systems, including non-commercialized sequencing systems.

Following a first cycle of photo-hybridization/ligation, an oligonucleotide comprising a part of a barcode (e.g., BC-A as shown in FIG. 3) is attached to the oligonucleotide molecule comprising the primer (e.g., R1 primer as shown in FIG. 3). In some embodiments, the barcode part can be common to all of the oligonucleotide molecules in a given feature. In some embodiments, the barcode part can be common to all of the oligonucleotide molecules in multiple substrate regions (e.g., features) in the same cycle (e.g., the three regions 210 in FIG. 2, Round 1, Cycle 1). In some embodiments, the barcode part can be different for oligonucleotide molecules in different substrate regions (e.g., features) in different cycle. In some embodiments, a splint with a sequence complementary to a portion of the primer of the immobilized oligonucleotide and an additional sequence complementary to a portion of the oligonucleotide comprising the part of the barcode (e.g., BC-A) facilitates the ligation of the immobilized oligonucleotide and the oligonucleotide comprising BC-A. In some embodiments, the splint for attaching the part of the barcode (e.g., BC-A) of various sequences to different substrate regions (e.g., features) is common among the cycles of the same round. In some embodiments, the splint for attaching the part of the barcode (e.g., BC-A) of various sequences to different substrate regions (e.g., features) can be different among the cycles of the same round. In some embodiments, the splint for attaching the part of the barcode may comprise a sequence complementary to the part (e.g., BC-A) or a portion thereof.

In FIG. 3, another cycle, such as a second cycle, of photo-hybridization/ligation involves the addition of another oligonucleotide comprising another part of a barcode (e.g., BC-B in FIG. 3) to the immobilized oligonucleotide molecule comprising the primer and BC-A. As shown in the figure, in some embodiments, a splint with a sequence complementary to a portion of the immobilized oligonucleotide comprising BC-A and an additional sequence complementary to a portion of the oligonucleotide comprising BC-B facilitates the ligation of the oligonucleotide comprising BC-B and the immobilized oligonucleotide comprising BC-A. In some embodiments, the splint for attaching part BC-B of various sequences to different substrate regions (e.g., features) is common among the cycles of the same round. In some embodiments, the splint for attaching BC-B to different substrate regions (e.g., features) can be different among the cycles of the same round. In some embodiments, the splint for attaching BC-B may comprise a sequence complementary to BC-B or a portion thereof and/or a sequence complementary to BC-A or a portion thereof.

FIG. 3 further illustrates a third cycle of photo-hybridization/ligation, which involves the addition of another oligonucleotide comprising another part of a barcode (e.g., BC-C), added to the immobilized oligonucleotide molecule comprising the primer, BC-A, and BC-B. In some embodiments, a splint with a sequence complementary to a portion of the immobilized oligonucleotide molecule comprising BC-B and an additional sequence complementary to a portion of the oligonucleotide comprising BC-C facilitates the ligation of the immobilized oligonucleotide molecule comprising BC-B and the oligonucleotide comprising BC-C. In some embodiments, the splint for attaching part BC-C of various sequences to different substrate regions (e.g., features) is common among the cycles of the same round. In some embodiments, the splint for attaching BC-C to different substrate regions (e.g., features) can be different among the cycles of the same round. In some embodiments, the splint for attaching BC-C may comprise a sequence complementary to BC-C or a portion thereof and/or a sequence complementary to BC-B or a portion thereof.

A fourth cycle of photo-hybridization/ligation may be performed, which involves the addition of another oligonucleotide comprising another part of a barcode (e.g., BC-D), added to the immobilized oligonucleotide molecule comprising the primer, BC-A, BC-B, and BC-C. In some embodiments, a splint with a sequence complementary to a portion of the immobilized oligonucleotide molecule comprising BC-C and an additional sequence complementary to a portion of the oligonucleotide comprising BC-D facilitates the ligation. In some embodiments, the splint for attaching part BC-D of various sequences to different substrate regions (e.g., features) is common among the cycles of the same round. In some embodiments, the splint for attaching BC-D to different substrate regions (e.g., features) can be different among the cycles of the same round. In some embodiments, the splint for attaching BC-D may comprise a sequence complementary to BC-D or a portion thereof and/or a sequence complementary to BC-C or a portion thereof. In some embodiments, as shown in FIG. 3, an oligonucleotide comprising BC-D further comprises a UMI and a capture domain.

In some embodiments, the splint comprises a sequence that is complementary to an oligonucleotide (e.g., an immobilized oligonucleotide), or a portion thereof, and a sequence that is complementary to an oligonucleotide containing a barcode, or a portion thereof. In some embodiments, the splint comprises a sequence that is perfectly complementary (e.g., is 100% complementary) to an oligonucleotide (e.g., an immobilized oligonucleotide), or a portion thereof, and/or a sequence that is perfectly complementary to an oligonucleotide containing a barcode, or a portion thereof. In some embodiments, the splint comprises a sequence that is not perfectly complementary (e.g., is not 100% complementary) to an oligonucleotide (e.g., an immobilized oligonucleotide), or a portion thereof, and/or a sequence that is not perfectly complementary to an oligonucleotide containing a barcode, or a portion thereof. In some embodiments, the splint comprises a sequence that is at least 70%, 75%, 80%, 85%, 90%, 95%, 96%, 97%, 98%, or 99% complementary to an oligonucleotide (e.g., an immobilized oligonucleotide), or a portion thereof, and/or a sequence that is complementary to an oligonucleotide containing a barcode, or a portion thereof. In some embodiments, the splint comprises a sequence that is perfectly complementary (e.g., is 100% complementary) to an oligonucleotide (e.g., an immobilized oligonucleotide), or a portion thereof, but is not perfectly complementary to a sequence that is complementary to an oligonucleotide containing a barcode, or a portion thereof. In some embodiments, the splint comprises a sequence that is not perfectly complementary (e.g., is not 100% complementary) to an oligonucleotide (e.g., an immobilized oligonucleotide), or a portion thereof, but is perfectly complementary to a sequence that is complementary to an oligonucleotide containing a barcode, or a portion thereof. So long as the splint is capable of hybridizing to an oligonucleotide (e.g., an immobilized oligonucleotide), or a portion thereof, and to a sequence that is complementary to an oligonucleotide containing a barcode, or a portion thereof, the splint need not have a sequence that is perfectly complementary to either the oligonucleotide (e.g., the immobilized oligonucleotide) or to the oligonucleotide containing a barcode.

In some embodiments, oligonucleotides that are exposed and do not receive a ligated oligonucleotide could receive the incorrect barcode during the next cycle or round. In order to prevent generating the wrong barcode at the wrong feature, unligated oligonucleotides may be rendered unavailable for hybridization and/or ligation, e.g., the unligated oligonucleotides can be capped and/or removed. In some embodiments, the oligonucleotides are modified at the 3' termini. Non-limiting examples of 3' modifications include dideoxy C-3' (3'-ddC), 3' inverted dT, 3' C3 spacer, 3' Amino, and 3' phosphorylation.

In some embodiments according to any of the methods described herein, the method further comprises blocking the 3' or 5' termini of barcoded oligonucleotide molecules. In some embodiments, the method further comprises blocking the unligated oligonucleotide molecules in the first region from ligation. In some embodiments, the blocking comprises adding a 3' dideoxy or a non-ligating 3' phosphoramidite to the barcoded oligonucleotide molecules. In some embodiments, the blocking comprises adding a 3' dideoxy or a non-ligating 3' phosphoramidite to the unligated oligonucleotide molecules. In some embodiments, the addition is catalyzed by a terminal transferase. In some embodiments, the terminal transferase is a terminal deoxynucleotidyl transferase (TdT). The blocking may be removed after the blocking reaction is completed. In some embodiments, the blocking is removed using an internal digestion of the barcoded oligonucleotide molecules after ligation is completed.

IV. Light-Controlled Surface Patterning In Situ Using Photoresist

In some aspects, provided herein is a method of patterning a surface in situ for producing an array on the surface, for example, by spatially-selective light-activated hybridization/ligation generating DNA sequences and/or combination of DNA sequences at spatial positions in the array. In some embodiments, the diversity of the DNA sequences and/or the combinations of DNA sequences can be generated combinatorially, and the DNA sequence or combination thereof at a particular spatial location in the array can be unique compared to those at some or all other spatial locations in the array. In some embodiments, the method comprises assembling nucleic acid sequences (e.g., barcode sequences, gene sequences, or genomic sequences including non-coding sequences) on immobilized oligonucleotides, e.g., based on hybridization and/or ligation, on a slide or wafer surface. In some embodiments, the in situ method comprises photolithography using one or more photoresist compositions to enable barcodes to be generated combinatorially, for example, in as few as three rounds of assembly. In some embodiments, exposure of the photoresist to irradiation may render the exposed regions dissolvable by a developer. In some embodiments, the photoresist in the unmasked region of the substrate is dissolved by a developer and removed. The developer may be organic or aqueous based. A non-limiting example of an aqueous base developer such as tetramethylammonium hydroxide aqueous solution.

In some aspects, provided herein is a method of patterning a surface in situ for producing an array on the surface. In some embodiments, the method comprises assembling barcode sequences on immobilized oligonucleotides, e.g., based on hybridization and/or ligation, on a slide surface. In some embodiments, the in situ method uses photoresist and photolithography to enable barcodes to be generated selectively on a discrete location on a slide surface. Hybridization and/or ligation of barcodes can be controlled, for example, using a contact photolithography process. For example, ligation can be achieved by exposing oligonucleotides for ligation upon degradation of a photoresist by irradiating a substrate through a photomask.

In some embodiments, the method comprises irradiating a substrate covered with a photoresist. In some embodiments, the irradiation is selective, for example, where one or more photomasks can be used such that only one or more specific regions of the array are exposed to irradiation stimuli (e.g., exposure to light such as UV, and/or exposure to heat induced by laser). In some embodiments, the substrate comprises an unmasked first region and a masked second region. In some embodiments, the photoresist in the unmasked first region is degraded upon irradiation to render oligonucleotide molecules available for hybridization and/or ligation. In some embodiments, the oligonucleotide in the masked second region are protected by a photoresist. In some embodiments, the photoresist is a positive photoresist. For example, the photoresist in the first region is exposed to light and degraded when the photoresist in the second region is photomasked. In some embodiments, the method further comprises attaching an oligonucleotide comprising a barcode sequence to oligonucleotide molecules in the first region via hybridization and/or ligation, while oligonucleotide molecules in the second region do not receive the barcode sequence.

In some embodiments, the oligonucleotide molecules on the substrate comprise one or more common sequences. In some embodiments, the one or more common sequences comprise a common primer sequence. The common primer sequence can be of about 5, about 6, about 7, about 8, about 9, about 10, about 15, about 20, about 25, about 30, about 35, about 40, about 45, about 50, or about 60 nucleotides in length. In some embodiments, the common primer sequence is between about 6 and about 45 nucleotides in length, e.g., between about 10 and about 35 nucleotides in length.

In some embodiments, the oligonucleotide molecules in the first region and oligonucleotide molecules in the second region are identical in sequence. In some embodiments, the oligonucleotide molecules on the substrate prior to the irradiating step are identical in sequence.

In some embodiments, oligonucleotide molecules in the first and the second regions are different. In some embodiments, oligonucleotide molecules in the first region and oligonucleotide molecules in the second region are different in sequences. In some embodiments, oligonucleotide molecules in the first region and oligonucleotide molecules in the second region comprise different barcode sequences. In some embodiments, oligonucleotide molecules on the substrate comprise two or more different sequences.

In some embodiments, the array comprises an arrangement of a plurality of features, e.g., each comprising one or more molecules such as a nucleic acid molecule (e.g., a DNA oligo). In some embodiments, the array comprises different oligonucleotides in different features. In some embodiments, oligonucleotide molecules on the substrate are immobilized in a plurality of features. Nucleotides immobilized on the substrate may be of different orientations. For example, in some embodiments, the 3' terminal nucleotides of immobilized oligonucleotide molecules are distal to the substrate. In some embodiments, the 5' terminal nucleotides of immobilized oligonucleotide molecules are distal to the substrate. In embodiments, where 5' terminal nucleotides of immobilized oligonucleotides are distal to the substrate, capping can involve blocking the 5' termini, for example via incorporation of a modified nucleotide (e.g., 7-methylguanine).

The oligonucleotide molecules on the substrate prior to the irradiating step may have a variety of properties, which include but are not limited to, length, orientation, structure, and modifications. The oligonucleotide molecules on the substrate prior to the irradiating step can be of about 5, about 6, about 7, about 8, about 9, about 10, about 15, about 20, about 25, about 30, about 35, about 40, about 45, about 50, about 55, about 60, about 70, about 80, about 90, or about 100 nucleotides in length. In some embodiments, oligonucleotide molecules on the substrate prior to the irradiating step are between about 5 and about 50 nucleotides in length. The oligonucleotide molecules on the substrate may comprise functional groups. In some embodiments, the functional groups are amino or hydroxyl groups. The functional groups can be protected or unprotected. In some embodiments, the functional groups are not protected, e.g., by a photo-sensitive group, moiety, or molecule prior to the irradiating step. In some embodiments, the functional groups are 3' hydroxyl groups of nucleotides.

In some embodiments, the method provided herein further comprises forming a pattern of oligonucleotide molecules on the substrate prior to applying the photoresist to the substrate. For example, the pattern of oligonucleotide can be formed by irradiating a substrate comprising a plurality of functional groups and a photoresist through a patterned mask, whereby the photoresist in a first region of the substrate is degraded, rendering functional groups in the first region available for reacting with functional groups in functionalized oligonucleotide molecules, whereas functional groups in a second region of the substrate are protected by the photoresist from reacting with functional groups in the oligonucleotide molecules; and contacting the substrate with the functionalized oligonucleotide molecules, wherein the functionalized oligonucleotide molecules are coupled to functional groups in the first region but not to functional groups in the second region.

In some embodiments, the plurality of functional groups of the substrate are not protected, e.g., by a photo-sensitive group, moiety, or molecule prior to the irradiating step. In some embodiments, the plurality of functional groups of the substrate are aldehyde groups. In some embodiments, the functional groups in the functionalized oligonucleotide molecules are amino groups. In some embodiments, the functionalized oligonucleotide molecules are 5' amine-terminated.

In some embodiments, the method further comprises heating the substrate to dryness during or after the contacting step. In some embodiments, the method further comprises blocking unreacted functional groups of the substrate. In some embodiments, the method further comprises rendering the reaction between functional groups of the substrate and the functionalized oligonucleotide molecules irreversible. For example, aldehyde groups of the substrate are reacted with 5' amino groups of the functionalized oligonucleotide molecules, and the substrate is contacted with a reagent (e.g., sodium borohydride) to block unreacted aldehyde groups and render the reaction irreversible.

In some embodiments, provided herein is a method to generate an array with barcode diversity in the 100s, 1,000s, 10,000s, 100,000s, 1,000,000s, or 10,000,000s. In some embodiments, a substrate comprising a dense lawn of a common oligonucleotide (e.g., partial R1 or R1 primer as shown in FIG. 3) is provided and may be protected with a photoresist layer. Using a series of photomasks, oligonucleotides in desired regions of the lawn may be iteratively deprotected via exposure to light and removal of the photoresist. In some embodiments, the method further comprises attaching a round 1 barcode to one or more exposed oligonucleotides, for example, by attaching an oligonucleotide cassette with a complementary region (e.g., complementary to a splint) and a barcode region. In some embodiments, the attachment may be performed by placing the substrate in a chamber or vessel (e.g., within which oligonucleotides such as those comprising barcode sequences can be delivered and ligated to nucleic acid molecules on the substrate). In some embodiments, the chamber or vessel is a flow cell or a device comprising microfluidic channels. In some embodiments, the method comprises flowing in the round 1 barcode (e.g., an oligonucleotide cassette) to be attached to the common oligonucleotide. The process can be repeated N cycles (each cycle for one or more features on an array) for round 1 until all desired features have been exposed (e.g., due to exposure of the photoresist covering the features to light) and the common oligonucleotides in the features have received the round 1 barcode which may be the same or different for molecules in any two given features. The round 1 barcode molecules can be ligated to the common oligonucleotides. The process can be repeated for M rounds to achieve a desired barcode diversity, for example, by attaching a round 2 barcode (which may be the same or different for molecules in any two given features), a round 3 barcode (which may be the same or different for molecules in any two given features), . . . , and a round M barcode (which may be the same or different for molecules in any two given features) to each of the growing oligo-nucleotides in the features. In some embodiments, each round comprises a plurality of cycles (each cycle for one or more features on an array) of photoresist exposure to light and oligonucleotide attachment until all desired features have been exposed once and the molecules in the features have received the barcode(s) (which may be the same or different for molecules in any two given features) for that round. In some embodiments, the method further comprises attaching a capture sequence to the barcoded oligonucle-otides, for example, by hybridization and/or ligation.

In some aspects, a method disclosed herein provides one or more advantages as compared to other arraying methods. For example, pre-synthesized barcodes can eliminate con-cern over barcode fidelity in base-by-base in situ approach. In addition, compared to base-by-base method, a method disclosed herein can reduce manufacturing time, cost of goods, and increase total yield. For example, only three or four rounds of hybridization and ligation may be required compared to 12-16 rounds in a typical base-by-base in situ arraying method. In one aspect, the method disclosed herein does not involve 5' to 3' base-by-base synthesis of a poly-nucleotide in situ on a substrate. In another aspect, there is no need for decoding as all barcodes are synthesized in defined locations on an array. In some aspects, feature scaling can readily be increased or decreased by changing photomasks and corresponding barcode diversity. In other aspects, a method disclosed herein is performed on a trans-parent substrate. Since a method disclosed herein does not depend on the use of microspheres (e.g., barcoded beads) to generate an oligonucleotide array, optical distortion or aber-rations caused by microspheres (which may not be trans-parent) during imaging of the oligonucleotide array and/or a sample (e.g., a tissue section) on the array can be avoided.

In some aspects, provided herein is a method of producing an array of polynucleotides. In some embodiments, an array comprises an arrangement of a plurality of features, e.g., each comprising one or more molecules such as a nucleic acid molecule (e.g., a DNA oligo), and the arrangement is either irregular or forms a regular pattern. The features and/or molecules on an array may be distributed randomly or in an ordered fashion (e.g., in spots that are arranged in rows and columns). In some embodiments, individual fea-tures in the array differ from one another based on their relative spatial locations. In some embodiments, the features and/or molecules are collectively positioned on a substrate.

In some embodiments, polynucleotides of the same or different nucleic acid sequences are immobilized on the substrate in a pattern prior to the irradiation. In some embodiments, the pattern comprises rows and/or columns. In some embodiments, the pattern comprises regular and/or irregular shapes (e.g., polygons).

In some embodiments, the method comprises irradiating an array with light. In some embodiments, the irradiation is selective, for example, where one or more photomasks can be used such that only one or more specific regions of the array are exposed to stimuli (e.g., exposure to light such as UV, and/or exposure to heat induced by laser). In some embodiments, the method comprises irradiating a first region of a substrate with a first light while a second region of the substrate is not irradiated with the first light. For instance, the substrate is exposed to the first light when the second region is photomasked while the first region is not photomasked. Alternatively, a focused light such as laser may be used to irradiate the first region but not the second region, even when the second region is not masked from the light. For example, the distance (pitch) between features may be selected to prevent the laser from degrading photo-resist protecting polynucleotides of an adjacent feature.

In some embodiments, the photoresist inhibits or blocks hybridization and/or ligation of oligonucleotide molecules in the first region and/or the second region. In some embodi-ments, the oligonucleotide molecules are prevented by the photoresist from hybridization to a nucleic acid such as a splint. In some embodiments, the oligonucleotide molecules are prevented by the photoresist from ligation to a nucleic acid. For example, the photoresist may inhibit or block the 3' or 5' end of an oligonucleotide molecule from chemical or enzymatic ligation, e.g., even when a splint may hybridize to the oligonucleotide molecule in order to bring a ligation partner in proximity to the 3' or 5' end of the oligonucleotide molecule. In some embodiments, the 3' or 5' end of the oligonucleotide molecule or a hybridization/ligation product thereof is capped.

In some embodiments, the irradiation results in degrada-tion of the photoresist such that the inhibition or blocking of hybridization and/or ligation to an oligonucleotide molecule in an exposed (e.g., unmasked) region is reduced or elimi-nated, whereas hybridization and/or ligation to an oligo-nucleotide molecule in an unexposed (e.g., masked) region remains inhibited or blocked by a photoresist which may be the same or different from the degraded photoresist.

In some embodiments, the method further comprises attaching a first barcode molecule comprising a first barcode sequence to an oligonucleotide molecule in an exposed (e.g., unmasked) region via hybridization and/or ligation. In some embodiments, one end of the first barcode molecule and one end of the oligonucleotide molecule may be directly ligated, e.g., using a ligase having a single-stranded DNA/RNA ligase activity such as a T4 DNA ligase or CircLigase™. The attachment may comprise hybridizing the first barcode mol-ecule and the oligonucleotide molecule to a splint, wherein one end of the first barcode molecule and one end of the oligonucleotide molecule are in proximity to each other. For example, the 3' end of the first barcode molecule and the 5' end of the oligonucleotide molecule may hybridize to a splint. Alternatively, the 5' end of the first barcode molecule and the 3' end of the oligonucleotide molecule are in proximity to each other. In some embodiments, proximity ligation is used to ligate a nick, with or without a gap-filling step that involves incorporation of one or more nucleic acids by a polymerase, based on the nucleic acid sequence of the splint which serves as a template.

In any of the embodiments herein, physical masks, e.g., a photolithography mask which is an opaque plate or film with transparent areas that allow light to shine through in a defined pattern, may be used.

In some embodiments, a first polynucleotide (e.g., an oligonucleotide) is deposited in region A of a substrate and a second polynucleotide (e.g., an oligonucleotide) is deposited in region B. Regions A are exposed to light while regions B are masked by a photomask. A photomask can be selected and/or adjusted to allow any suitable number and/or combination of regions on the substrate to be exposed to light or masked. Thus, the exposed region(s) and masked region(s) can be in any suitable pattern, which can be predetermined and/or adjusted as needed during the arraying process. In addition, a mirror, mirror array, a lens, a moving stage, and/or a photomask can be used to direct the light to or away from the region(s) of interest. In some embodiments, the first polynucleotide and the second polynucleotide can comprise the same sequence or different sequences. For example, first polynucleotides in region A and second polynucleotides in region B may form a lawn of universal oligonucleotide molecules on the substrate. The oligonucleotides may be attached to the substrate at their 5' ends or 3' ends. The first and second polynucleotides can be embedded in a first and a second photoresist, respectively. The first and second photoresist can be the same or different. In some embodiments, first polynucleotides in region A and second polynucleotides in region B are embedded in the same photoresist layer. Once regions A are exposed to light to deprotect the first polynucleotide while the second polynucleotide in regions B remain protected, a first barcode can be attached to the first polynucleotide. In some embodiments, a hybridization complex is formed between the first polynucleotide, a splint, and a polynucleotide comprising a first barcode (e.g., a round 1 barcode 1A). The polynucleotide comprising the first barcode comprise at least a first barcode sequence and a hybridization region that hybridizes to the splint which is a first splint, and may further comprise a hybridization region that hybridizes to a round 2 splint (e.g., for attaching a round 2 barcode after the round 1 barcode 1A). The first splint comprises at least a hybridization region that hybridizes to the first polynucleotide and a hybridization region that hybridizes to the polynucleotide comprising the first barcode. Optionally, the polynucleotide comprising the first barcode may be ligated to the first polynucleotide, with or without gap filling using the first splint as a template. As a result, provided in some embodiments is an array comprising the first and second polynucleotides, wherein the first polynucleotide is barcoded with the first barcode and the second polynucleotide is not, and neither of the barcoded first polynucleotide nor the second polynucleotide comprises a photo-cleavable moiety.

In some embodiments, the polynucleotide comprising the first barcode may comprise no photo-cleavable moiety that blocks hybridization and/or ligation. In these examples, the array may be exposed to light to degrade photoresist that protects the second polynucleotide, and a second barcode can be attached to the second polynucleotide. In some embodiments, a hybridization complex is formed between the second polynucleotide, a second splint, and a polynucleotide comprising a second barcode (e.g., a round 1 barcode 1B). The polynucleotide comprising the second barcode comprises at least a second barcode sequence and a hybridization region that hybridizes to the second splint, and may further comprise a hybridization region that hybridizes to a round 2 splint (e.g., for attaching a round 2 barcode after the round 1 barcode 1B). The second splint comprises at least a hybridization region that hybridizes to the second polynucleotide and a hybridization region that hybridizes to the polynucleotide comprising the second barcode. While the polynucleotide comprising the first barcode may be available for hybridization and/or ligation, the second barcode may be specifically attached to the second polynucleotide but not to the first polynucleotide barcoded with the first barcode. For example, the sequence of the second splint may be selected such that it specifically hybridizes to the second polynucleotide but not to the polynucleotide comprising the first barcode. In these examples, both the first barcode (e.g., barcode 1A) and the second barcode (e.g., barcode 1B) are round 1 barcodes. Optionally, the polynucleotides comprising the first/second barcodes may be ligated to the first/second polynucleotides, respectively, with or without gap filling using the first/second splints as templates. As a result, provided in some embodiments is an array comprising the first and second polynucleotides barcoded with the first barcode and the second barcode, respectively, wherein neither of the barcoded polynucleotides comprises a photo-cleavable moiety.

In some examples, polynucleotides in regions A and/or polynucleotides in regions B may undergo one or more additional rounds of barcoding. For example, after the round 1 barcoding, regions A may contain polynucleotides P1 and P3 each barcoded with round 1 barcode 1A (i.e., polynucleotides 1A-P1 and 1A-P3) and regions B may contain polynucleotides P2 and P4 each barcoded with round 1 barcode 1B (i.e., polynucleotides 1B-P2 and 1B-P4). All of polynucleotides 1A-P1, 1A-P3, 1B-P2, and 1B-P4 may be embedded in a photoresist. With light exposure and photomasking, any one or more of polynucleotides 1A-P1 and 1A-P3 (in regions A) and 1B-P2 and 1B-P4 (in regions B) may undergo a second round of barcoding.

For instance, a round 2 barcode 2A may be attached to any one of polynucleotides 1A-P1, 1A-P3, 1B-P2, and 1B-P4. In some embodiments, a round 2 barcode 2A may be attached to any two of polynucleotides 1A-P1, 1A-P3, 1B-P2, and 1B-P4. In some embodiments, a round 2 barcode 2A may be attached to any three of polynucleotides 1A-P1, 1A-P3, 1B-P2, and 1B-P4. In some embodiments, a round 2 barcode 2A may be attached to all of polynucleotides 1A-P1, 1A-P3, 1B-P2, and 1B-P4.

In other examples, different round 2 barcodes 2A and 2B may be used. In some embodiments, barcode 2A is attached to polynucleotides 1A-P1 and 1A-P3 (in regions A) while barcode 2B is attached to polynucleotides 1B-P2 and 1B-P4 (in regions B). For higher order rounds, for example, round m (m being an integer of 2 or greater), the regions A polynucleotides may receive barcode mA while the regions B polynucleotides receive barcode mB. Barcodes mA and mB may be the same or different in sequence. Thus, for each round, the regions A polynucleotides (e.g., P1 and P3) and the regions B polynucleotides (e.g., P2 and P4) may have no crossover, generating barcoded polynucleotides mA- . . . -1A-P1 and mA- . . . -1A-P3 (in regions A) and mB- . . . -1B-P2 and mB- . . . -1B-P4 (in regions B).

Alternatively, the regions A polynucleotides (e.g., P1 and P3) and the regions B polynucleotides (e.g., P2 and P4) may have crossover. For example, barcode 2A is attached to polynucleotides 1A-P1 (in regions A) and 1B-P2 (in regions B) while barcode 2B is attached to polynucleotides 1A-P3 (in regions A) and 1B-P4 (in regions B). For example, barcoded polynucleotides 2A-1A-P1 and 2B-1A-P3 (in regions A) and 2A-1B-P2 and 2B-1B-P4 (in regions B) may be generated. For round m (m being an integer of 2 or greater), one or more of the regions A polynucleotides and/or one or more of the regions B polynucleotides may receive barcode mA, while one or more of the regions A polynucleotides and/or one or more of the regions B polynucleotides barcode mB. Barcodes mA and mB may be the same or different in sequence.

In some examples, round m (m being an integer of 2 or greater) barcodes mA, mB, and mC may be attached to any polynucleotides barcoded in the previous round (i.e., round m−1), and mA, mB, and mC may be the same or different. In other examples, round m (m being an integer of 2 or greater) barcodes mA, mB, mC, and mD may be attached to any polynucleotides barcoded in the previous round (i.e., round m−1), and mA, mB, mC, and mD may be the same or different.

In any of the embodiments herein, the barcoding rounds can be repeated m times to achieve a desired barcode diversity, m being an integer of 2 or greater. In some embodiments, m is 3, 4, 5, 6, 7, 8, 9, or 10, or greater than 10. In any of the embodiments herein, each of the m barcoding rounds may comprise n cycles (each cycle for molecules in one or more features), wherein integer n is 2 or greater and independent of m. In some embodiments, n is 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or greater than 50.

FIG. 1 provides a non-limiting example, where the substrate comprises a surface for nucleic acids to be deposited on and can be in the form of a slide, such as a glass slide or a wafer such as a silicon oxide wafer. In some examples, the substrate is transparent. A lawn of polynucleotides without photo-cleavable moieties, such as photo-caged oligos, may be deposited on the substrate and immobilized. A photoresist may be coated onto the substrate and cover the polynucleotides. One or more regions (e.g., regions A) on the substrate are exposed to light in order to degrade the photoresist, rendering the polynucleotides in the one or more regions available for hybridization and/or ligation, while one or more other regions (e.g., regions B) on the substrate are masked or not exposed to light. Patterned exposure of polynucleotides on the underlying substrate is provided, and a round 1 barcode (such as barcode 1A) may be attached to the exposed polynucleotides via hybridization and/or ligation. For example, an oligonucleotide may be used to hybridize to an exposed polynucleotide and a polynucleotide comprising the round 1 barcode. The oligonucleotide may comprise a splint that facilitates proximity ligation of one end of the exposed polynucleotide and one end of the polynucleotide comprising the round 1 barcode, thus attaching the barcode to the exposed polynucleotide. The proximity ligation may occur immediately following hybridization, in a subsequent step of the same cycle, or in a subsequent cycle (for example, while molecules comprising barcode 1B are ligated to polynucleotides in regions B). Thus, the one or more regions (e.g., regions A) on the substrate contain polynucleotides barcoded with the round 1 barcode (such as barcode 1A), while the one or more other regions (e.g., regions B) on the substrate do not contain polynucleotides barcoded with the round 1 barcode. In some embodiments, the photoresist covering polynucleotides in the one or more other regions (e.g., regions B) is not removed prior to the next cycle where a photoresist is applied to cover polynucleotides in the one or more regions (e.g., regions A). In some embodiments, the photoresist covering polynucleotides in the one or more other regions (e.g., regions B) is removed prior to the next cycle. In some embodiments, the photoresist is removed from the substrate (e.g., all regions on the substrate) prior to the next cycle, and a new layer of a photoresist composition (which may be the same or different from the removed photoresist composition) is applied to the substrate, e.g., to cover both regions A and regions B.

In the next cycle, the polynucleotides barcoded with 1A in regions A are masked while regions B are exposed to light in order to degrade the photoresist and expose the polynucleotides in regions B. Another round 1 barcode (barcode 1B) may be attached to the exposed polynucleotides in regions B via hybridization and/or ligation, for example, as described above for attaching barcode 1A. In some embodiments, as shown in FIG. 2, a method disclosed herein comprises M rounds, where each round comprises N cycles (an exemplary cycle is shown in FIG. 1) to achieve a desired barcode diversity up to $N^M$, wherein M and N are integers independent of each other and are at least 2.

In some embodiments, the barcode sequences received by oligonucleotide molecules in feature(s) on the substrate in cycle I and in feature(s) in cycle J are different, wherein I and J are integers and $1 \le I < J \le N$. In some embodiments, the barcode sequences received by oligonucleotide molecules in feature(s) on the substrate in cycle I and in feature(s) in cycle J are the same, wherein I and J are integers and $1 \le I < J \le N$.

In some embodiments according to any one of the methods described herein, the irradiating and contacting steps are repeated in one or more cycles. In some embodiments, the photoresist is not removed prior to the one or more of the N cycles. In some embodiments, the photoresist is not removed during the one or more of the N cycles. In some embodiments, the photoresist is not removed between the one or more of the N cycles. In some embodiments, the method does not comprise re-applying a photoresist to the substrate prior to the one or more of the N cycles. In some embodiments, the method does not comprise re-applying a photoresist to the substrate during the one or more of the N cycles. In some embodiments, the method does not comprise re-applying a photoresist to the substrate during the one or more of the N cycles.

In some embodiments, the method comprises M rounds, wherein M is an integer of 2 or greater. In some embodiments, each of the M rounds comprises one or more cycles. In some embodiments, the method comprises removing photoresist from the substrate after each round and re-applying photoresist to the substrate prior to a new round. In some embodiments, each of the M rounds comprises N cycles. In some embodiments, N≥3.

In some embodiments according to any one of the methods described herein, the oligonucleotide molecules in a feature of the substrate receive a first barcode sequence in one of the cycles in round K, wherein K is an integer and $1 \le K < M$. In some embodiments, the oligonucleotide molecules in the feature comprising the first barcode sequence receive a second barcode sequence in one of the cycles in round (K+1), thereby forming oligonucleotide molecules comprising the first and second barcode sequences. In some embodiments, the diversity of barcode sequences in the oligonucleotides in a plurality of features on the substrate is $N^M$.

Figures 4A, 4B:
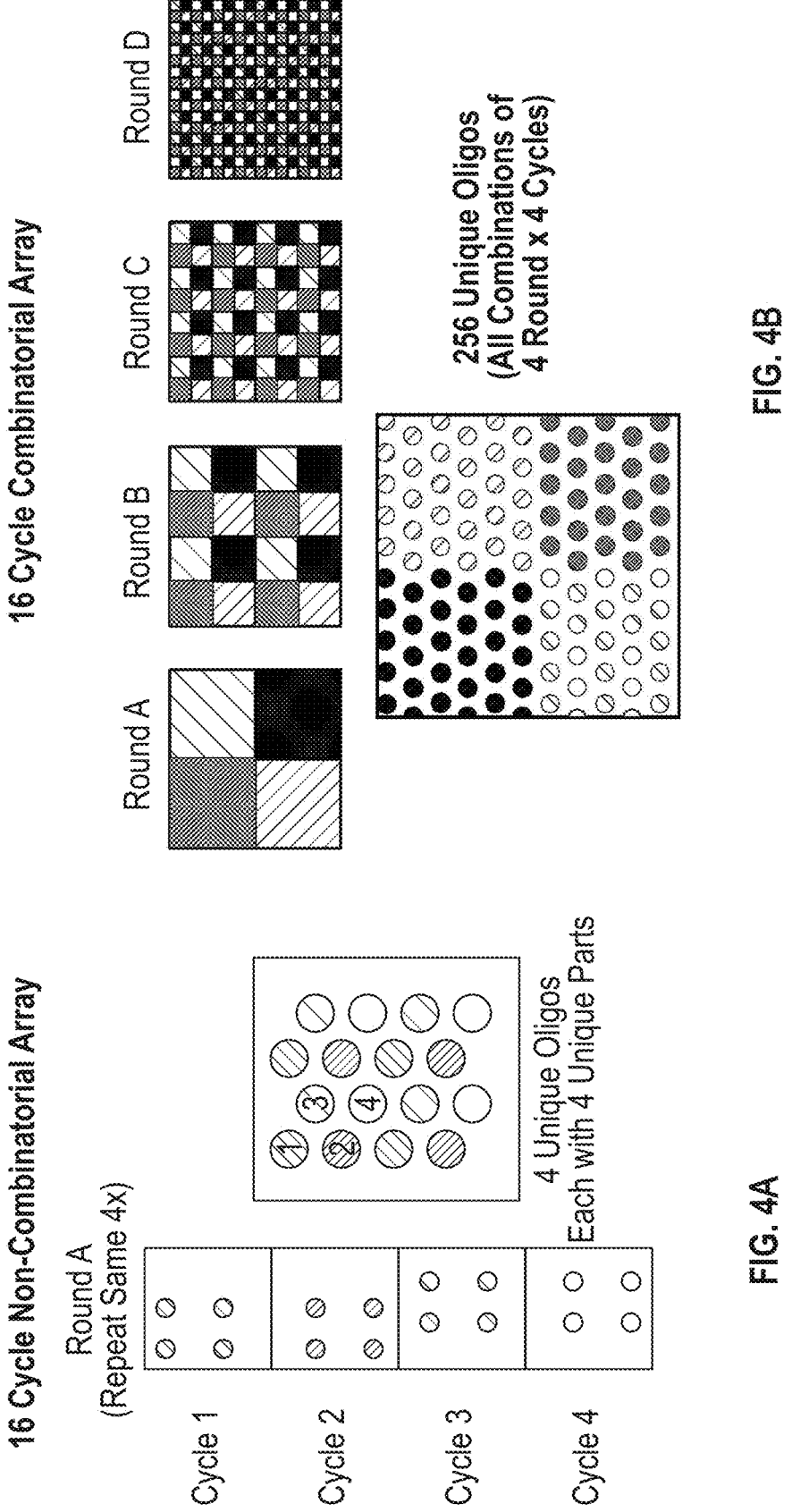
FIG. 4A is a schematic illustration of an exemplary non-combinatorial method for generating an array.
FIG. 4B is a schematic illustration of an exemplary combinatorial method for generating an array.

FIGS. 4A and 4B show additional exemplary methods for generating oligonucleotide arrays. FIG. 4A shows a 16 cycle non-combinatorial array over 4 rounds and 4 cycles. In cycle 1 of Round A, 4 features are irradiated and ligated to a first part of the oligonucleotide barcode. Cycle 2-4 repeats cycle 1 in 4 different features and ligating a first part of the oligonucleotide barcode of different sequences. The irradiation in 4 cycles may be achieved via the same photomask translated to different positions on the substrate. Round A is repeated 4 times to generate an array of 4 unique oligonucleotides each with 4 unique parts (e.g., barcodes).

In some aspects, disclosed herein is a method for generating a molecular array, comprising irradiating a substrate through a first photomask comprising an opening corresponding to a region of a plurality of regions on the substrate, wherein a first oligonucleotide of at least four nucleotides in length is attached to oligonucleotide molecules in the region to generate extended oligonucleotide molecules. Multiple cycles of the irradiation and oligonucleotide attachment can be performed, one cycle for each of the plurality of regions, by translating the first photomask across the substrate until all regions have received the first oligonucleotide. In some embodiments, the method can further comprise irradiating the substrate through a second photomask comprising multiple openings corresponding to a set of sub-regions each of which is in one of the regions, wherein a second oligonucleotide of at least four nucleotides in length is attached to the extended oligonucleotide molecules in the set of sub-regions to generate further extended oligonucleotide molecules. Multiple cycles of the irradiation and oligonucleotide attachment can be performed, one cycle for each set of sub-regions, by translating the second photomask across the substrate until all sub-regions of all regions have received the second oligonucleotide, thereby providing on the substrate an array comprising oligonucleotide molecules. In some embodiments, the method can further comprise irradiating the substrate through a third photomask comprising multiple openings corresponding to a set of sub-sub-regions each of which is in one of the sub-regions, wherein a third oligonucleotide of at least four nucleotides in length is attached to the further extended oligonucleotide molecules in the set of sub-sub-regions to generate even further extended oligonucleotide molecules. Again, multiple cycles of the irradiation and oligonucleotide attachment are performed, one cycle for each set of sub-sub-regions, by translating the third photomask across the substrate until all sub-sub-regions of all sub-regions of all regions have received the third oligonucleotide.

FIG. 4B shows a combinatorial approach over 4 rounds each having 4 cycles (16 cycles in total). In Round A, 4 square areas on the substrate are each ligated with a unique first part of the barcode (1 square per cycle, 4 cycles in total). A first photomask comprising an opening corresponding to one of the four squares in Round A can be translated across the substrate, one cycle for each square, until all four squares have received the first oligonucleotide. Round B subdivides each square area from Round A into 4 square areas (a total of 16 square areas in Round B), wherein in each subdivided square area within an area of Round A is ligated to a unique second part of the barcode. The subdivision may be achieved, for example, with a second photomask comprising a pattern that correspond with the 4 checkered areas shown in Round B, and translating the photomask to other square regions in Round B. For instance, the second photomask can comprise four openings corresponding to the checkered squares for a first cycle of ligation in Round B, and the second photomask can be translated to the right such that the four openings correspond to the four squares with diagonal lines for a second cycle of ligation in Round B, and so on. The steps are repeated with different (e.g., finer) photomasks in Round C (a total of 64 square areas) and Round D (a total of 256 square areas). For instance, a third photomask comprising 16 openings corresponding to the checkered squares in Round C can be used for the four cycles of ligation in Round C, and a fourth photomask comprising 64 openings corresponding to the checkered squares in Round D can be used for the four cycles of ligation in Round D. An array comprising 256 unique 4-part oligonucleotide barcodes can be generated, wherein each circular feature shown in FIG. 4B within a square area receives the same barcode. In some examples, the features are capable of achieving single cell scale resolution (e.g., between 1 and 10 microns in diameter). For example, additional rounds shown in FIG. 4B may be used to pattern the substrate such that each feature receives a unique barcode, and the diameter of each feature is no more than 1 micron, no more than 2 microns, no more than 3 microns, no more than 4 microns, no more than 5 microns, no more than 6 microns, no more than 7 microns, no more than 8 microns, no more than 9 microns, or no more than 10 microns.

FIG. 9 is a schematic diagram illustrating an exemplary method of the in situ array generation described herein. FIG. 9 shows three rounds of ligation on a substrate. In round 1, a photoresist layer is applied on an aldehyde-coated glass substrate. The photoresist-coated substrate is exposed to UV light through a photomask comprising a plurality of openings, wherein the UV irradiation is directed through the openings to the substrate. The photoresist is selectively removed by UV light from known locations on the substrate to reveal the aldehyde groups. Amine terminated oligonucleotides are then applied to the physically accessible regions with exposed aldehyde groups and the substrate is heated to facilitate ligation. Unligated aldehyde groups are reduced to alcohol by sodium borohydride. Unligated 3' termini of the oligonucleotides is blocked with TdT. The cycle of UV irradiation and ligation is repeated to expose new regions and ligate new spatial barcodes in the new regions. At the end of round 1, the photoresist is removed and re-applied. In round 2, the photoresist is selectively removed by UV light from known locations on the substrate to reveal the ligation handles (oligonucleotides ligated in round 1). A ligation mix is applied to the exposed ligation handles, and the un-ligated oligonucleotides are capped with terminal 3' dideoxy. The cycle of UV irradiation and ligation is repeated to expose new ligation handles and ligate to the ligation handles new spatial barcodes. At the end of round 2, the photoresist is removed and re-applied. In round 3, steps in round 2 are repeated, and the photoresist is removed at the end of round 3 to produce the in situ array of spatial barcodes.

In some embodiments, the features on the substrate may correspond to regions of a substrate in which one or more barcodes have been incorporated. In some embodiments, the feature(s) may be no more than 0.5 micron, no more than 1 micron, no more than 5 microns, no more than 10 microns, or no more than 15 microns, no more than 20 microns, no more than 25 microns, no more than 30 microns, or no more than 35 microns, no more than 40 microns, no more than 45 microns, or no more than 50 microns in diameter. In some embodiments, the features on the substrate are below 10 microns in diameter (e.g., single cell scale resolution) and provide high throughput readout (e.g., by sequencing) for analyzing a sample, such as a tissue sample.

V. Compositions, Kits, and Methods of Use

Also provided are compositions produced according to the methods described herein. These compositions include nucleic acid molecules and complexes, such as hybridization complexes, and kits and articles of manufacture (such as arrays) comprising such molecules and complexes.

In particular embodiments, provided herein is a composition comprising: (i) a substrate comprising a first region and a second region, (ii) hybridization complexes in the first region, wherein at least one of the hybridization complexes comprise an oligonucleotide molecule immobilized in the first region hybridized to a first splint, which is in turn hybridized to a first oligonucleotide comprising a first bar- code sequence, and (iii) oligonucleotide molecules immo- bilized in the second region and protected by a photoresist from hybridization and/or ligation. In some embodiments, the composition further comprises a photoresist. In some embodiments, the photoresist forms a photoresist layer. In some embodiments, the oligonucleotide molecules immobi- lized in the second region are embedded in the photoresist layer. In some embodiments, the composition further com- prises a ligase capable of ligating the first oligonucleotide and the oligonucleotide molecule immobilized in the first region using the first splint as template. In some embodi- ments, the composition optionally comprises a polymerase capable of gap filling using the first splint as template prior to the ligation.

In some embodiments, provided herein is a composition, comprising: (i) a substrate comprising a first region and a second region, (ii) hybridization complexes in the first region, wherein at least one of the hybridization complexes comprise an oligonucleotide molecule immobilized in the first region hybridized to a first splint, which is in turn hybridized to a first oligonucleotide comprising a first bar- code sequence, wherein the hybridization complexes are protected by a first photoresist from hybridization and/or ligation, and (iii) oligonucleotide molecules immobilized in the second region and protected by a second photoresist from hybridization and/or ligation. In some embodiments, the first photoresist and the second photoresist are the same. In some embodiments, the first photoresist and the second photoresist are different.

In some embodiments, provided herein is a composition, comprising a substrate comprising a plurality of universal oligonucleotide molecules immobilized thereon, wherein the universal oligonucleotide molecules in a first region of the substrate are available for hybridization and/or ligation, and the universal oligonucleotide molecules in a second region of the substrate are embedded in a photoresist and protected from hybridization and/or ligation. In some embodiments, the composition further comprises a photo- mask masking the second region while exposing the first region to light. In some embodiments, the composition further comprises hybridization complexes in the first region, wherein at least one of the hybridization complexes comprise a universal oligonucleotide molecule immobilized in the first region hybridized to a first splint, which is in turn hybridized to a first oligonucleotide comprising a first bar- code sequence.

Also provided herein are arrays comprising any one or more of the molecules, complexes, and/or compositions disclosed herein. Typically, an array includes at least two distinct nucleic acid polymers that differ by monomeric sequence immobilized on, e.g., covalently to, different and known locations on the substrate surface. In certain embodi- ments, each distinct nucleic acid sequence of the array is typically present as a composition of multiple copies of the polymer on the substrate surface, e.g. as a spot on the surface of the substrate. The number of distinct nucleic acid sequences, and hence spots or similar structures, present on the array may vary, but is generally at least, usually at least 5 and more usually at least 10, where the number of different spots on the array may be as a high as 50, 100, 500, 1000, 10,000, 1,000,000, 10,000,000 or higher, depending on the intended use of the array. The spots of distinct polymers present on the array surface are generally present as a pattern, where the pattern may be in the form of organized rows and columns of spots, e.g. a grid of spots, across the substrate surface, a series of curvilinear rows across the substrate surface, e.g. a series of concentric circles or semi-circles of spots, and the like. The density of spots present on the array surface may vary, but is generally at least about 10 and usually at least about 100 spots/cm$^2$, where the density may be as high as 10$^6$ or higher, or about 10$^5$ spots/cm$^2$. In other embodiments, the polymeric sequences are not arranged in the form of distinct spots, but may be positioned on the surface such that there is substan- tially no space separating one polymer sequence/feature from another. The density of nucleic acids within an indi- vidual feature on the array may be as high as 1,000, 10,000, 25,000, 50,000, 100,000, 500,000, 1,000,000, or higher per square micron depending on the intended use of the array.

In some embodiments, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini, e.g. the 3' or 5' terminus.

Arrays can be used to measure large numbers of analytes simultaneously. In some embodiments, oligonucleotides are used, at least in part, to create an array. For example, one or more copies of a single species of oligonucleotide (e.g., capture probe) can correspond to or be directly or indirectly attached to a given feature in the array. In some embodi- ments, a given feature in the array includes two or more species of oligonucleotides (e.g., capture probes). In some embodiments, the two or more species of oligonucleotides (e.g., capture probes) attached directly or indirectly to a given feature on the array include a common (e.g., identical) spatial barcode.

In some embodiments, an array can include a capture probe attached directly or indirectly to the substrate. The capture probe can include a capture domain (e.g., a nucleo- tide or amino acid sequence) that can specifically bind (e.g., hybridize) to a target analyte (e.g., mRNA, DNA, or protein) within a sample. In some embodiments, the binding of the capture probe to the target (e.g., hybridization) can be detected and quantified by detection of a visual signal, e.g., a fluorophore, a heavy metal (e.g., silver ion), or chemilu- minescent label, which has been incorporated into the target. In some embodiments, the intensity of the visual signal correlates with the relative abundance of each analyte in the biological sample. Since an array can contain thousands or millions of capture probes (or more), an array can interro- gate many analytes in parallel. In some embodiments, the binding (e.g., hybridization) of the capture probe to the target can be detected and quantified by creation of a molecule (e.g., cDNA from captured mRNA generated using reverse transcription) that is removed from the array, and processed downstream (e.g., sequenced).

Kits for use in analyte detection assays are provided. In some embodiments, the kit at least includes an array as disclosed herein. The kits may further include one or more additional components necessary for carrying out an analyte detection assay, such as sample preparation reagents, buf- fers, labels, and the like. As such, the kits may include one or more containers such as tubes, vials or bottles, with each container containing a separate component for the assay, and reagents for carrying out an array assay such as a nucleic acid hybridization assay or the like. The kits may also include a denaturation reagent for denaturing the analyte, buffers such as hybridization buffers, wash mediums, enzyme substrates, reagents for generating a labeled target sample such as a labeled target nucleic acid sample, negative and positive controls and written instructions for using the subject array assay and for carrying out an array based assay. The instructions may be printed on a substrate, such as paper or plastic, etc. As such, the instructions may be present in the kits as a package insert, in the labeling of the container of the kit or components thereof (i.e., associated with the packaging or sub-packaging), etc.

The subject arrays find use in a variety of different applications, where such applications are generally analyte detection applications in which the presence of a particular analyte in a given sample is detected at least qualitatively, if not quantitatively. Protocols for carrying out such assays are well known to those of skill in the art and need not be described in great detail here. Generally, the sample suspected of comprising the analyte of interest (e.g., a tissue section) is contacted with an array produced according to the subject methods under conditions sufficient for the analyte (e.g., mRNA) to bind to its respective binding pair member (e.g., poly(dT) capture domain) that is present on the array. Thus, if the analyte of interest is present in the sample, it binds to the array at a site proximal to its complementary binding member and a complex is formed on the array. The presence of this binding complex on the array is then detected, e.g. through use of a signal production system, e.g. an isotopic or fluorescent label present on the analyte, etc., and/or through sequencing of one or more components of the binding complex or a product thereof. The presence of the analyte in the sample is then deduced from the detection of binding complexes on the substrate, or sequence detection and/or analysis (e.g., by sequencing) of molecules indicative of the formation of the binding complex. In some embodiments, RNA molecules (e.g., mRNA) from a sample are captured by oligonucleotides (e.g., capture probes comprising a barcode and a poly(dT) sequence) on an array prepared by a method disclosed herein, cDNA molecules are generated via reverse transcription of the captured RNA molecules, and the cDNA molecules (e.g., a first strand cDNA) or portions or products (e.g., a second strand cDNA synthesized using a template switching oligonucleotide) thereof can be separated from the array and sequenced. Sequencing data obtained from molecules prepared on the array can be used to deduce the presence/absence or an amount of the RNA molecules in the sample.

Specific analyte detection applications of interest include hybridization assays in which the nucleic acid arrays of the present disclosure are employed. In these assays, a sample of target nucleic acids or a tissue section is first prepared, where preparation may include labeling of the target nucleic acids with a label, e.g., a member of a signal producing system. Following sample preparation, the sample is contacted with the array under hybridization conditions, whereby complexes are formed between target nucleic acids that are complementary to probe sequences attached to the array. The formation and/or presence of hybridized complexes is then detected, e.g., by analyzing molecules that are generated following the formation of the hybridized complexes, such as cDNA or a second strand generated from an RNA captured on the array. Specific hybridization assays of interest which may be practiced using the subject arrays include: gene discovery assays, differential gene expression analysis assays; nucleic acid sequencing assays, single nucleotide polymorphisms (SNPs) assays, copy number variation (CNV) assays, tumor infiltrating lymphocyte assays, and the like.

A. Spatial Analysis

In particular embodiments, provided herein are kits and compositions for spatial array-based analysis of biological samples. Array-based spatial analysis methods involve the transfer of one or more analytes from a biological sample (e.g., a tissue section) to an array of features on a substrate, where each feature is associated with a unique spatial location on the array. Subsequent analysis of the transferred analytes includes determining the identity of the analytes and the spatial location of each analyte within the biological sample. The spatial location of each analyte within the biological sample is determined based on the feature to which each analyte is bound on the array, and the feature's relative spatial location within the array. In some embodiments, the array of features on a substrate comprise a spatial barcode that corresponds to the feature's relative spatial location within the array. Each spatial barcode of a feature may further comprise a fluorophore, to create a fluorescent hybridization array. A feature may comprise UMIs that are generally unique per nucleic acid molecule in the feature— so the number of unique molecules can be estimated, as opposed to an artifact in experiments or PCR amplification bias that drives amplification of smaller, specific nucleic acid sequences.

In particular embodiments, the kits and compositions for spatial array-based analysis provide for the detection of differences in an analyte level (e.g., gene and/or protein expression) within different cells in a tissue of a mammal or within a single cell from a mammal. For example, the kits and compositions can be used to detect the differences in analyte levels (e.g., gene and/or protein expression) within different cells in histological slide samples (e.g., tissue section), the data from which can be reassembled to generate a three-dimensional map of analyte levels (e.g., gene and/or protein expression) of a tissue sample obtained from a mammal, e.g., with a degree of spatial resolution (e.g., single-cell scale resolution).

In some embodiments, an array generated using a method disclosed herein can be used in array-based spatial analysis methods which involve the transfer of one or more analytes from a biological sample to an array of features on a substrate, each of which is associated with a unique spatial location on the array. Subsequent analysis of the transferred analytes includes determining the identity of the analytes and the spatial location of each analyte within the sample. The spatial location of each analyte within the sample is determined based on the feature to which each analyte is bound in the array, and the feature's relative spatial location within the array.

There are at least two general methods to associate a spatial barcode with one or more neighboring cells, such that the spatial barcode identifies the one or more cells, and/or contents of the one or more cells, as associated with a particular spatial location. One general method is to drive target analytes out of a cell and towards the spatially-barcoded array. In some embodiments, the spatially-barcoded array populated with capture probes is contacted with a sample, and sample is permeabilized, allowing the target analyte to migrate away from the sample and toward the array. The target analyte interacts with a capture probe on the spatially-barcoded array. Once the target analyte hybridizes/ is bound to the capture probe, the sample is optionally removed from the array and the capture probes are analyzed in order to obtain spatially-resolved analyte information.

Another general method is to cleave the spatially-barcoded capture probes from an array, and drive the spatially-barcoded capture probes towards and/or into or onto the sample. In some embodiments, the spatially-barcoded array populated with capture probes is contacted with a sample. The spatially-barcoded capture probes are cleaved and then interact with cells within the provided sample. The interaction can be a covalent or non-covalent cell-surface interaction. The interaction can be an intracellular interaction facilitated by a delivery system or a cell penetration peptide. Once the spatially-barcoded capture probe is associated with a particular cell, the sample can be optionally removed for analysis. The sample can be optionally dissociated before analysis. Once the tagged cell is associated with the spatially-barcoded capture probe, the capture probes can be analyzed (e.g., by sequencing) to obtain spatially-resolved information about the tagged cell.

Sample preparation may include placing the sample on a slide, fixing the sample, and/or staining the sample for imaging. The stained sample may be imaged on the array using both brightfield (to image the sample hematoxylin and eosin stain) and/or fluorescence (to image features) modalities. In some embodiments, target analytes are then released from the sample and capture probes forming the spatially-barcoded array hybridize or bind the released target analytes. The sample is then removed from the array and the capture probes cleaved from the array. The sample and array are then optionally imaged a second time in one or both modalities (brightfield and fluorescence) while the analytes are reverse transcribed into cDNA, and an amplicon library is prepared and sequenced. Image(s) can then be spatially-overlaid in order to correlate spatially-identified sample information with sequencing data (e.g., gene expression information). When the sample and array are not imaged a second time, a spot coordinate file may be supplied. The spot coordinate file can replace the second imaging step. Further, amplicon library preparation can be performed with a unique PCR adapter and sequenced.

In some embodiments, a spatially-labelled array on a substrate is used, where capture probes labelled with spatial barcodes are clustered at areas called features. The spatially-labelled capture probes can include a cleavage domain, one or more functional sequences, a spatial barcode, a unique molecular identifier, and a capture domain. The spatially-labelled capture probes can also include a 5' end modification for reversible attachment to the substrate. The spatially-barcoded array is contacted with a sample, and the sample is permeabilized through application of permeabilization reagents. Permeabilization reagents may be administered by placing the array/sample assembly within a bulk solution. Alternatively, permeabilization reagents may be administered to the sample via a diffusion-resistant medium and/or a physical barrier such as a lid, wherein the sample is sandwiched between the diffusion-resistant medium and/or barrier and the array-containing substrate. The analytes are migrated toward the spatially-barcoded capture array using any number of techniques disclosed herein. For example, analyte migration can occur using a diffusion-resistant medium lid and passive migration. As another example, analyte migration can be active migration, using an electrophoretic transfer system, for example. Once the analytes are in close proximity to the spatially-barcoded capture probes, the capture probes can hybridize or otherwise bind a target analyte. The sample can then be optionally removed from the array.

Adapters and assay primers can be used to allow the capture probe or the analyte capture agent to be attached to any suitable assay primers and used in any suitable assays. A capture probe that includes a spatial barcode can be attached to a bead that includes a poly(dT) sequence. A capture probe including a spatial barcode and a poly(T) sequence can be used to assay multiple biological analytes as generally described herein (e.g., the biological analyte includes a poly(A) sequence or is coupled to or otherwise is associated with an analyte capture agent comprising a poly (A) sequence as the analyte capture sequence).

The capture probes can be optionally cleaved from the array, and the captured analytes can be spatially-tagged by performing a reverse transcriptase first strand cDNA reaction. A first strand cDNA reaction can be optionally performed using template switching oligonucleotides. For example, a template switching oligonucleotide can hybridize to a poly(C) tail added to a 3' end of the cDNA by a reverse transcriptase enzyme. The original mRNA template and template switching oligonucleotide can then be denatured from the cDNA and the barcoded capture probe can then hybridize with the cDNA and a complement of the cDNA can be generated. The first strand cDNA can then be purified and collected for downstream amplification steps. The first strand cDNA can be amplified using PCR, wherein the forward and reverse primers flank the spatial barcode and target analyte regions of interest, generating a library associated with a particular spatial barcode. In some embodiments, the cDNA comprises a sequencing by synthesis (SBS) primer sequence. The library amplicons are sequenced and analyzed to decode spatial information.

In some embodiments, the sample is removed from the spatially-barcoded array and the spatially-barcoded capture probes are removed from the array for barcoded analyte amplification and library preparation. Another embodiment includes performing first strand synthesis using template switching oligonucleotides on the spatially-barcoded array without cleaving the capture probes. Once the capture probes capture the target analyte(s), first strand cDNA created by template switching and reverse transcriptase is then denatured and the second strand is then extended. The second strand cDNA is then denatured from the first strand cDNA, and transferred to a separate vessel (e.g., tube). cDNA quantification and amplification can be performed using standard techniques discussed herein. The cDNA can then be subjected to library preparation and indexing, including fragmentation, end-repair, A-tailing, indexing PCR steps, and then sequenced.

VI. Terminology

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

As used in this specification and the appended claims, the singular forms "a," "an" and "the" include plural referents unless the context clearly dictates otherwise. Thus, for example, reference to "a molecule" includes a plurality of such molecules, and the like.

A sample such as a biological sample can include any number of macromolecules, for example, cellular macro-molecules and organelles (e.g., mitochondria and nuclei). The biological sample can be a nucleic acid sample and/or protein sample. The biological sample can be a carbohydrate sample or a lipid sample. The biological sample can be obtained as a tissue sample, such as a tissue section, biopsy, a core biopsy, needle aspirate, or fine needle aspirate. The sample can be a fluid sample, such as a blood sample, urine sample, or saliva sample. The sample can be a skin sample, a colon sample, a cheek swab, a histology sample, a his-topathology sample, a plasma or serum sample, a tumor sample, living cells, cultured cells, a clinical sample such as, for example, whole blood or blood-derived products, blood cells, or cultured tissues or cells, including cell suspensions. In some embodiments, the biological sample may comprise cells which are deposited on a surface.

The term "barcode," comprises a label, or identifier, that conveys or is capable of conveying information (e.g., infor-mation about an analyte in a sample, a bead, and/or a capture probe). A barcode can be part of an analyte, or independent of an analyte. A barcode can be attached to an analyte. A particular barcode can be unique relative to other barcodes. Barcodes can have a variety of different formats. For example, barcodes can include polynucleotide barcodes, random nucleic acid and/or amino acid sequences, and synthetic nucleic acid and/or amino acid sequences. A barcode can be attached to an analyte or to another moiety or structure in a reversible or irreversible manner. A barcode can be added to, for example, a fragment of a deoxyribo-nucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI").

Barcodes can spatially-resolve molecular components found in biological samples, for example, at single-cell scale resolution (e.g., a barcode can be or can include a "spatial barcode"). In some embodiments, a barcode includes both a UMI and a spatial barcode. In some embodiments, a barcode includes two or more sub-barcodes that together function as a single barcode. For example, a polynucleotide barcode can include two or more polynucleotide sequences (e.g., sub-barcodes) that are separated by one or more non-barcode sequences.

As used herein, the term "substrate" generally refers to a substance, structure, surface, material, means, or composi-tion, which comprises a nonbiological, synthetic, nonliving, planar, spherical or flat surface. The substrate may include, for example and without limitation, semiconductors, syn-thetic metals, synthetic semiconductors, insulators and dop-ants; metals, alloys, elements, compounds and minerals; synthetic, cleaved, etched, lithographed, printed, machined and microfabricated slides, wafers, devices, structures and surfaces; industrial polymers, plastics, membranes; silicon, silicates, glass, metals and ceramics; wood, paper, card-board, cotton, wool, cloth, woven and nonwoven fibers, materials and fabrics; nanostructures and microstructures. The substrate may comprise an immobilization matrix such as but not limited to, insolubilized substance, solid phase, surface, layer, coating, woven or nonwoven fiber, matrix, crystal, membrane, insoluble polymer, plastic, glass, bio-logical or biocompatible or bioerodible or biodegradable polymer or matrix, microparticle or nanoparticle. Other examples may include, for example and without limitation, monolayers, bilayers, commercial membranes, resins, matri-ces, fibers, separation media, chromatography supports, polymers, plastics, glass, mica, gold, beads, microspheres, nanospheres, silicon, gallium arsenide, organic and inor-ganic metals, semiconductors, insulators, microstructures and nanostructures. Microstructures and nanostructures may include, without limitation, microminiaturized, nanometer-scale and supramolecular probes, tips, bars, pegs, plugs, rods, sleeves, wires, filaments, and tubes.

As used herein, the term "nucleic acid" generally refers to a polymer comprising one or more nucleic acid subunits or nucleotides. A nucleic acid may include one or more sub-units selected from adenosine (A), cytosine (C), guanine (G), thymine (T) and uracil (U), or variants thereof. A nucleotide can include A, C, G, T or U, or variants thereof. A nucleotide can include any subunit that can be incorpo-rated into a growing nucleic acid strand. Such subunit can be an A, C, G, T, or U, or any other subunit that is specific to one or more complementary A, C, G, T or U, or comple-mentary to a purine (i.e., A or G, or variant thereof) or a pyrimidine (i.e., C, T or U, or variant thereof). A subunit can enable individual nucleic acid bases or groups of bases (e.g., AA, TA, AT, GC, CG, CT, TC, GT, TG, AC, CA, or uracil-counterparts thereof) to be resolved. In some examples, a nucleic acid is deoxyribonucleic acid (DNA) or ribonucleic acid (RNA), or derivatives thereof. A nucleic acid may be single-stranded or double-stranded.

The term "nucleic acid sequence" or "nucleotide sequence" as used herein generally refers to nucleic acid molecules with a given sequence of nucleotides, of which it may be desired to know the presence or amount. The nucleotide sequence can comprise ribonucleic acid (RNA) or DNA, or a sequence derived from RNA or DNA. Examples of nucleotide sequences are sequences corre-sponding to natural or synthetic RNA or DNA including genomic DNA and messenger RNA. The length of the sequence can be any length that can be amplified into nucleic acid amplification products, or amplicons, for example, up to about 20, 50, 100, 200, 300, 400, 500, 600, 700, 800, 1000, 1200, 1500, 2000, 5000, 10000 or more than 10000 nucleotides in length, or at least about 20, 50, 100, 200, 300, 400, 500, 600, 700, 800, 1000, 1200, 1500, 2000, 5000, 10000 nucleotides in length.

The terms "oligonucleotide" and "polynucleotide" are used interchangeably to refer to a single-stranded multimer of nucleotides from about 2 to about 500 nucleotides in length. Oligonucleotides can be synthetic, made enzymatically (e.g., via polymerization), or using a "split-pool" method. Oligonucleotides can include ribonucleotide monomers (i.e., can be oligoribonucleotides) and/or deoxyribonucleotide monomers (i.e., oligodeoxyribonucleotides). In some examples, oligonucleotides can include a combination of both deoxyribonucleotide monomers and ribonucleotide monomers in the oligonucleotide (e.g., random or ordered combination of deoxyribonucleotide monomers and ribonucleotide monomers). An oligonucleotide can be 4 to 10, 10 to 20, 21 to 30, 31 to 40, 41 to 50, 51 to 60, 61 to 70, 71 to 80, 80 to 100, 100 to 150, 150 to 200, 200 to 250, 250 to 300, 300 to 350, 350 to 400, or 400-500 nucleotides in length, for example. Oligonucleotides can include one or more functional moieties that are attached (e.g., covalently or non-covalently) to the multimer structure. For example, an oligonucleotide can include one or more detectable labels (e.g., a radioisotope or fluorophore).

As used herein, the term "adjacent" or "adjacent to," includes "next to," "adjoining," and "abutting." In one example, a first location is adjacent to a second location when the first location is in direct contact and shares a common border with the second location and there is no space between the two locations. In some cases, the adjacent is not diagonally adjacent.

An "adaptor," an "adapter," and a "tag" are terms that are used interchangeably in this disclosure, and refer to species that can be coupled to a polynucleotide sequence (in a process referred to as "tagging") using any one of many different techniques including (but not limited to) ligation, hybridization, and tagmentation. Adaptors can also be nucleic acid sequences that add a function, e.g., spacer sequences, primer sequences/sites, barcode sequences, unique molecular identifier sequences.

The terms "hybridizing," "hybridize," "annealing," and "anneal" are used interchangeably in this disclosure, and refer to the pairing of substantially complementary or complementary nucleic acid sequences within two different molecules. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

A "proximity ligation" is a method of ligating two (or more) nucleic acid sequences that are in proximity with each other through enzymatic means (e.g., a ligase). In some embodiments, proximity ligation can include a "gap-filling" step that involves incorporation of one or more nucleic acids by a polymerase, based on the nucleic acid sequence of a template nucleic acid molecule, spanning a distance between the two nucleic acid molecules of interest (see, e.g., U.S. Pat. No. 7,264,929, the entire contents of which are incorporated herein by reference).

A wide variety of different methods can be used for proximity ligating nucleic acid molecules, including (but not limited to) "sticky-end" and "blunt-end" ligations. Additionally, single-stranded ligation can be used to perform proximity ligation on a single-stranded nucleic acid molecule. Sticky-end proximity ligations involve the hybridization of complementary single-stranded sequences between the two nucleic acid molecules to be joined, prior to the ligation event itself. Blunt-end proximity ligations generally do not include hybridization of complementary regions from each nucleic acid molecule because both nucleic acid molecules lack a single-stranded overhang at the site of ligation As used herein, the term "splint" is an oligonucleotide that, when hybridized to other polynucleotides, acts as a "splint" to position the polynucleotides next to one another so that they can be ligated together. In some embodiments, the splint is DNA or RNA. The splint can include a nucleotide sequence that is partially complimentary to nucleotide sequences from two or more different oligonucleotides. In some embodiments, the splint assists in ligating a "donor" oligonucleotide and an "acceptor" oligonucleotide. In general, an RNA ligase, a DNA ligase, or another other variety of ligase is used to ligate two nucleotide sequences together.

In some embodiments, the splint is between 6 and 50 nucleotides in length, e.g., between 6 and 45, 6 and 40, 6 and 35, 6 and 30, 6 and 25, or 6 and 20 nucleotides in length. In some embodiments, the splint is between 10 and 50 nucleotides in length, e.g., between 10 and 45, 10 and 40, 10 and 35, 10 and 30, 10 and 25, or 10 and 20 nucleotides in length. In some embodiments, the splint is between 15 and 50, 15 and 45, 15 and 40, 15 and 35, 15 and 30, or 15 and 25 nucleotides in length.

A "feature" is an entity that acts as a support or repository for various molecular entities used in sample analysis. In some embodiments, some or all of the features in an array are functionalized for analyte capture. In some embodiments, functionalized features include one or more capture probe(s). Examples of features include, but are not limited to, a bead, a spot of any two- or three-dimensional geometry (e.g., an ink jet spot, a masked spot, a square on a grid), a well, and a hydrogel pad. In some embodiments, features are directly or indirectly attached or fixed to a substrate. In some embodiments, the features are not directly or indirectly attached or fixed to a substrate, but instead, for example, are disposed within an enclosed or partially enclosed three dimensional space (e.g., wells or divots).

The term "sequencing," as used herein, generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina®, Pacific Biosciences (PacBio®), Oxford Nanopore®, or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

The term "template" as used herein generally refers to individual polynucleotide molecules from which another nucleic acid, including a complementary nucleic acid strand, can be synthesized by a nucleic acid polymerase. In addition, the template can be one or both strands of the polynucleotides that are capable of acting as templates for template-dependent nucleic acid polymerization catalyzed by the nucleic acid polymerase. Use of this term should not be taken as limiting the scope of the present disclosure to polynucleotides which are actually used as templates in a subsequent enzyme-catalyzed polymerization reaction. The template can be an RNA or DNA. The template can be cDNA corresponding to an RNA sequence. The template can be DNA.

As used herein, "amplification" of a template nucleic acid generally refers to a process of creating (e.g., in vitro) nucleic acid strands that are identical or complementary to at least a portion of a template nucleic acid sequence, or a universal or tag sequence that serves as a surrogate for the template nucleic acid sequence, all of which are only made if the template nucleic acid is present in a sample. Typically, nucleic acid amplification uses one or more nucleic acid polymerase and/or transcriptase enzymes to produce multiple copies of a template nucleic acid or fragments thereof, or of a sequence complementary to the template nucleic acid or fragments thereof. In vitro nucleic acid amplification techniques are may include transcription-associated amplification methods, such as Transcription-Mediated Amplification (TMA) or Nucleic Acid Sequence-Based Amplification (NASBA), and other methods such as Polymerase Chain Reaction (PCR), Reverse Transcriptase-PCR (RT-PCR), Replicase Mediated Amplification, and Ligase Chain Reaction (LCR).

In addition to those above, a wide variety of other features can be used to form the arrays described herein. For example, in some embodiments, features that are formed from polymers and/or biopolymers that are jet printed, screen printed, or electrostatically deposited on a substrate can be used to form arrays.

EXAMPLES

The following examples are included for illustrative purposes only and are not intended to limit the scope of the present disclosure.

Example 1: Generation of an Oligonucleotide Array Using Photo-Hybridization/Ligation This example demonstrates a successful barcode assembly following four cycles of photoresist, on a lawn of immobilized oligonucleotides (e.g., an R1 primer lawn as shown in FIG. 3). In particular, this example describes the generation of a barcoded oligonucleotide array using photo-hybridization/ligation.

Figure 5:
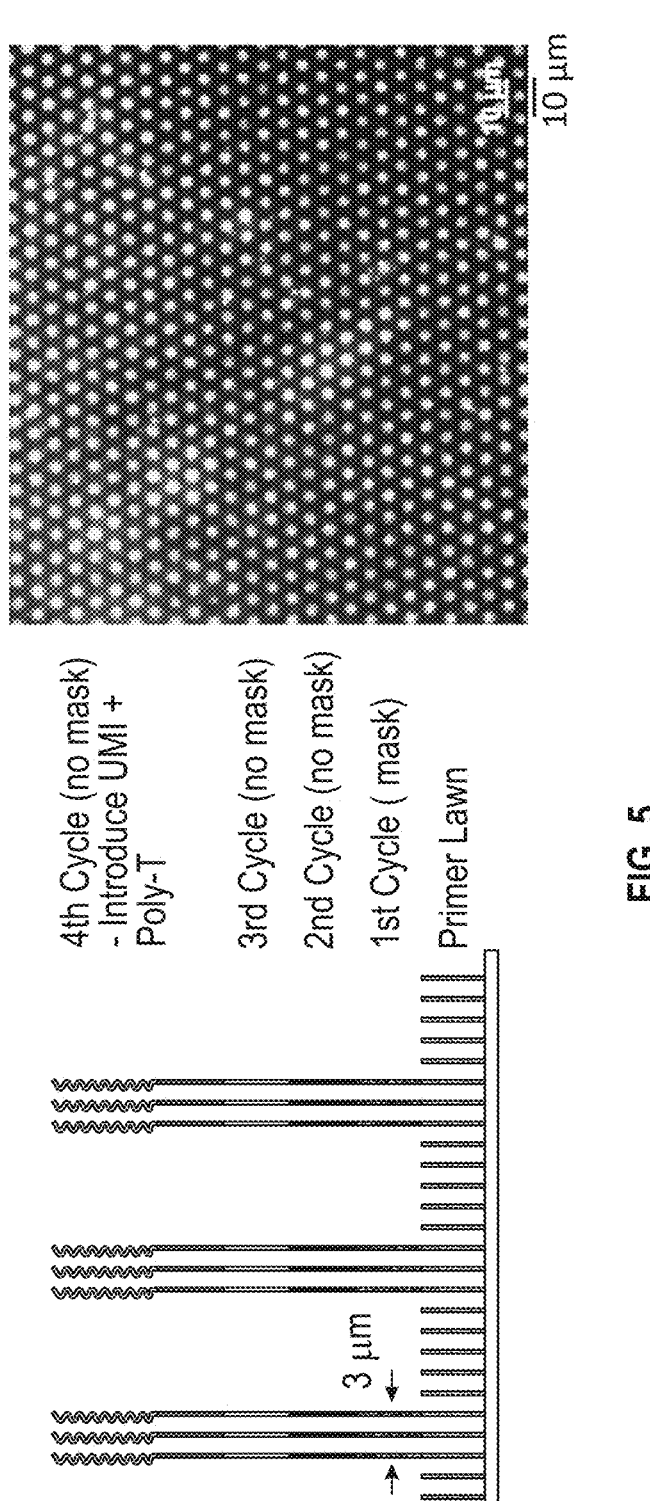
FIG. 5 shows an exemplary array comprising oligonucleotides comprising four barcode sequences sequentially added to a primer lawn.

FIG. 5 shows an array of barcoded immobilized oligonucleotides, produced from an in situ method described herein. A lawn of primer oligonucleotides was immobilized on a substrate. The substrate was a glass slide. The barcode sequences were assembled on the immobilized oligonucleotides, e.g., based on hybridization and/or ligation, on the substrate surface. Here, the method of generating the surface array comprised irradiating the substrate covered with a photoresist as shown in FIG. 1. A four-part photo-hybridization/ligation method comprised four cycles, each comprising attaching a barcode to the immobilized oligonucleotides in one or more features. Each attaching step hybridized a splint to immobilized oligonucleotides in the features and oligonucleotides comprising barcode sequences were added, followed by ligating the oligonucleotides. The splints can be designed to prevent undesirable insertions or deletions during the hybridization/ligation.

A $1^{st}$ cycle of hybridization/ligation was achieved by subjecting the primer lawn to hybridization/ligation upon degradation of the photoresist, by irradiating the substrate through a photomask. A $2^{nd}$, $3^{rd}$, and $4^{th}$ cycle of hybridization/ligation did comprise the use of a photomask, allowing for the assembly of additional barcode sequences directly upon molecules in the features from the $1^{st}$ cycle of hybridization/ligation. The features in FIG. 5 had a mean diameter of about 3.01 μm, a mean pitch of about 5.62 μm, with a CV of about 10%.

As illustrated in FIG. 5, the $4^{th}$ cycle of hybridization/ligation added a UMI and a poly(T) domain. Poly(T) sequences were configured to interact with messenger RNA (mRNA) molecules via the poly(A) tail of an mRNA transcript. Ultimately, the poly(T) sequence were probed by annealing polydA oligonucleotides to the full length barcoded oligonucleotides. Only immobilized barcoded oligonucleotides containing a poly(dT) sequence would fluoresce producing a signal (e.g., right panel, FIG. 5), indicating the successful generation of a barcoded oligonucleotide array having features approximately 3 microns in diameter.

Example 2: Analyzing Mouse Brain Tissue Using a Spatial Barcode Array

This example demonstrates an application of an array generated using a photo-hybridization/ligation method, described herein, for analyzing a mouse brain tissue section.

Figure 6:
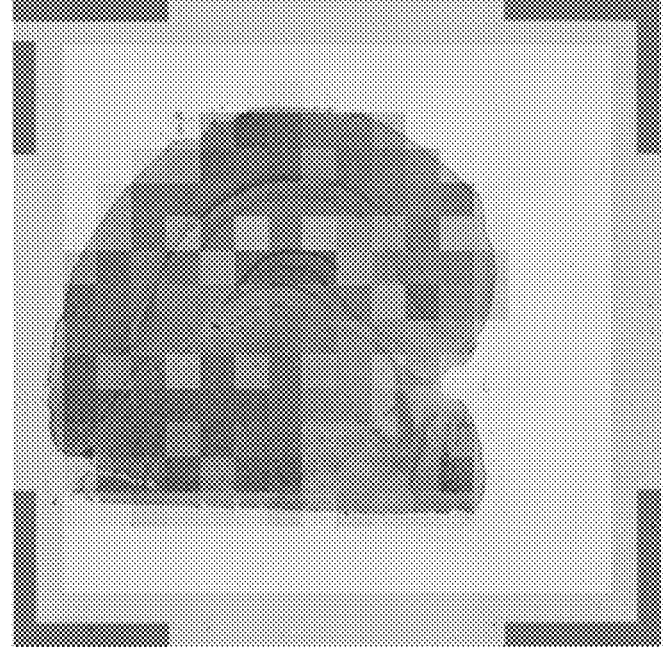
FIG. 6 shows results of analyzing a mouse brain tissue section using an exemplary array.
Figure 6:
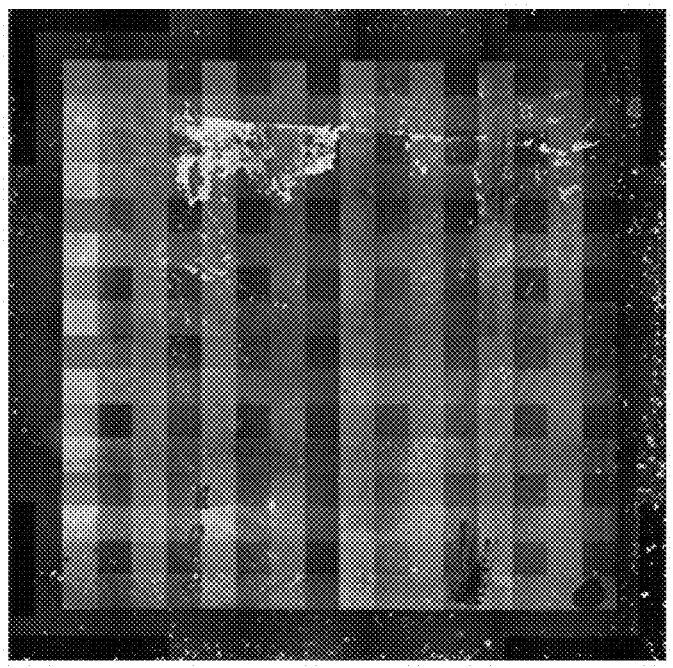

FIG. 6 shows an exemplary spatial array generated using a combinatorial barcoding approach as shown in FIG. 4B. 1,161,216 features (circles in FIG. 4B) were produced with a 5 μm feature diameter and a 7 μm pitch per 7×7 mm area on a substrate. 256 square areas in the 7×7 mm array area were generated over 4 rounds of photo-hybridization/ligation (4 cycles per round, 16 cycles in total). Using a scheme similar to that shown in FIG. 3, features within each of the 4 square areas in Round A received barcode Part A, features within each of the 16 smaller square areas in Round B received barcode Part B, features within each of the 64 even smaller square areas in Round C received barcode Part C, and features within each of the final 256 square areas in Round D received barcode Part D of a spatial barcode. A spatial array comprising 256 combinatorially generated 4-part spatial barcodes was generated, where each of the 256 spatial barcodes was unique to the square area but shared by the feature and the oligonucleotide probes within the feature. Fluorescently labelled probes for the 256 unique spatial barcodes were applied to the array to generate the fluorescent image in FIG. 6 (left).

A mouse brain tissue section was deposited on the spatial array and processed. The tissue section was permeabilized, and mRNA molecules from tissue section were captured on the spatial array via the polyT sequence of the capture domains in the oligonucleotide probes on the spatial array. First strand cDNAs were created on the spatial array using reverse transcription of the captured mRNAs, second strand synthesis was performed via template switching to generate second strand cDNAs, which were denatured from the spatial array and sequenced. The second strand cDNAs contained nucleotide sequences complementary to the spatial barcodes and UMIs in the oligonucleotide probes on the array, allowing the sequencing reads to be mapped back to features on the spatial array.

The tissue section was stained using H&E (hematoxylin and eosin) and imaged. The sequencing reads were refined to remove duplicate UMI's allowing for accurate quantitation of analytes (e.g., mRNA transcripts) in the tissue section. UMIs by feature (i.e., spatial barcode) were overlaid with the H&E image in FIG. 6 (right), showing that the mRNA transcript gene expression profile obtained using the 256 combinatorially generated 4-part spatial array generally matched the expected transcript profile of mouse brain tissue. These results suggest that expression profiles for individual transcripts can be analyzed with an array generated using a photo-hybridization/ligation method disclosed herein, and combined with the information obtained from the tissue sections through staining (e.g., H&E or immuno-fluorescent (IF) stain).

The present disclosure is not intended to be limited in scope to the particular disclosed embodiments, which are provided, for example, to illustrate various aspects of the present disclosure. Various modifications to the compositions and methods described will become apparent from the description and teachings herein. Such variations may be practiced without departing from the true scope and spirit of the disclosure and are intended to fall within the scope of the present disclosure.

The invention claimed is:

1. A method for providing an array, comprising:
(a) irradiating a substrate comprising a layer of positive photoresist to expose a first region and not expose a second region, wherein oligonucleotide molecules attached to the substrate at their 5' ends in the first region and in the second region are embedded in the layer of positive photoresist and comprise 3' hydroxyl functional groups that are not protected by a protecting group;
(b) treating the layer of positive photoresist with a developer solution to dissolve and remove the layer of positive photoresist in the first region, thereby rendering 3' hydroxyl functionalized ends of the oligonucleotide molecules attached to the substrate in the first region available for hybridization and/or ligation, whereas 3' hydroxyl functionalized ends of the oligonucleotide molecules attached to the substrate in the second region are protected by the layer of positive photoresist in the second region from hybridization and/or ligation; and
(c) attaching an oligonucleotide comprising a barcode sequence to a 3' hydroxyl functionalized end of an oligonucleotide molecule of the oligonucleotide molecules attached to the substrate in the first region via hybridization and/or ligation, wherein the 3' hydroxyl functionalized ends of the oligonucleotide molecules attached to the substrate in the second region do not receive the barcode sequence,
thereby providing, on the substrate, an array comprising different oligonucleotide molecules in the first region and the second region.

2. The method of claim 1, wherein the oligonucleotide molecules attached to the substrate in the first region and the oligonucleotide molecules attached to the substrate in the second region comprise one or more common sequences.

3. The method of claim 1, further comprising, prior to (a), forming a pattern of oligonucleotide molecules on an initial substrate to generate the substrate.

4. The method of claim 3, wherein forming the pattern of oligonucleotide molecules comprises:
irradiating the initial substrate, wherein the initial substrate comprises a plurality of functional groups and an initial layer of positive photoresist, through a patterned mask and treating the initial layer of positive photoresist with a developer solution, thereby producing a treated substrate, whereby the initial layer of positive photoresist in a first region of the initial substrate is dissolved and removed, thereby rendering functional groups in the first region of the initial substrate available for reacting with 5' functional groups in functionalized oligonucleotide molecules, whereas functional groups in a second region of the initial substrate are protected by the initial layer of positive photoresist in the second region from reacting with the 5' functional groups in the functionalized oligonucleotide molecules; and
contacting the treated substrate with the functionalized oligonucleotide molecules, thereby coupling the 5' functional groups in the functionalized oligonucleotide molecules to the functional groups in the first region but not to the functional groups in the second region, thereby forming the pattern of oligonucleotide molecules on the treated substrate and generating the substrate.

5. The method of claim 4, wherein the 5' functional groups in the functionalized oligonucleotide molecules are amino groups.

6. The method of claim 4, further comprising blocking unreacted functional groups of the treated substrate that have not been coupled to the functionalized oligonucleotide molecules.

7. The method of claim 4, wherein the irradiating and contacting are repeated in one or more cycles.

8. The method of claim 7, wherein the initial layer of positive photoresist is not removed prior to the one or more cycles.

9. The method of claim 1, wherein (a) comprises irradiating the substrate through a patterned mask.

10. The method of claim 9, further comprising, after the irradiating, removing the patterned mask from the substrate, and re-using the patterned mask in a subsequent cycle of the irradiating and the attaching.

11. The method of claim 1, wherein the barcode sequence is between about 4 and about 25 nucleotides in length.

12. The method of claim 1, wherein the oligonucleotide comprising the barcode sequence is between about 10 and about 50 nucleotides in length.

13. The method of claim 1, wherein the oligonucleotide comprising the barcode sequence is hybridized to a 3' hydroxyl functionalized end of an oligonucleotide molecule attached to the substrate in the first region.

14. The method of claim 1, wherein (c) comprises ligating the oligonucleotide comprising the barcode sequence to the 3' hydroxyl functionalized end of the oligonucleotide molecule attached to the substrate in the first region.

15. The method of claim 1, wherein the oligonucleotide comprising the barcode sequence is hybridized to a splint which is in turn hybridized to the 3' hydroxyl functionalized end of the oligonucleotide molecule attached to the substrate in the first region.

16. The method of claim 15, further comprising ligating the oligonucleotide comprising the barcode sequence to the 3' hydroxyl functionalized end of oligonucleotide molecule to generate a barcoded oligonucleotide molecule attached to the substrate in the first region.

17. The method of claim 16, further comprising blocking 3' termini of barcoded oligonucleotide molecules and/or unligated oligonucleotide molecules attached to the substrate in the first region from ligation.

18. The method of claim 1, wherein the method comprises performing (a)-(c) for N cycles, wherein N is an integer of 2 or greater.

19. The method of claim 18, wherein the barcode sequences received by oligonucleotide molecules in a feature on the substrate in cycle I and in the feature on the substrate in cycle J are different, wherein I and J are integers and $1 \leq I < J \leq N$.

20. The method of claim 19, wherein the layer of positive photoresist is not removed between cycles of the N cycles.

21. The method of claim 19, wherein the feature is no more than 10 microns in diameter.

22. The method of claim 1, comprising contacting the 3' hydroxyl functionalized ends of the oligonucleotide molecules attached to the substrate in the first region with first splints and first oligonucleotides comprising the barcode sequence, wherein the barcode sequence is a first barcode sequence, wherein the first splints hybridize to the first oligonucleotides and hybridize to the 3' hydroxyl functionalized ends of the oligonucleotide molecules attached to the substrate in the first region, wherein the first oligonucleotides comprising the first barcode sequence are ligated to the 3' hydroxyl functionalized ends of the oligonucleotide molecules attached to the substrate in the first region to generate first extended oligonucleotide molecules, and the first oligonucleotides comprising the first barcode sequence are not ligated to the 3' hydroxyl functionalized ends of the oligonucleotide molecules attached to the substrate in the second region, thereby providing on the substrate an array comprising different oligonucleotide molecules in the first region and the second region.

23. The method of claim 2, wherein the layer of positive photoresist is a first layer of positive photoresist, and the method further comprises:

(c) applying a second layer of positive photoresist to the substrate;

(d) irradiating the substrate while the first region is masked and the second region is unmasked and treating the first layer of positive photoresist or the second layer of positive photoresist with a developer solution, whereby the first layer of positive photoresist or the second layer of positive photoresist in the second region is dissolved and removed to render 3' hydroxyl functionalized ends of the oligonucleotide molecules attached to the substrate in the second region and embedded in the first layer of positive photoresist or the second layer of positive photoresist available for hybridization and/or ligation, whereas 3' hydroxyl functionalized ends of the first extended oligonucleotide molecules attached to the substrate in the first region are protected by the second layer of positive photoresist in the first region from hybridization and/or ligation; and (e) contacting the 3' hydroxyl functionalized ends of the oligonucleotide molecules attached to the substrate in the second region with second splints and second oligonucleotides comprising a second barcode sequence, wherein the second splints hybridize to the second oligonucleotides and hybridize to the 3' hydroxyl functionalized ends of the oligonucleotide molecules attached to the substrate in the second region, wherein the second oligonucleotides comprising the second barcode sequence are ligated to the 3' hydroxyl functionalized ends of the oligonucleotide molecules attached to the substrate in the second region to generate second extended oligonucleotide molecules, and the second oligonucleotides comprising the second barcode sequence are not ligated to the 3' hydroxyl functionalized ends of the first extended oligonucleotide molecules attached to the substrate in the first region.

24. The method of claim 23, wherein the second layer of positive photoresist is applied after the first layer of positive photoresist is removed from the substrate.

* * * * *